United States Patent [19]
Collins et al.

[11] Patent Number: 5,874,075
[45] Date of Patent: Feb. 23, 1999

[54] STABLE PROTEIN: PHOSPHOLIPID COMPOSITIONS AND METHODS

[75] Inventors: David Collins, Thousand Oaks, Calif.; Younsik Cha, Salt Lake City, Utah; David Brems, Newbury Park, Calif.

[73] Assignee: Amgen Inc., Thousand Oaks, Calif.

[21] Appl. No.: 414,161

[22] Filed: Mar. 31, 1995

Related U.S. Application Data

[63] Continuation-in-part of Ser. No. 361,011, Dec. 21, 1994, abandoned, which is a continuation of Ser. No. 132,413, Oct. 6, 1993, abandoned.

[51] Int. Cl.[6] .......................... A61K 38/19; A61K 9/127; C07K 14/52; C07K 14/535
[52] U.S. Cl. .................. 424/85.1; 530/351; 930/140; 930/145; 424/450
[58] Field of Search ................... 424/85.1, 450; 435/69.5; 514/2; 530/351; 264/4.1; 930/140, 145

[56] References Cited

U.S. PATENT DOCUMENTS

| | | | |
|---|---|---|---|
| 4,515,736 | 5/1985 | Deamer | 264/4.3 |
| 4,744,989 | 5/1988 | Payne et al. | 424/490 |
| 4,766,106 | 8/1988 | Katre et al. | 514/12 |
| 4,810,643 | 3/1989 | Souza | 435/68 |
| 5,225,212 | 7/1993 | Martin et al. | 424/450 |

FOREIGN PATENT DOCUMENTS

| | | |
|---|---|---|
| 0 422 543 A1 | 10/1990 | European Pat. Off. . |
| 0 393 707 A2 | 4/1991 | European Pat. Off. . |
| WO 89/11270 | 11/1989 | WIPO . |
| WO 91/04019 | 4/1991 | WIPO . |

OTHER PUBLICATIONS

Hill, C., et al., "The Structure of Granulocyte–Colony–Stimulating Factor and Its Relationship to Other Growth Factors," *Proc. Natl. Acad. Sci. USA* 90:5167–5171 (1993).

Horowitz, P., "Kinetic Control of Protein Folding by Detergent Micelles, Liposomes, and Chaperonins," *Protein Folding In Vivo and In Vitro,* Cleland, J. Ed., ACS Symposium Series 526, pp. 156–163, 1993.

Lu, H., et al., "Folding and Oxidation of Recombinant Human Granulocyte Colony Stimulating Factor Produced in *Escherichia coli* " *J. Biol. Chem.* 267(13):8770–8777 (1992).

Morjana, N., et al., "Guanidine Hydrochloride Stabilization of a Partially Unfolded Intermediate During the Reversible Denaturation of Protein Disulfide Isomerase," *Proc. Natl. Acad. Sci. USA* 90:2107–2111 (1993).

Narhi, L., et al., "Conformational Changes of Recombinant Human Granulocyte–Colony Stimulating Factor Induced by pH and Guanindine Hydrochloride," *J. Protein Chem.* 10(4):359–367 (1991).

Patent Abstracts of Japan, vol. 016, No. 298 (C–0958), Jul. 2, 1992.

Ptitsyn et al. FEBS 252(1): 20–24, 1990.

van du Goot et al. Nature 354: 408–410, 1991.

Goto et al. Biochemistry 29: 3480–3488, 1990.

Anderson et al. Cancer Res. 50(6): 1853–1856, 1990.

Callard et al. "The Cytokine Factsbook", Acad. Press, 247–251, 1994.

*Primary Examiner*—John Ulm
*Assistant Examiner*—Christine Saoud
*Attorney, Agent, or Firm*—Craig A. Crandall; Ron K. Levy; Steven M. Odre

[57] ABSTRACT

The invention relates to stable compositions of proteins and related methods wherein a protein capable of transitioning into the molten globular state is contacted with a negatively charged lipid vesicle, thereby stabilizing the protein against thermally-induced aggregation, denaturation, and loss of activity. The protein:phospholipid complex directly stabilizes the secondary and tertiary structure of the protein, and the compositions are useful in high temperature formulations and in novel delivery vehicles.

42 Claims, 35 Drawing Sheets

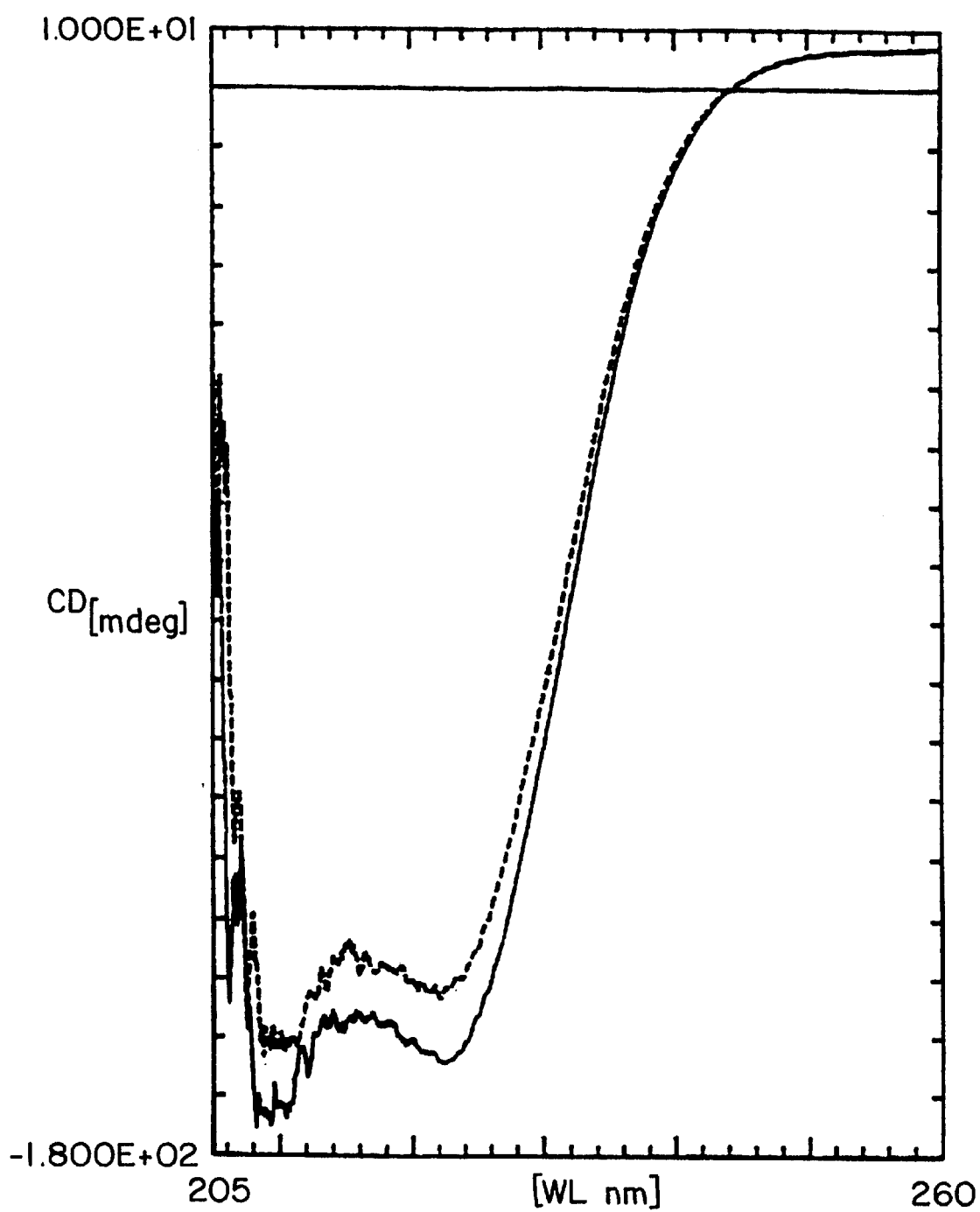

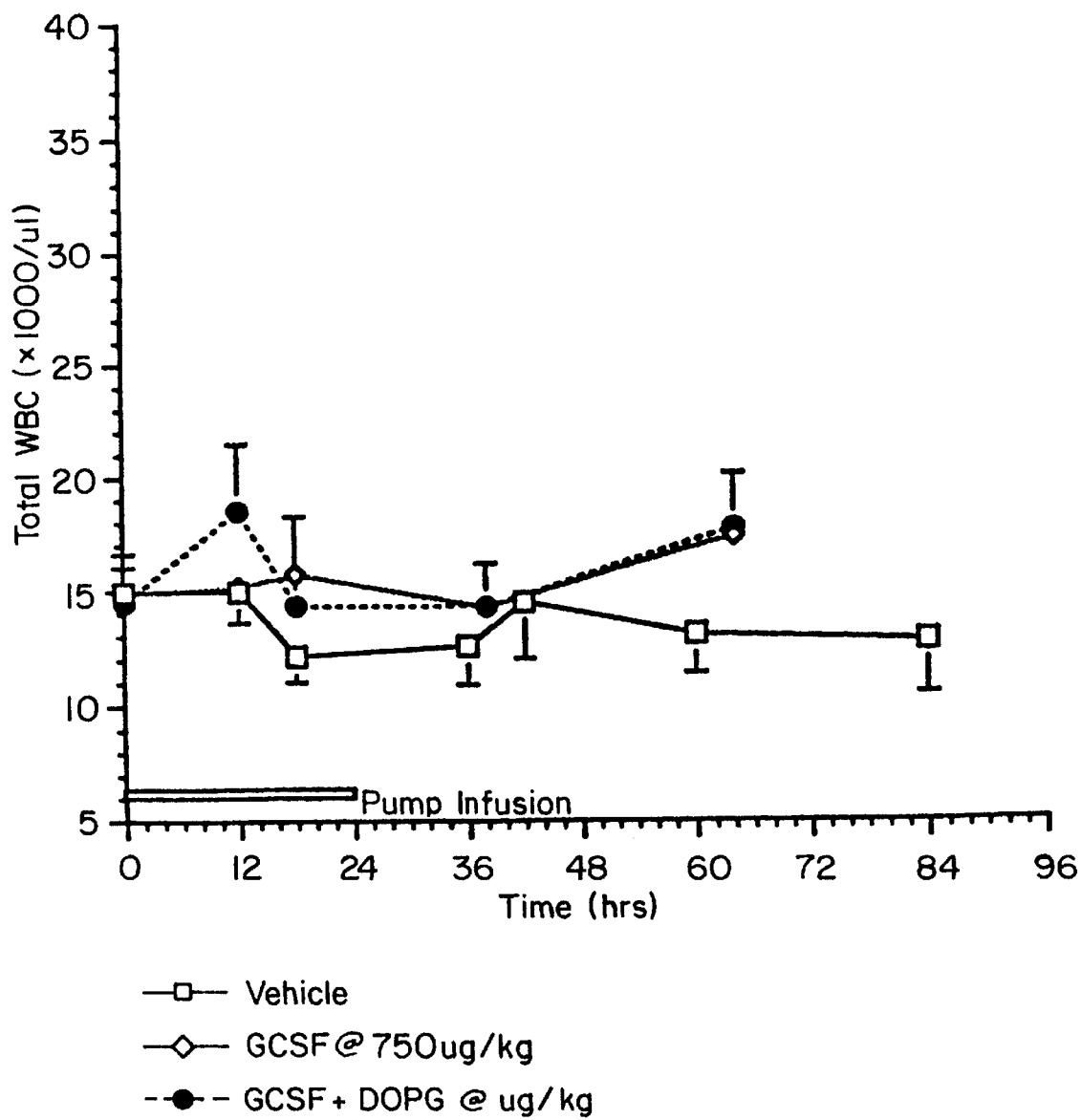

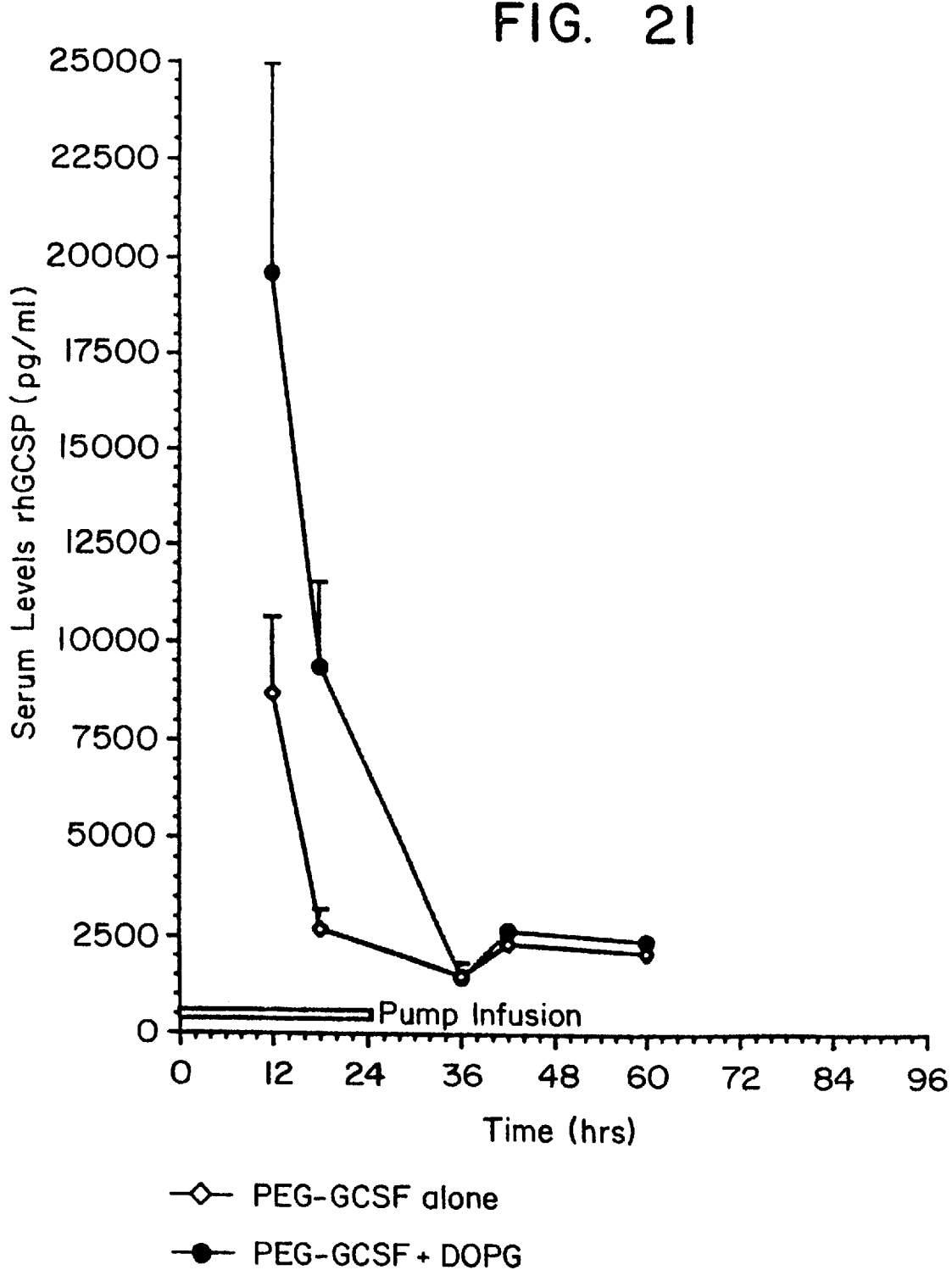

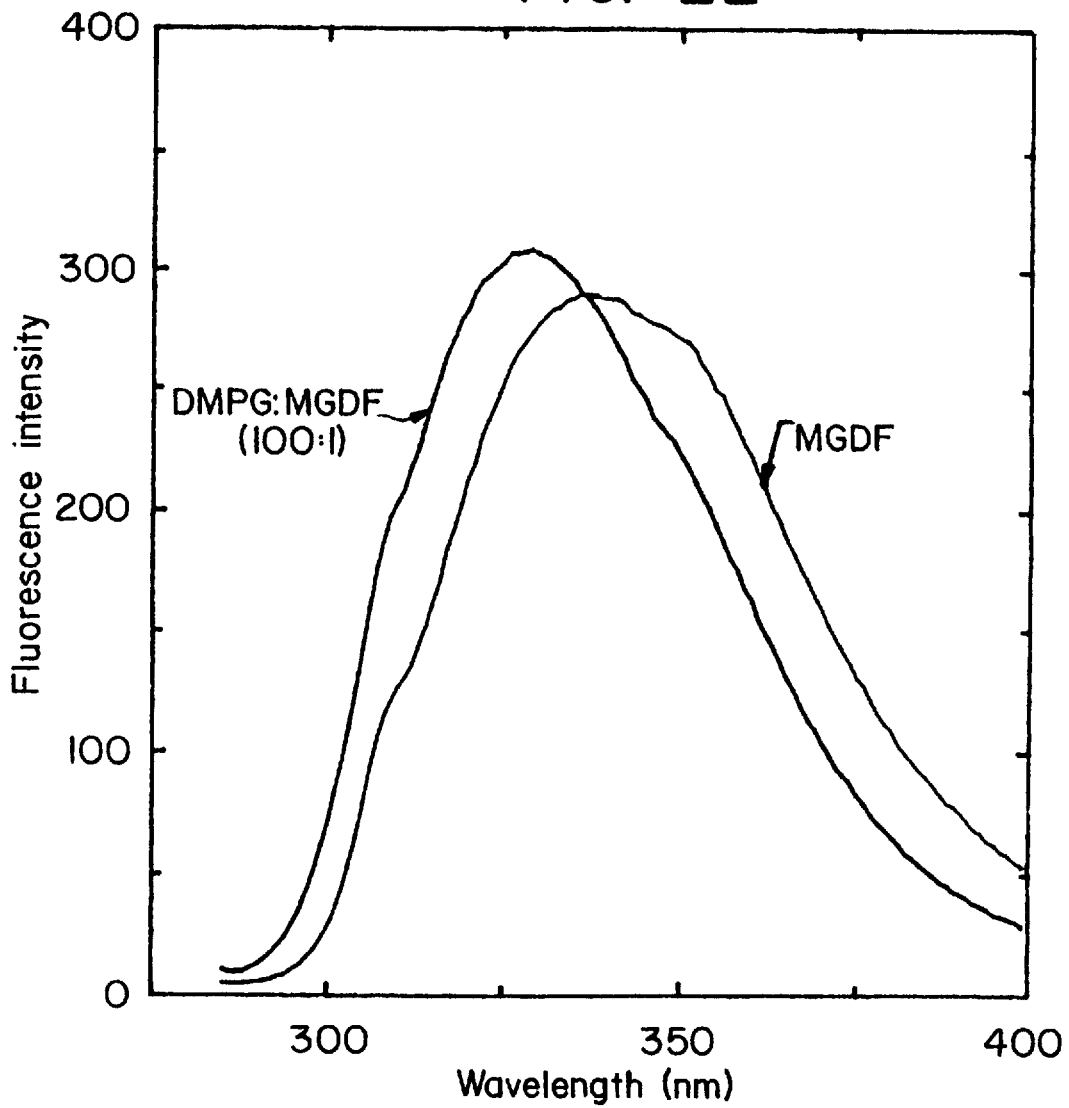

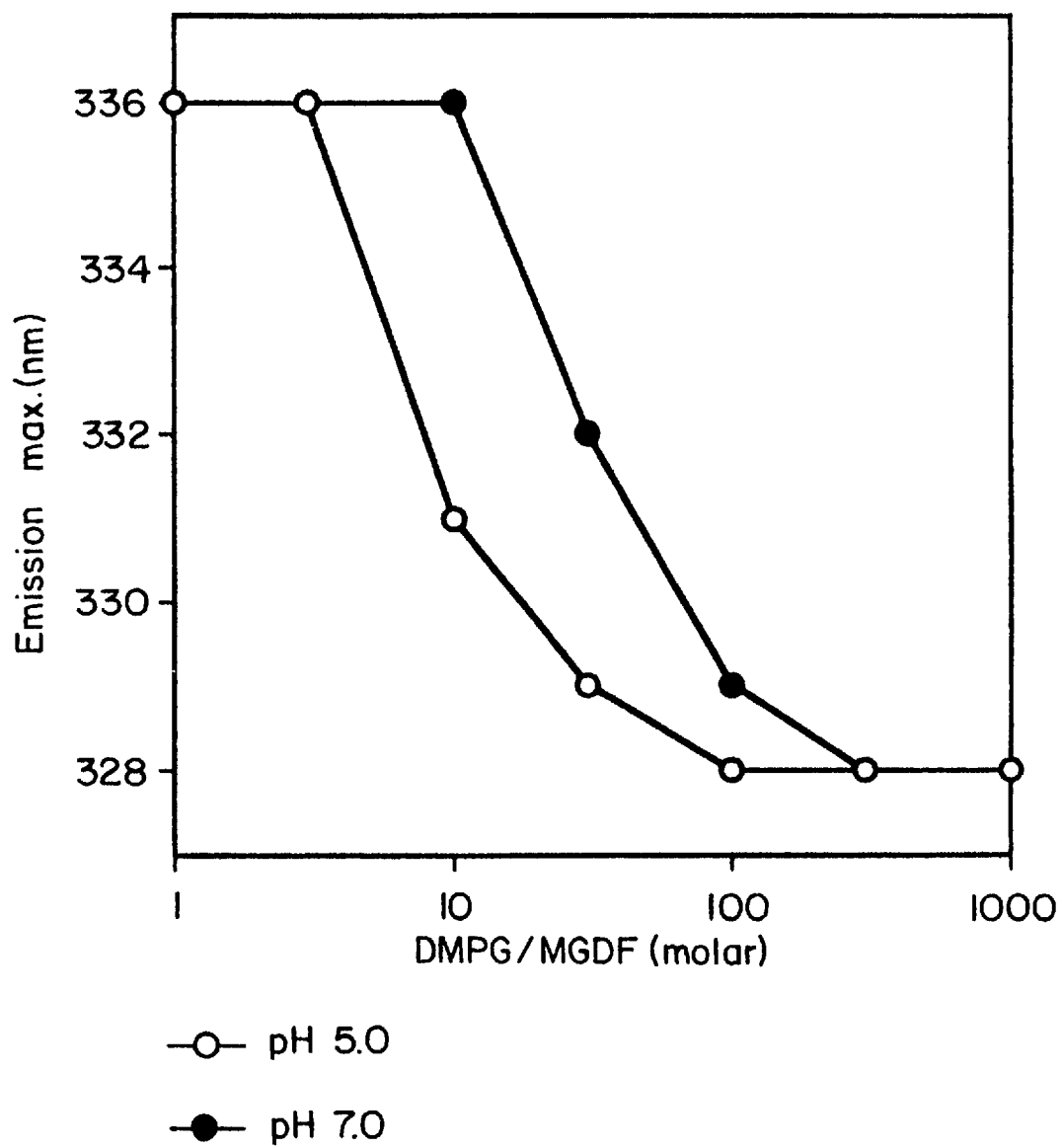

○ MDGF
● DMPG:MGDF (100:1)

FIG.29A

```
1    CAGGGAGCCACGCCAGCAAGACACCCCGGCCCAGAATGGAGCTGACTGAATTGCTCCTC         53
-21                                      MetGluLeuThrGluLeuLeuLeu      -14

70   GTGGTCATGCTTCTCCTAACTGCAAGGCTAAGCTGTCCAGCCCGGCTCCTCCTGCTTGT        119
-13  ValValMetLeuLeuLeuThrAlaArgLeuThrAlaArgLeuSerSerProAlaProProAlaCys   7

120  GACCTCCGAGTCCTCAGTAAACTGCTTCGTGACTCCCATGTCCTTCACAGCAGACTGAGC       179
8    AspLeuArgValLeuSerLysLeuLeuLeuArgAspSerHisValLeuHisSerArgLeuSer     27

180  CAGTGCCCAGAGGTTCACCCTTTGCCTACACCTGTCCTGCTGCCTGTGGACTTTAGC          239
28   GlnCysProGluValHisProLeuProThrProValLeuLeuProAlaValAspPheSer       47

240  TTGGGAGAATGGAAAACCCAGATGGAGGAGACCAAGGCACAGAACATTCTGGAGCAGTG        299
48   LeuGlyGluTrpLysThrGlnMetGluGluThrLysAlaGlnAspIleLeuGluGlyAlaVal    67

300  ACCCTTCTGCTGGAGGAGTGATGCAGCAACGGGGACAACTGGGACCACTTGCCTCTCA         359
68   ThrLeuLeuLeuGluGluGlyValMetAlaAlaArgGlyGlnLeuGlyProThrCysLeuSer    87

360  TCCCTCCTGGGCAGCTTTCTGGACAGTCCGTCTCCTCCTTGGGCCCTGCAGAGCCTC         419
88   SerLeuLeuGlyGlnLeuLeuSerGlyGlnValArgLeuLeuLeuLeuAlaLeuGlnSerLeu   107

420  CTTGGAACCCAGCTTCCTCACAGGGCAGACCACAGCTCACAAGGATCCCAATGCCATCC        479
108  LeuGlyThrGlnLeuProProGlnGlyArgThrAlaHisLysAspProAsnAlaIle         127

480  TTCCTGAGCTTCCAACACCTGCTCCGAGGAAAGGTGCGTTTCCTGATGCTTGTAGGAGGG      539
128  PheLeuSerPheGlnHisLeuLeuArgGlyLysValArgPheLeuMetLeuValGlyGly      147

540  TCCACCCTCTGCGTCAGGCGGCCCCACCACCAGCTGTCCCCAGCAGAACCTCTCTA          599
148  SerThrLeuCysValArgArgAlaProProThrThrAlaValProSerArgThrSerLeu      167
```

FIG. 29B

```
600  GTCCTCACACTGAACGAGCTCCCAAACAGGACTTCTGATTGTTGGAGACAAACTTCACT   659
168  ValLeuThrLeuAsnGluLeuProAsnArgThrSerGlyLeuLeuGluThrAsnPheThr  187

660  GCCTCAGCCAGAACTACTGGCTCTGGGCTTCTGAAGTGGCAGGAGGATTCAGAGCCAAG   719
188  AlaSerAlaArgThrThrGlySerGlyLeuLeuLysTrpGlnGlnGlyPheArgAlaLys  207

720  ATTCCTGGTCTGCTGAACCAAACCTCCAGTCCCTGGACCCAAATCCCGGATACCTGAAC   779
208  IleProGlyLeuLeuAsnGlnThrSerArgSerLeuAspGlnIleProGlyTyrLeuAsn  227

780  AGGATACACGAACTCTTGAATGGAACTCGTGGACTCTTTCCTGACCCTCACGCAGGACC   839
228  ArgIleHisGluLeuLeuAsnGlyThrArgGlyLeuPheProGlyProSerArgArgThr  247

840  CTAGGAGCCCGGACATTTCCTCAGGAACATCAGACAGGCTCCCTGCCACCCAACCTC    899
248  LeuGlyAlaProAspIleSerSerGlyThrSerAspThrGlySerLeuProProAsnLeu  267

900  CAGCCTGGATATTCCTCCCCAACCCATCCTCCTACTGACAGTATACGCTCTTCCCT     959
268  GlnProGlyTyrSerProSerProThrHisProProThrGlyGlnThrTyrThrLeuPhePro  287

960  CTTCCACCACCTTGCCCAGTCCAGTCCACCCCTGTTCCTGACCCTTCT            1019
288  LeuProThrThrLeuProProThrProValValGlnLeuHisProLeuLeuProAspProSer  307

1020 GCTCCAACGCCCTGCAGGGCGCCCTGGTAAAGGGATACACAGGACTGCCGACATCCCAGAAT 1079
308  AlaProThrProThrSerProLeuLeuAsnThrSerTyrThrThrHisSerGlnAsn    327

1080 CTGTCTCAGGAAGGGTAAGGTTCTCAGACTTCTCAGACATGCCGACATCAGCCGACATTGTCTCGTGTACAG 1139
329  LeuSerGlnGluGlyEnd

1140 CTCCCTTCCCTGCAGGGCGCCCTGCAGGAGACAACTGGACAAGATTTCCTACTTTCCTG   1199
1200 AAACCCAAGCCCTGGTAAAAGGGATACACAGGACTGAAAAGGGAATCATTTTTCACTGT   1259
1260 ACATTATAAACCTTCAGAAGAGCTATTTTTTTAAGCTATCAGCAATACTCATCAGAGCAGCT 1319
1320 AGCTCTTTGGTCTATTTTCTGCA      1342
```

STABLE PROTEIN: PHOSPHOLIPID COMPOSITIONS AND METHODS

This application is a continuation-in-part of application Ser. No. 08/361,011, filed Dec. 21, 1994, now abandoned, which in turn is a continuation of application Ser. No. 08/132,413, filed Oct. 6, 1993, now abandoned.

BACKGROUND OF THE INVENTION

The present invention relates to protein:phospholipid structures which are useful for stabilizing the secondary and tertiary structure of proteins capable of transitioning into the molten globular state. More particularly, this invention relates to G-CSF:phospholipid and MGDF:phospholipid compositions having increased stability, exhibiting increased shelf life, and capable of use in high temperature formulations and as novel delivery vehicles.

Several proteins have been shown to transition into a molten globular state (MGS). Van der Goot, F. G., *Nature* 354, 408–410 (1991). Proteins in the molten globular state exhibit secondary structure which is comparable to the native protein yet they lack rigid tertiary structure. Pitsyn et al., *FEBS Letters* 262:1, 20–24 (1990). In some cases, transition into this state is accompanied by exposure of previously hidden hydrophobic regions of the protein. By exposing critical hydrophobic residues, the MGS may be an intermediate in the aggregation and precipitation of proteins. The MGS conformation can be detected by comparing the circular dichroism in the far UV region with the spectra of aromatic side chains (near UV circular dichroism and fluorescence). The molten globular state exhibits aromatic group spectral changes in the absence of far UV circular dichroism changes, Bychkova et al., *FEBS Letters* 238: 231–234 (1988),and may be involved in membrane penetration by some proteins Bychkova et al., *FEBS Letters* 238: 231–234 (1988); Van der Goot, F. G., *Nature* 354, 408–410 (1991).

Granulocyte colony stimulating factor (G-CSF) is one protein known to transition into the MGS prior to aggregation. Human recombinant G-CSF selectively stimulates neutrophils, a type of white blood cell used for fighting infection. Currently, Filgrastim, a recombinant C-CSF, is available for therapeutic use. The structure of G-CSF under various conditions has been extensively studied; Lu et al.,*J. Biol. Chem. Vol.* 267, 8770–8777 (1992). Because of its hydrophobic characteristics, G-CSF is difficult to formulate for extended shelf life. Formulations of certain hydrophobic proteins lose activity due to formation of dimer and higher order aggregates (macro range) during long-term storage. Other chemical changes, such as deamidation and oxidation may also occur upon storage. In addition, the G-CSF formulator must protect against denaturation and, in particular, look to maintain the stability of the secondary and tertiary structure of the protein.

Human GM-CSF is a 22-kDa glycoprotein required continuously for the in vitro proliferation of macrophage and granulocytic progenitor cells. It also controls the irreversible commitment of these progenitors to form granulocytes and macrophages. Other biological activities may include regulation of the functional activity of mature cell types; Gough et al., *Nature*, 309, 763–767 (1984), and increasing chemotaxis towards recognized chemoattractants; Williams et al., *Hematology*, 4th ed. (1990). GM-CSF also stimulates the production of monocytes, and thus may be useful in the treatment of monocytic disorders, such as monocytopenia.

Human GM-CSF can be obtained and purified from a number of sources. Procedures for the production of recombinant human GM-CSF have been previously described by Burgess et al., *Blood*, 69:1, 43–51 (1987). U.S. Pat. No. 5,047,504 (Boone), incorporated herein by reference, has enabled the production of commercial scale quantities of GM-CSF in non-glycosylated form as a product of procaryotic host cell expression.

MGDF, or megakaryocyte growth and differentiation factor, is a recently cloned cytokine that appears to be the major regulator of circulating platelet levels. See Bartley, T. D. et al., *Cell* 77:1117–1124 (1994); Lok, S. et al., *Nature* 369:565–568 (1994); de Sauvage, F. J. et al., *Nature* 369:533–538 (1994); Miyazake, H. et al., *Exp. Hematol.* 22:838 (1994); and Kuter, D. J. et al., *PNAS USA*, 91:11104–11108 (1994). MGDF is also referred to as thrombopoietin (TPO), mpl-ligand, and megapoietin. Mature human MGDF is a protein having 332 amino acids in total. The sequence of this protein and the corresponding cDNA are shown in FIG. 29 herein.

Recombinant MGDF produced in both Chinese Hamster Ovary (CHO) and *E. coli* cells has been demonstrated to have a biological activity of specifically stimulating or increasing megakaryocytes and/or platelets in vivo in mice, rats and monkeys. See e.g., Hunt, P. et al., *Blood* 84(10) :390A (1994). Human MGDF molecules that have been truncated so that they extend at least 151 amino acids, starting from amino acid position 1 in FIG. 29, retain biological activity in vivo. It is also possible to remove up to the first six amino acids at the N-terminus of the human sequence MGDF protein and retain biological activity. Therefore, it appears that biological activity is retained within amino acids 7 to 151 (inclusive) of the mature amino acid sequence of human MGDF shown in FIG. 29.

Naturally occurring MGDF is a glycosylated molecule. The glycosylation pattern of natural MGDF is related to two key domains that have been found in MGDF. The sequence of the first approximately 151 amino acids of human MGDF, corresponding to an active portion of the molecule, bears notable homology to erythropoietin (EPO), a cytokine capable of stimulating production of erythrocytes, and is referred to as the "EPO-like" domain of human MGDF. The remaining amino acids of the mature protein make up a so-called "N-linked carbohydrate" domain, since they include most if not all of the sites for N-linked glycosylation. In human MGDF, there are six N-linked glycosylation sites all contained in the N-linked glycosylation domain. Both domains contain O-linked glycosylation sites. There are an estimated 12–14 O-linked glycosylation chains in the molecule. Experimental evidence with human MGDF DNA expressed recombinantly in CHO cells reveals that in the EPO-like domain at least two O-linked sites are glycosylated, at positions 1 (Ser) and 37 (Thr).

While proteins such as G-CSF and MGDF may be stabilized under certain defined conditions, there still exists a need to extend the shelf life of these and other proteins by stabilizing the secondary and tertiary structure of the proteins. One way which has been tried in the past to work with such proteins is the use of liposomes. Liposomes are completely closed lipid bilayer membranes formed by water-insoluble polar lipids, particularly phospholipids. Liposome vesicles may have a single membrane bilayer (unilamellar) or may have multiple membrane bilayers (multilamellar). The bilayer is composed of two lipid monolayers having a hydrophilic (polar) "head" region and a hydrophobic (nonpolar) "tail" region wherein the hydrophobic tails orient toward the center of the bilayer, whereas the hydrophilic heads orient toward the aqueous phase. The stability, rigidity, and permeability of liposomes can be altered by changes in the phospholipid composition, by changes in temperature, by inclusion of a sterol or by incorporation of a charged amphiphile. The basic structure of liposomes may be made by a variety of techniques known in the art.

In the process of their formation liposomes can entrap water solutes in the aqueous channels and release them at variable rates. Upon the discovery that liposomes can introduce enzymes into cells and alter their metabolism (Gregoriadis, *New Engl. J. Med.* 295, 704–710, 765–770 (1976)), liposomes were heralded as the answer to the quest for targeted drug delivery. As a result, there is a great deal of developmental research in the pharmaceutical industry involving use of liposomes as slow release depots for drugs, vitamins and proteins sequestered within the hydrophobic layers or hydrophobic core of the liposome.

Successful use of liposomes as drug-carriers has been limited because the researchers attempting such use have encountered several problems. For example, liposomes are known to act as powerful immunological adjuncts to entrapped antigens and caution must be exercised when enzymes or other proteins of xenogenic origin are entrapped in the liposomes. Also, the rate of diffusion of the drug is difficult to control. This is a function of the inherent instability of the liposomes and the presence of certain blood components which accelerate diffusion of certain drugs. In addition, by their nature, some substances are poorly entrapped in liposomes and therefore diffuse rapidly in circulation. Finally, there has been a problem targeting any cells or organ other than the liver or spleen. An excellent review of liposomes, substances which have been incorporated into liposomes, and the problems associated with use of liposomes as drug carriers is "Liposomes" by Gregory Gregoriaidis, found in *Drug Carriers in Biology and Medicine*, Chapter 14, 287–341 (Academic Press, N.Y., 1979).

While much has been reported concerning attempts to use liposomes as drug carriers, little has been disclosed concerning the use of liposomes for purposes of increasing shelf life of therapeutic peptides or proteins by stabilizing the structure of the peptide and/or protein. In PCT/US90/05163, entitled, "Therapeutic Peptides and Proteins", Hostetler, et al. disclose use of empty liposomes as a pharmaceutically acceptable diluent to solubilize polypeptides and/or proteins in order to prevent accumulation of the polypeptides and/or proteins at an air/water interface, and to prevent adsorption of the polypeptides and/or proteins to container surfaces. Hostetler et al. disclose that negatively charged phospholipid may be added up to about 50 mole percent, and that phosphatidylcholine, a neutral phospholipid, is the preferred liposome. Hostetler et al. do not disclose a diluent shown to stabilize the structure of a polypeptide and/or protein.

In PCT/US91/07694, entitled, "Preparation and Characterization of Liposomal Formulations of Tumor Necrosis Factor", Hung et al., a lipophilic modified tumor necrosis factor (TNF) molecule in association with the surface or encapsulated within a liposome is described. The liposomal lipophilic TNF molecules are reported to have enhanced in vivo stability. Stability referred to a decrease or a decreased tendency of the TNF-liposome to leak TNF into the system in vivo. The preferred liposomes were neutral lipids. Hung et al. do not disclose a TNF composition wherein the excipients have a stabilizing effect on the structure of the protein.

Nothing can be drawn from the literature concerning contacting a protein, e.g. G-CSF or MGDF, with a negatively charged lipid vesicle thereby directly stabilizing the protein against thermally-induced aggregation, denaturation, loss of activity, and unfolding of the secondary structure. The need exists for such compositions which provide the benefit of being useful in formulation procedures requiring high temperatures (e.g. incorporation of G-CSF and/or MGDF into polymers) as well as being used as novel delivery vehicles (e.g. oral administration of pegylated G-CSF). The present invention provides such compositions.

SUMMARY OF THE INVENTION

The present invention is directed to the addition of hydrophobic excipients, e.g. lyso-phospholipids or other liposomes, to a protein under molten globular state conditions will directly stabilize the secondary and tertiary structure of the protein, thereby protecting the protein against thermally-induced aggregation, denaturation, and loss of activity. In particular, the invention is directed to stable G-CSF:phospholipid and MGDF:phospholipid compositions. Surprisingly, the preferred G-CSF:phospholipid and MDGF:phospholipid compositions can be cycled several times between 10°–95° C. with full recovery of protein secondary structure upon cooling. The compositions are useful for formulation procedures requiring high temperatures, as well as for use as novel delivery vehicles. In addition, the compositions exhibit a prolonged shelf-life as compared to protein alone, and the interaction of protein with phospholipid vesicle prevents adsorption of protein to glass vials.

In a preferred embodiment, the protein:phospholipid complex comprises a negatively charged liposome which is selected from dioleoylphosphatidylglycerol (DOPG), dimyristoylphosphatidylglycerol (DMPG), dipalmitoylphosphatidylglycerol (DPPG), eggphosphatidylglycerol, dioleoylphosphatidylethanolamine (DOPE), eggphosphatidylethanolamine, dioleoylphosphatidic acid (DOPA), dimyristoylphosphatidic acid (DMPA), dipalmitoylphosphatidic acid (DPPA), dioleoylphosphatidylserine (DOPS), dimyristoylphosphatidylserine (DMPS), dipalmitoylphosphatidylserine (DPPS), eggphosphatidylserine, lysophosphatidylglycerol, lysophosphatidylethanolamine, lysophosphatidylserine. DOPG, a negatively charged, unsaturated phospholipid is especially preferred. The invention further comprises a pH maintained in the range of 3.0–7.5, and a lipid:protein ratio of at least 10:1.

Additional elements that provide preferred embodiments of the invention include use of chemically modified proteins in the protein:phospholipid complex as well as use of one or more of the following: an isotonicity adjusting agent; a buffering agent; and a pH adjusting agent. As would be understood by a person having knowledge of the art, the invention encompasses stable protein:phospholipid compositions having various combinations of these additional elements.

BRIEF DESCRIPTION OF THE DRAWINGS

FIG. 2(a) shows $F/F_0$ (■) and maximum emission wavelengths (Δ) for mixtures of DOPG:rhG-CSF. FIG. 2(b) shows $F/F_0$ (■) and maximum emission wavelengths (Δ) for mixtures of DOPC:rhG-CSF.

FIGS. 19A–19B shows: (a) the effect of temperature cycling on the CD of GM-CSF in PBS, pH 7.0. GM-CSF at 10° C. (—) is compared to GM-CSF which was heated to 90° C. and then cooled to 10° C. (---); (b) the effect of temperature cycling on the CD of DPPG:PEG-G-CSF (17:1 molar). DPPG:GM-CSF at 100° C. (—) is compared to DPPG:GM-CSF which was heated to 90° C. and then cooled to 10° C. (---).

FIGS. 20A–20B shows: (a) the results of the total WBC response to intraduodenal infusion of rhG-CSF in the absence and presence of DOPG. The rhG-CSF dose was 750 μg/kg and the lipid:protein ratio was 100:1; (b) the results of the total WBC response to intraduodenal infusion of PEG-G-CSF in the absence and presence of DOPG. The PEG-G-CSF dose was 750 μg/kg and the lipid:protein ratio was 100:1.

FIG. 21 shows the effect of DOPG on serum levels of PEG-G-CSF after intraduodenal pump infusion. The PEG-G-CSF dose was 750 μg/kg and the lipid:protein ratio was 100:1.

FIG. 22 depicts the fluorescence emission spectrum of MGDF in the presence and absence of DMPG vesicles. The concentration of the MGDF was 0.1 mg/ml. The MGDF was E. coli derived MGDF 1-163. The DMPG:MGDF ratio was 100:1 (mole:mole).

FIG. 23 shows the effect of increasing lipid:protein ratio on the MGDF fluorescence. The MGDF was E. coli derived MGDF 1-163. Maximum emission wavelengths for mixtures of DMPG:MGDF at pH 5.0 (-○-) and pH 7.0 (-●-) are depicted.

FIG. 29 shows the DNA and amino acid sequence of human MGDF (SEQ ID NOS:1 and 2 including a signal peptide (amino acids −21 to −1) and the mature amino acid sequence (1–332).

DETAILED DESCRIPTION

Figure 1:
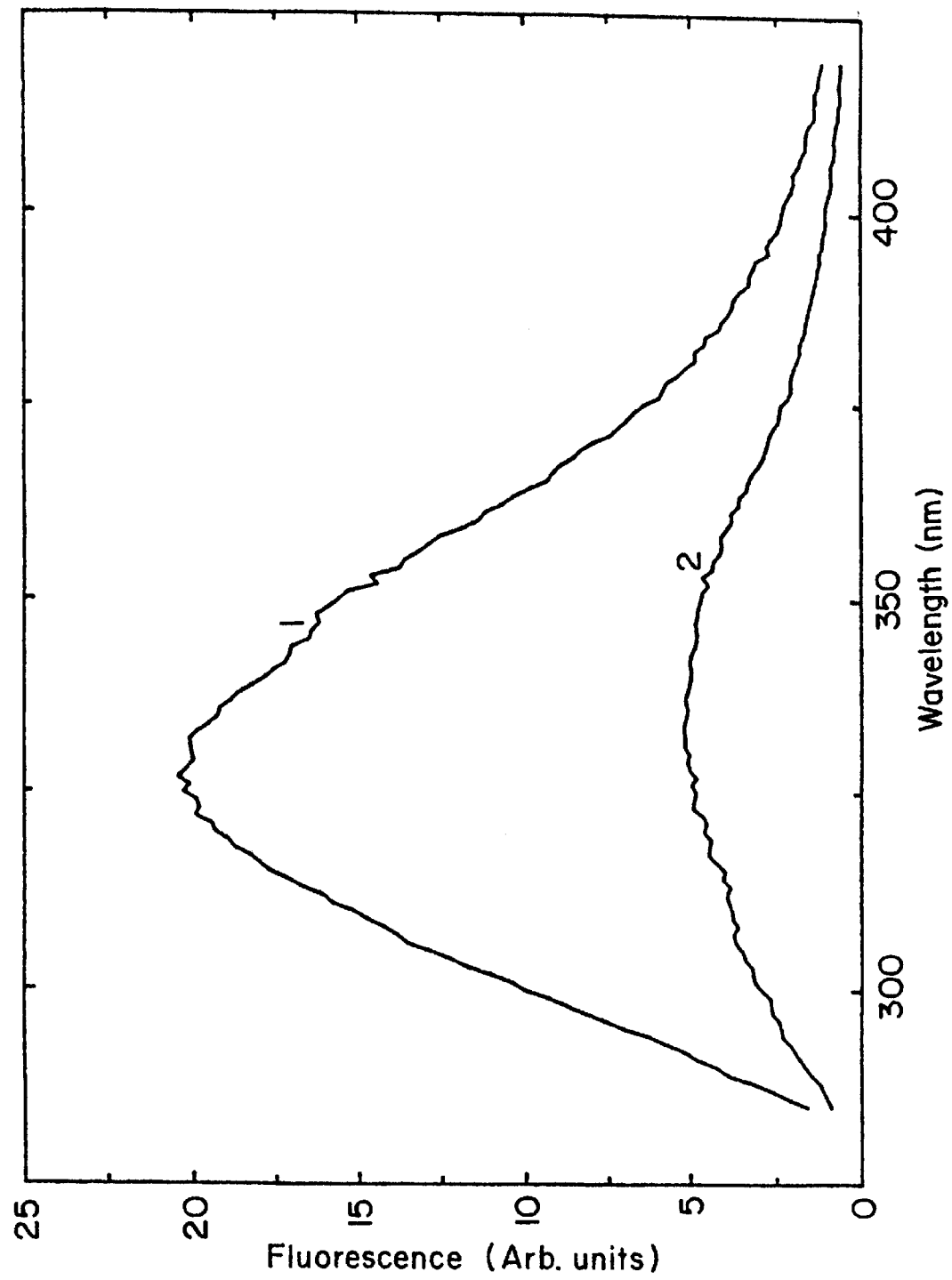
FIG. 1 depicts the fluorescence emission spectrum of rhG-CSF in the presence (curve 1) and absence (curve 2) of DOPG vesicles. The concentration of the rhG-CSF was 0.2 mg/ml. The DOPG:rhG-CSF ratio (curve 1) was 100:1 (mole:mole).

The compositions of the present invention are described in more detail in the discussion that follows and are illustrated by the examples provided below. The examples show various aspects of the invention and include results of stability and biological activity testing of various protein-:phospholipid compositions. Surprisingly, the interaction of the proteins with the lipid vesicle directly stabilized the protein structure of the protein, thereby exerting a stabilizing effect on the protein even under conditions which lead to denaturation of the protein in the absence of lipid.

The oral administration of a chemically modified G-CSF:phospholipid composition is also described herein, using G-CSF (as described above) to which polyethylene glycol molecules have been attached.

Contemplated for use in the practice of the present invention are a variety of proteins capable of transitioning into the molten globular state. Exemplary proteins contemplated are cytokines, including various hematopoietic factors such as the aforementioned G-CSF, GM-CSF, MGDF, M-CSF, the interferons (alpha, beta, and gamma), the interleukins (1–11), erythropoietin (EPO), fibroblast growth factor, stem cell factor, nerve growth factor, BDNF, NT3, platelet-derived growth factor, and tumor growth factor (alpha, beta). Other proteins may be evaluated for the ability to transition into the MGS. If the protein in question is capable of transitioning into the MGS, the protein in question may then be contacted with a negatively charged liposome vesicle and the stabilizing effects evaluated.

In general, G-CSF useful in the practice of this invention may be a native form isolated pure from mammalian organisms or, alternatively, a product of chemical synthetic procedures or of procaryotic or eucaryotic host expression of exogenous DNA sequences obtained by genomic or cDNA cloning or by gene synthesis. Suitable procaryotic hosts include various bacterial (e.g., E. coli) cells. Suitable eucaryotic hosts include yeast (e.g., S. cerevisiae) and mammalian (e.g., Chinese hamster ovary, monkey) cells. Depending upon the host employed, the G-CSF expression product may be glycosylated with mammalian or other eucaryotic carbohydrates, or it may be non-glycosylated. The present invention contemplates the use of any and all such forms of G-CSF, although recombinant G-CSF, especially E. coli derived, is preferred for reasons of greatest commercial practicality.

The G-CSF to be chemically modified for use in the present invention may also be either natural human G-CSF (nhG-CSF) or the product of a recombinant nucleic acid process, such as prokaryotic or eukaryotic host cell expression. In general, chemical modification contemplated is the attachment of a chemical moiety to the G-CSF molecule itself. A review article describing protein modification and fusion proteins is Francis, *Focus on Growth Factors* 3: 4–10 (May 1992)(published by Mediscript, Mountview Court, Friern Barnet Lane, London N20 OLD, UK). For example, see EP 0 401 384, entitled, "Chemically Modified Granulocyte Colony Stimulating Factor," which describes materials and methods for preparing G-CSF to which polyethylene glycol molecules are attached. The attachment may be by bonding, directly to the protein or to a moiety which acts as a bridge to the active agent. Covalent bonding is preferred as the most stable for attachment. The chemical modification may contribute to the controlled, sustained or extended effect of the G-CSF. This may have the effect, for example, of controlling the amount of time the chemically modified G-CSF takes to reach the circulation. An example of a chemical modifier is polyethylene glycol compositions, including derivatives thereof.

Contemplated for use in the practice of this invention are any chemically modified G-CSF preparations which permit efficacy upon administration. Efficacy may be determined by known methods, as a practitioner in the art will recognize. Pegylated G-CSF, especially pegylated E. coli derived G-CSF, and more particularly, tri-tetra pegylated E. coli derived G-CSF is preferred.

G-CSF has been reported to be most stable under acidic conditions, despite the fact that in the pH range of 2.5–5.0, a conformational change occurs which involves a loosening of the tertiary structure and an increase in alpha helical content. Narhi et al., *J. Protein Chem.* 10, 359–367, (1991). This conformational change is characteristic of the molten globular state (MGS). Thus, as is the case for a formulator working with other proteins capable of transitioning into the MGS, a formulator working with G-CSF must protect against thermally-induced unfolding of secondary and tertiary structure in order to prevent aggregation and denaturation.

The GM-CSF useful in the present invention may be a native form isolated pure from mammalian organisms or a product of procaryotic or eucaryotic host expression of exogenous DNA sequences obtained by genomic or cDNA cloning or by gene synthesis. Suitable procaryotic hosts include various bacterial (e.g., E. coli) cells. Suitable eucaryotic hosts include yeast (e.g., S. cerevisiae) and mammalian (e.g., Chinese hamster ovary, monkey) cells. Depending upon the host employed, the GM-CSF expression product may be glycosylated with mammalian or other eucaryotic carbohydrates, or it may be non-glycosylated. The present invention contemplates the use of any and all such forms of GM-CSF, although recombinant GM-CSF, especially E. coli derived, is preferred for reasons of greatest commercial practicality.

The term "MGDF", as used herein, includes naturally occurring MGDF, truncations of naturally occurring MGDF as well as non-naturally occurring polypeptides having an amino acid sequence and glycosylation sufficiently duplicative of that of naturally occurring MGDF to allow possession of a biological activity of specifically stimulating growth, development and/or production of megakaryocytes and/or platelets.

In a preferred embodiment, MGDF is the product of the expression of an exogenous DNA sequence that has been transfected into a eukaryotic or procaryotic host cell; that is, in a preferred embodiment the MGDF is "recombinant MGDF". The preferred eucaryotic host is mammalian, particularly preferably CHO cells, and the preferred procaryotic host is bacteria, particularly preferably *E. coli*. Recombinant MGDF is advantageously produced according to the procedures described herein and in the publications cited herein regarding cloning and expression of MGDF.

Some additional preferred MGDF molecules have the following amino acid sequences, based on FIG. 29 herein:

MGDF 1-332 amino acids 1–332 of FIG. 29
MGDF 1-191 amino acids 1–191 of FIG. 29
MGDF 1-183 amino acids 1–183 of FIG. 29
MGDF 1-174 amino acids 1–174 of FIG. 29
MGDF 1-163 amino acids 1–163 of FIG. 29
MGDF 1-153 amino acids 1–153 of FIG. 29
MGDF 1-152 amino acids 1–152 of FIG. 29
MGDF 1-151 amino acids 1–151 of FIG. 29
MGDF 7-332 amino acids 7–332 of FIG. 29
MGDF 7-191 amino acids 7–191 of FIG. 29
MGDF 7-183 amino acids 7–183 of FIG. 29
MGDF 7-174 amino acids 7–174 of FIG. 29
MGDF 7-163 amino acids 7–163 of FIG. 29
MGDF 7-153 amino acids 7–153 of FIG. 29
MGDF 7-152 amino acids 7–152 of FIG. 29
MGDF 7-151 amino acids 7–151 of FIG. 29

In each of the above cases, Met-Lys may further be included in the N-terminus thereof.

Also contemplated for use in the present invention are various analogs of MGDF. As used herein the phrase "analog of MGDF" refers to MGDF with one or more changes in the amino acid sequence of MGDF which result in a change in the type (N- or O-linked), number, or location of sites for carbohydrate attachment. The MGDF analog(s) retain(s) at least equivalent biological activity as compared to natural sequence MGDF (e.g., human MGDF) and may possess substantially higher activity, as measured in assays for biological activity. The resulting analogs may have fewer or more (preferably more) carbohydrate chains than natural human/recombinant MGDF.

Also included within the analogs of this invention are analogs which have one or more amino acids extending from the carboxy terminal end of MGDF wherein the carboxy terminal extension provides at least one additional carbohydrate site. The carboxy terminus of MGDF will vary depending upon the particular form of MGDF used (e.g., MGDF 1-332 amino acids, or MGDF 1-163 amino acids). An additional carbohydrate site may be added to the carboxy terminus of an MGDF species by adding amino acids to the carboxy terminus, such amino acids containing one or more N- or O-linked glycosylation sites.

The present invention also broadly includes chemically modified MGDF compositions. In general, the chemical modification contemplated is an MGDF product wherein said MGDF protein is linked to at least one polyethylene glycol molecule (i.e., pegylated MGDF). Pegylation of MGDF may be carried out by any of the pegylation reactions known in the art. See, for example: *Focus on Growth Factors* 3(2): 4–10 (1992); EP 0 154 316; EP 0 401 384; and the other publications cited herein that relate to pegylation. Preferably, the pegylation is carried out via an acylation reaction or an alkylation reaction with a reactive polyethylene glycol molecule (or an analogous reactive water-soluble polymer).

Pegylation by acylation generally involves reacting an active ester derivative of polyethylene glycol (PEG) with an MGDF protein. Any known or subsequently discovered reactive PEG molecule may be used to carry out the pegylation of MGDF. A preferred activated PEG ester is PEG esterified to N-hydroxysuccinimide ("NHS"). As used herein, "lacylation" is contemplated to include without limitation the following types of linkages between MGDF and a water soluble polymer such as PEG: amide, carbamate, urethane, and the like. See Bioconjugate Chem. 5:133–140 (1994). Reaction conditions may be selected from any of those known in the pegylation art or those subsequently developed, but should avoid conditions such as temperature, solvent, and pH that would inactivate the MGDF species to be modified.

Pegylation by acylation will generally result in a poly-pegylated MGDF product, wherein the lysine ε-amino groups are pegylated via an acyl linking group. Preferably, the connecting linkage will be an amide. Also preferably, the resulting product will be substantially only (e.g., ≧95%) mono, di- or tri-pegylated. However, some species with higher degrees of pegylation (up to the maximum number of lysine ε-amino acid groups of MGDF plus one α-amino group at the amino terminus of MGDF) will normally be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Figure 30:
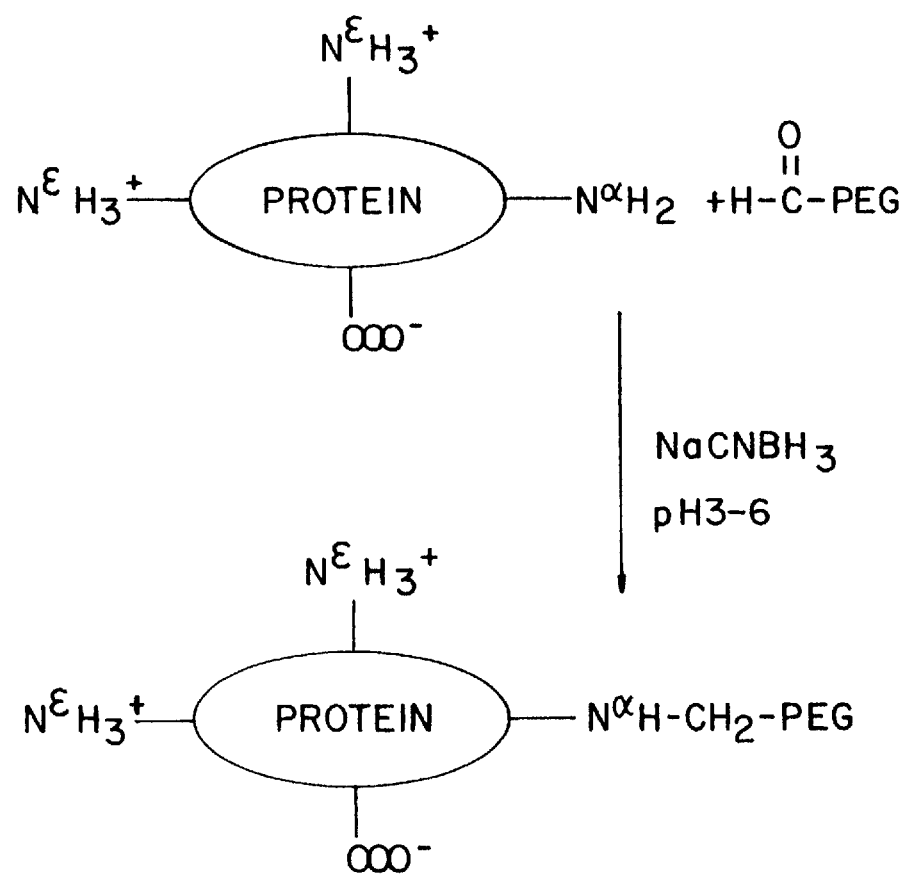
FIG. 30 shows an example of site-specific MGDF reductive alkylation at the α-amino group of the N-terminal residue using mono-methoxy-polyethylene glycol aldehydes to result in a substantially mono-pegylated product.

Pegylation by alkylation generally involves reacting a terminal aldehyde derivative of PEG with a protein such as MGDF in the presence of a reducing agent. Pegylation by alkylation can also result in poly-pegylated MGDF. In addition, one can manipulate the reaction conditions as described herein to favor pegylation substantially only at the α-amino group of the N-terminus of the MGDF species (i.e., a mono-pegylated species). An exemplary reductive alkylation reaction with MGDF to yield a monopegylated product is shown in FIG. 30. In either case of monopegylation or polypegylation, the PEG groups are preferably attached to the protein via a —$CH_2$—NH— group. With particular reference to the —$CH_2$— group, this type of linkage is referred to herein as an "alkyl" linkage.

Derivatization via reductive alkylation to produce a monopegylated product exploits differential reactivity of different types of primary amino groups (lysine versus the N-terminal) available for derivatization in MGDF. The reaction is performed at a pH (see below) which allows one to take advantage of the $pK_a$ differences between the ε-amino groups of the lysine residues and that of the α-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs.

Thus, in a preferred aspect, the present invention relates to pegylated MGDF, wherein the PEG group(s) is (are) attached via acyl or alkyl groups. As discussed above, such products may be mono-pegylated or poly-pegylated (e.g., containing 2–6, preferably 2–5, PEG groups). The PEG groups are generally attached to the protein at the α or ε amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers or a mixture thereof. The polymer selected should be water soluble so that the protein to which it is attached does not precipitate in an aqueous environment, such as a physiological environment. The polymer selected should be modified to have a single reactive group, such as an active ester for acylation or an aldehyde for alkylation, preferably, so that the degree of polymerization may be controlled as provided for in the present methods. A preferred reactive PEG aldehyde is polyethylene glycol propionaldehyde, which is water stable, or mono C1–C10 alkoxy or aryloxy derivatives thereof (see, U.S. Pat. No. 5,252,714). The polymer may be branched or unbranched. Preferably, for therapeutic use of the end-product preparation, the polymer will be pharmaceutically acceptable. The water soluble polymer may be selected from the group consisting of, for example, polyethylene glycol, monomethoxy-polyethylene glycol, dextran, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. For the acylation reactions, the polymer (s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1-C1O) alkoxy- or aryloxy-polyethylene glycol. Methods for preparing pegylated MGDF will generally comprise the steps of (a) reacting an MGDF polypeptide with polyethylene glycol (such as a reactive ester or aldehyde derivative of PEG) under conditions whereby MGDF becomes attached to one or more PEG groups, and (b) obtaining the reaction product(s). In general, the optimal reaction conditions for the acylation reactions will be determined case-by-case based on known parameters and the desired result. For example, the larger the ratio of PEG: protein, the greater the percentage of poly-pegylated product.

Another important consideration is the molecular weight of the polymer. In general, the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa (the term "about" indicating ±1 kDa). The preferred average molecular weight is about 5 kDa to about 50 kDa, particularly preferably about 12 kDa to about 25 kDa, and most preferably 20 kDa. The ratio of water-soluble polymer to MGDF protein will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any MGDF protein having an α-amino group at the amino terminus, and provide for a substantially homogenous preparation of monopolymer/MGDF protein conjugate. The term "monopolymer/MGDF protein conjugate" is used here to mean a composition comprised of a single polymer molecule attached to an MGDF protein molecule. The monopolymer/MGDF protein conjugate preferably will have a polymer molecule located at the N-terminus, but not on lysine amino side groups. The preparation will preferably be greater than 90% monopolymer/MGDF protein conjugate, and more preferably greater than 95% monopolymer MGDF protein conjugate, with the remainder of observable molecules being unreacted (i.e., protein lacking the polymer moiety). The examples below provide for a preparation which is at least about 90% monopolymer/protein conjugate, and about 10% unreacted protein. The monopolymer/protein conjugate has biological activity.

The lipid vesicles useful in the compositions of the present invention are those negatively charged liposomes capable of interacting with the protein in question. Particular liposomes contemplated for use include dioleoylphosphatidylglycerol (DOPG), dimyristoylphosphatidylglycerol (DMPG), dipalmitoylphosphatidylglycerol (DPPG), eggphosphatidylglycerol, dioleoylphosphatidylethanolamine (DOPE), eggphosphatidylethanolamine, dioleoylphosphatidic acid (DOPA), dimyristoylphosphatidic acid (DMPA), dipalmitoylphosphatidic acid (DPPA), dioleoylphosphatidylserine (DOPS), dimyristoylphosphatidylserine (DMPS), dipalmitoylphosphatidylserine (DPPS), eggphosphatidylserine, lysophosphatidylglycerol, lysophosphatidylethanolamine, lysophosphatidylserine. Depending on the particular liposome utilized, the amount of liposome could vary.

The protein:phospholipid compositions preferably include a buffering agent to maintain the pH of the solution within a desired range. Preferred agents include sodium acetate, sodium phosphate, and sodium citrate. Mixtures of these buffering agents may also be used. The amount of buffering agent useful in the composition depends largely on the particular buffer used and the pH of the solution. For example, acetate is a more efficient buffer at pH 5 than pH 6 so less acetate may be used in a solution at pH 5 than at pH 6. The preferred pH range for the compositions of the present invention is pH 3.0–7.5.

The compositions of the present invention may further include an isotonicity adjusting agent to render the solution isotonic and more compatible for injection. The most preferred agent is sodium chloride within a concentration range of 0–150 mM.

Also comprehended by the invention are pharmaceutical compositions comprising effective amounts of polypeptide products of the invention together with pharmaceutically acceptable diluents, preservatives, solubilizers, emulsifiers, adjuvants and/or carriers. Such compositions will influence the physical state, stability, and bioavailability of the protein. See, e.g., *Remingtons Pharmaceutical Sciences*, 18th Edition, 1435–1712 (Mack Publishing Co., Easton, Pa., 1990) which is herein incorporated by reference. What constitutes an effective amount of the protein in a particular case will depend on a variety of factors which the knowledgeable practitioner will take into account, including the desired therapeutic result, the severity of the condition or illness being treated, the physical condition of the subject, and so forth.

In a preferred embodiment involving *E. coli* derived rhG-CSF, the liposome vesicle used is DOPG with a 50:1 ratio of DOPG:G-CSF, at pH 4.5, containing 10 mM sodium acetate.

In a preferred embodiment involving E. coli derived rhGM-CSF, the liposome vesicle used is DMPG with a 17:1 ratio of DMPG:GM-CSF, at pH 7.0, in phosphate buffered saline (PBS).

In a preferred embodiment involving E. coli derived rhG-CSF which has been chemically modified (pegylated), the rhG-CSF is tri-tetra pegylated, the liposome vesicle used is DMPG with a 17:1 ratio of DMPG:PEG-G-CSF, at pH 4.5.

In a preferred embodiment involving E. coli derived MGDF 1-163, the liposome vesicle used is DMPG with a 100:1 ratio of DMPG:MGDF, at pH 5.0, in 10 mM sodium acetate 5% sorbitol.

In a preferred embodiment involving E. coli derived MGDF 1-163 which has been chemically modified (pegylated), the MGDF is mono-pegylated (20 kDa) via reductive alkylation, the liposome vesicle used is DMPG with a 100:1 ratio of DMPG:MGDF, at pH 5.0, in 10 mM sodium acetate 5% sorbitol.

In a preferred embodiment involving CHO derived MGDF 1–332, the liposome vesicle used is DMPG with a 100:1 ratio of DMPG:MGDF, at pH 5.0, in 10 mM sodium acetate 5% sorbitol.

Although the invention has been described and illustrated with respect to specific protein:lipid compositions and treatment methods, it will be apparent to one of ordinary skill that a variety of related compositions, and treatment methods may exist without departing from the scope of the invention.

The following examples will illustrate in more detail the various aspects of the present invention.

EXAMPLE 1

Initial experiments were performed to examine the possibility of incorporating recombinant human G-CSF (rhG-CSF) into a lipid vesicle. The rhG-CSF was produced using recombinant DNA technology in which E. coli cells were transfected with a DNA sequence encoding human G-CSF as described in U.S. Pat. No. 4,810,643 to Souza. The rhG-CSF was prepared as a 4 mg/ml solution in dilute HCl, pH 4.0. All lipids were obtained from Avanti Polar Lipids (Alabaster, Ala.) and were stored at −20° C. under nitrogen at a final concentration of 100 mg/ml in chloroform.

Preparation of G-CSF:Phospholipid Comolexes

To prepare lipid vesicles for combination with G-CSF, 30 $\mu$mole of the appropriate lipid was dispensed into a glass tube and dried to a thin film using a stream of nitrogen gas. The lipid films were desiccated for at least two hours under vacuum to remove any traces of chloroform. The lipid films were hydrated in 1 ml of either distilled de-ionized water (ddH$_2$O), phosphate buffered saline, pH 7.2 (Gibco/BRL "D-PBS") or 150 mM NaCl. The samples were then sonicated in a bath-type sonicator (Laboratory Supplies, Hicksville, N.Y.). Sonication was continued until the samples were optically clear (usually between 10–15 minutes). The samples were stored at 4° C. under nitrogen until use. The final lipid concentration was 30 mM. Alternatively, the lipid vesicles could be prepared by taking 300 $\mu$mole of lipid and drying under nitrogen and dessicating as described above. The dry lipid films were hydrated in 10 ml of appropriate aqueous solution as described above. The samples were then microfluidized in a bench scale emulsifier (Microfluidics Model 110S, Microfluidics, Inc. Cambridge, Mass.) operating at 10,000 psi. The samples were recycled through the instrument for 10 cycles. The microfluidized samples were then stored at 4° C. as described above.

The G-CSF:phospholipid complexes were prepared by mixing G-CSF (as described above) with a particular lipid (as described above). Mixing was accomplished by vortexing, stirring, or gentle shaking. Various mole ratios of lipid:G-CSF were prepared to evaluate membrane insertion and stabilization of protein. For example, to prepare a 3 ml sample (in water) which is 0.2 mg/ml G-CSF at a 40:1 mole ratio of lipid:G-CSF, 150 $\mu$l of G-CSF stock is combined with 44 $\mu$l of lipid (30 mM stock, prepared in water by sonication) and water is added to achieve a final sample volume of 3 ml. A five minute incubation is recommended (but not necessary), and was used here before using or assaying the sample.

G-CSF can also be combined with the hydrated lipid prior to microfluidization. Subsequent microfluidization of the mixtures as described above leads to incorporation of G-CSF into the lipid membrane.

Analysis of the G-CSF: Phospholipid Complexes
1. Tryptophan emission spectra.

There are two tryptophan residues in rhG-CSF that are quite sensitive to local environmental conditions. Therefore, analysis was performed to determine the rhG-CSF tryptophan fluorescence when the rhG-CSF is contacted with a liposome. A blue shift in fluorescence emission maximum would suggest that the tryptophans are in a more hydrophobic environment and therefore the rhG-CSF was embedded in the lipid membranes. An excellent review of tryptophan fluorescence analysis is *Principles of Fluorescence Microscopy*, by J. Lakowicz, Chap 11 (Plenum Press, New York, 1983).

Tryptophan fluorescence of the G-CSF:lipid complexes (as described above) was assayed by exciting the samples at 280 nm and while scanning the emission from 285 nm to 420 nm in 1 nm increments at a rate of 1 nm/sec. The sample volume was 3 ml and the final concentration of G-CSF was 0.2 mg/ml for all samples. The lipid:G-CSF ratios varied. All fluorescence measurements were carried out using a PTI Alphascan fluorometer (South Brunswick, N.J.). All measurements were performed at 25° C. and this temperature was maintained through the use of a water-jacketed cuvette holder connected to a circulating water bath. Emission spectra were collected and analyzed using the data software provided by PTI.

Figure 2A:
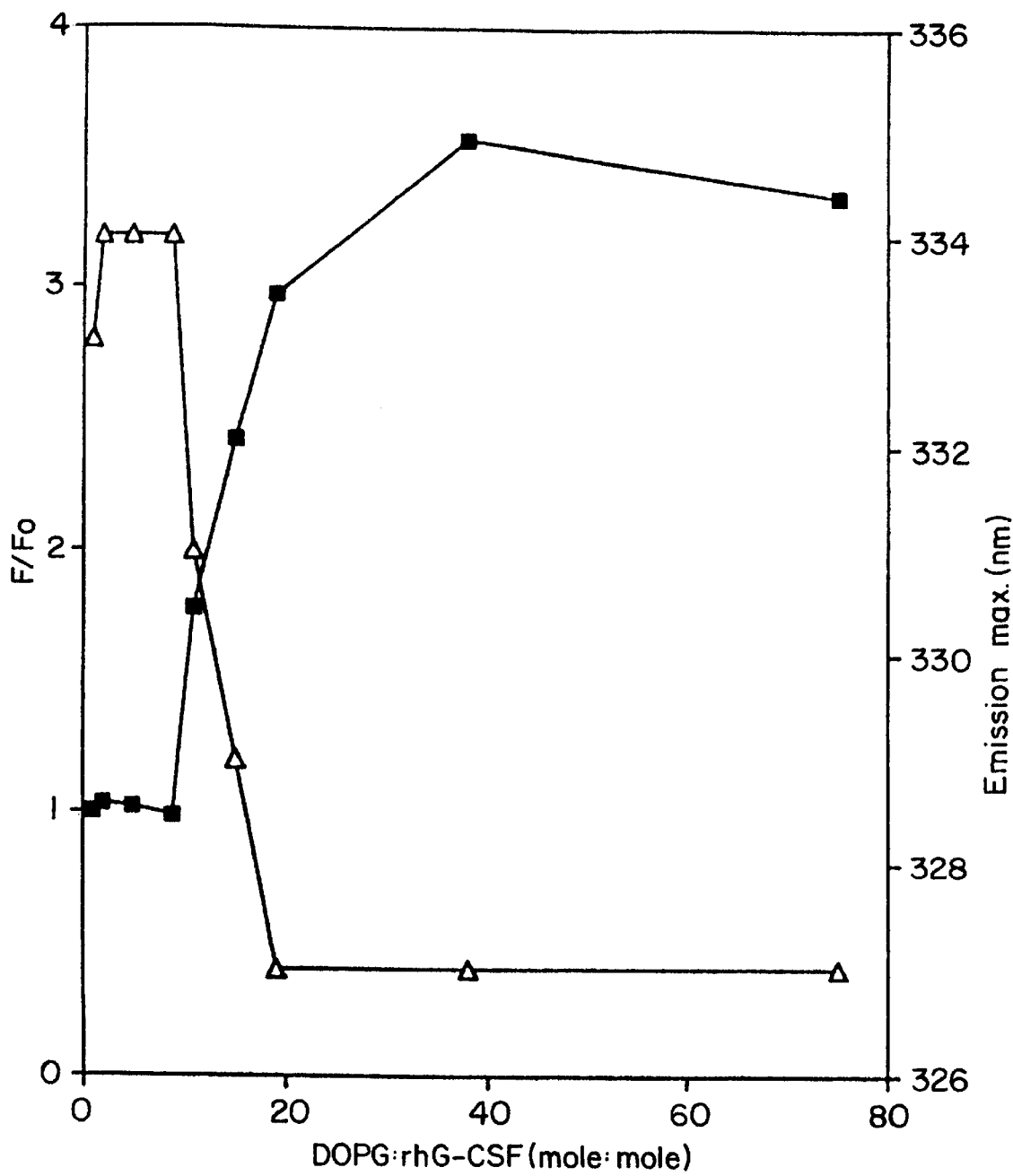
FIGS. 2A–2B shows the effect of increasing lipid:protein ratio on the rhG-CSF fluorescence. $F_0$ is the initial fluorescence (no lipid) and F refers to the fluorescence after addition of lipid to achieve the indicated molar ratio of lipid:rhG-CSF.
Figure 2B:
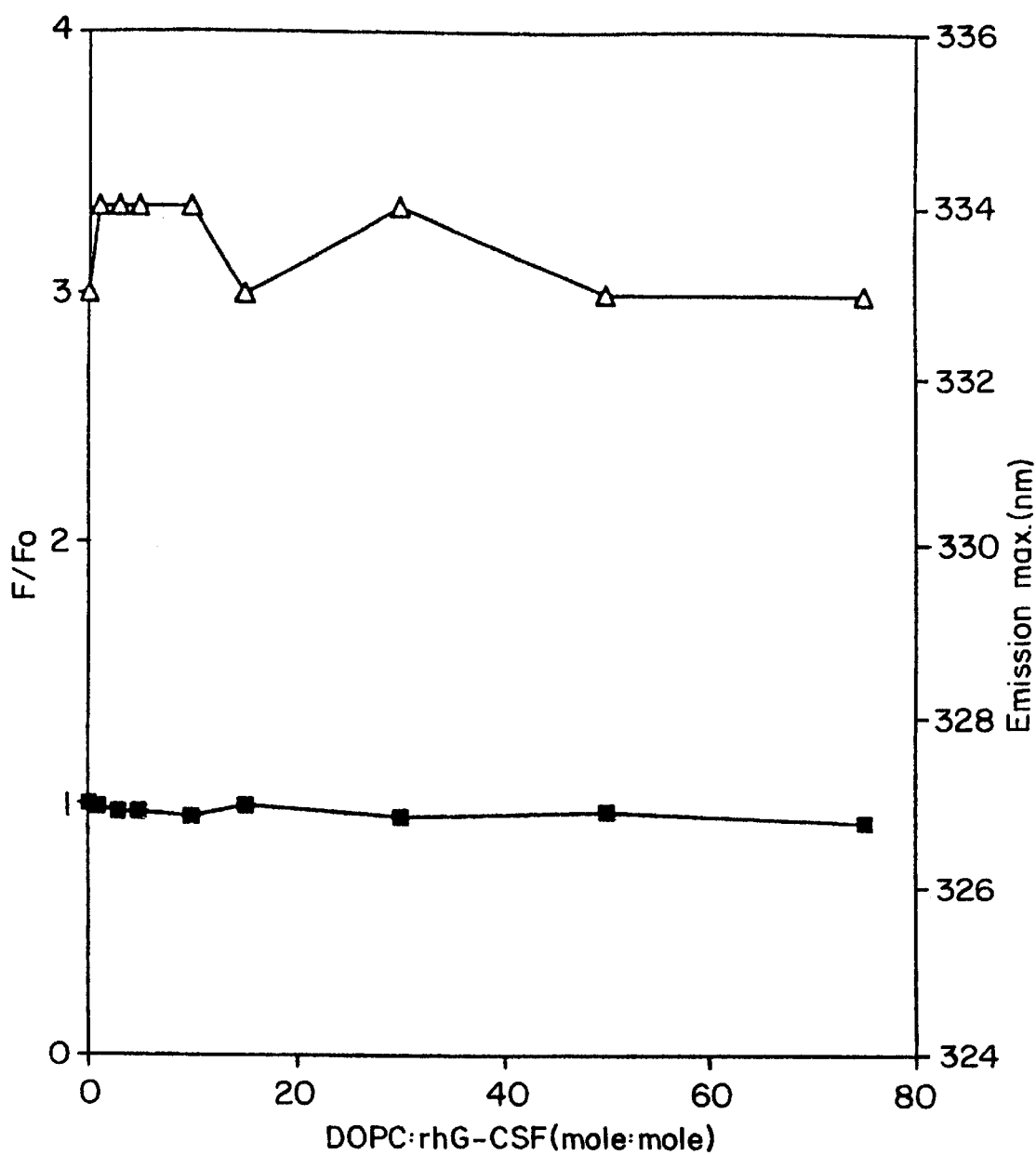

The fluorescence spectra of rhG-CSF in the presence and absence of small unilamellar vesicles composed of DOPG is shown in FIG. 1. rhG-CSF has an emission maximum at 334 nm in the absence of DOPG vesicles. In the presence of DOPG at a 100:1 lipid:protein ratio, rhG-CSF tryptophan fluorescence exhibits a blue shift in fluorescence emission maximum to 327 nm and a dramatic increase in fluorescence intensity. The low wavelength of the fluorescence emission in the presence of DOPG suggests that the tryptophans are in an environment more hydrophobic than the native protein. As demonstrated in FIG. 2, the fluorescence shifts depend on the mole ratio of DOPG:G-CSF and membrane insertion is detectable once a 10:1 ratio of DOPG:G-CSF is reached.

2. Iodide quenching experiments.

Iodide is an efficient collisional quencher of tryptophan fluorescence, but cannot penetrate lipid membranes. Therefore, efficient quenching of tryptophan fluorescence by iodide indicates exposure of the residues to the bulk aqueous solvent while protection from iodide quenching occurs when protein tryptophans are sequestered away from the aqueous solvent. In these experiments, G-CSF and a DOPG:G-CSF composition (100:1 lipid:protein ratio) was used. After initial readings ($F_o$) on the samples were taken and recorded, fluorescence intensity was measured after addition of increasing amounts of potassium iodide (KI)(5M stock). Both the sample and KI solutions were prepared to contain 1 mM $Na_2SO_3$ (final concentration) as described by Lee et al, *Biochem. Biophys. Acta*, 984: 174–182 (1989) and Le Doan et al., *Biochem. Biophys. Acta*, 858: 1–5 (1986). The addition of $Na_2SO_3$ prevents the formation of $I_2$ which can partition into nonpolar regions of proteins and membranes. The data were analyzed by the Stern-Volmer equation ($F_0/F=1+K_{KI}[KI]$), where $F_0$ and F are the fluorescence intensities of samples in the absence and presence, respectively, of KI at concentration [KI]. $K_{KI}$ is the Stern-Volmer quenching constant for KI quenching of G-CSF tryptophan residues; Lehrer, S., *Biochemistry* 10: 3254–3263 (1979).

Figure 3:
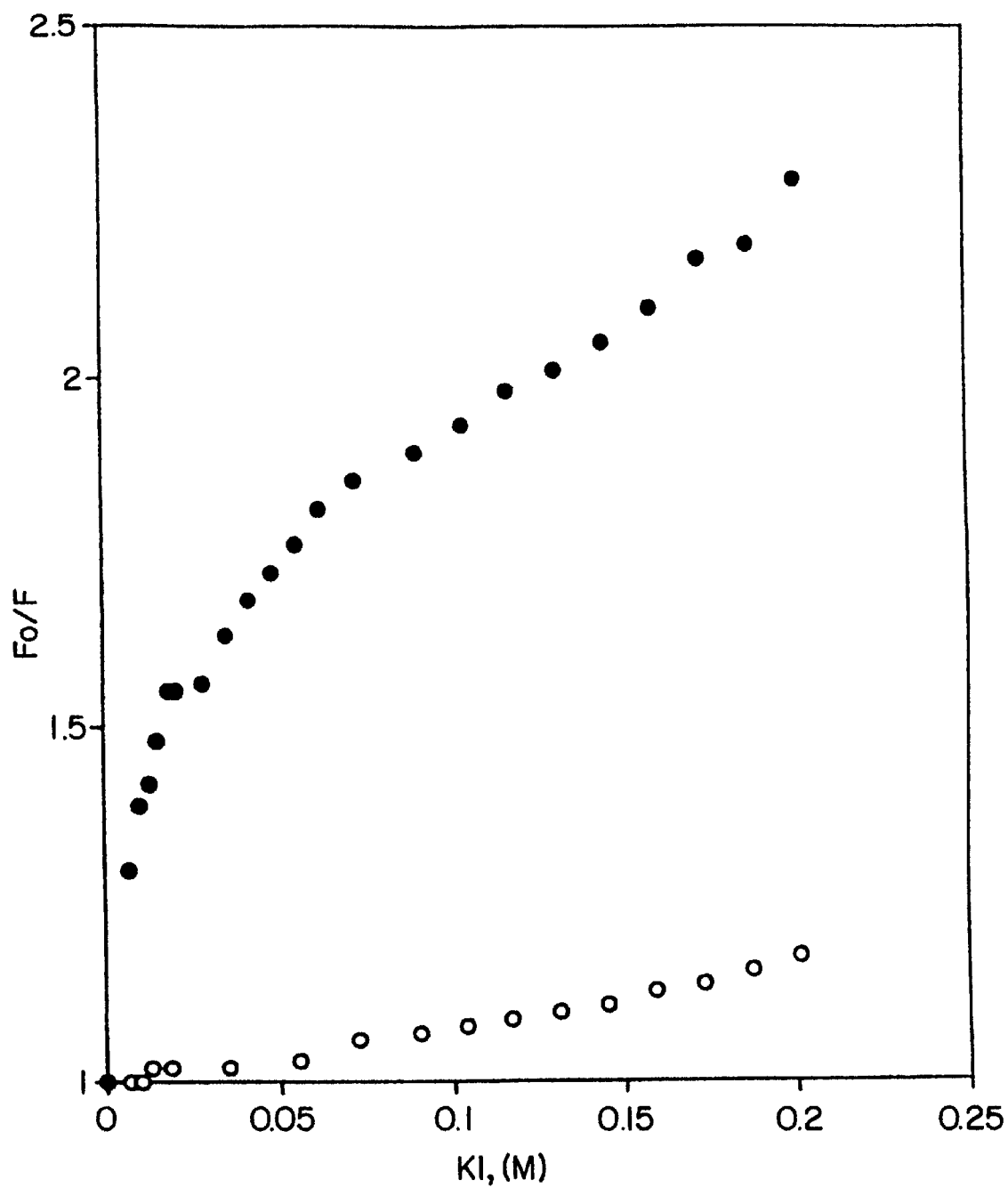
FIG. 3 shows Stern-Volmer plots of the quenching of rhG-CSF fluorescence by KI in the absence (●) and presence (○) of DOPG vesicles. Quenching experiments were performed by adding aliquots of KI to rhG-CSF (0.2 mg/ml) and DOPG:rhG-CSF (100:1 molar).

The Stern-Volmer plots of the data are shown in FIG. 3. In the absence of DOPG vesicles, rhG-CSF fluorescence is efficiently quenched by KI. In the presence of DOPG, the Stern-Volmer plot of the data is linear, indicating that iodide has poor access to both tryptophans. The data shows that the tryptophan residue which is iodide-accessible in the absence of DOPG becomes iodide-inaccessible in the presence of DOPG. Therefore, the portion of rhG-CSF containing this tryptophan must be embedded in the DOPG bilayer.

3. Energy transfer measurements.

As previously shown, energy transfer can occur between tryptophan donors and lipid soluble fluorescent acceptors such as pyrene decanoic acid, since the excitation spectrum of this probe significantly overlaps the emission spectra of tryptophan. Friere et al., *Biochemistry* 22: 1675–1680 (1983). If the protein inserts into lipid membranes, energy transfer from tryptophan to pyrene will lead to quenching of the tryptophan fluorescence. In this experiment, the tryptophan emission intensity of various lipid:G-CSF complexes was recorded before ($F_o$) and after (F) addition of various amounts of pyrene decanoic acid (30 $\mu$g/ml stock in tetrahydrofuran). The samples were stirred continuously during pyrene decanoic acid addition to promote mixing between pyrene decanoic acid and the sample. The ratio of $F/F_0$ is proportional to the amount of energy transfer occurring between G-CSF tryptophans and the hydrophobic energy acceptor pyrene decanoic acid.

Figure 4:
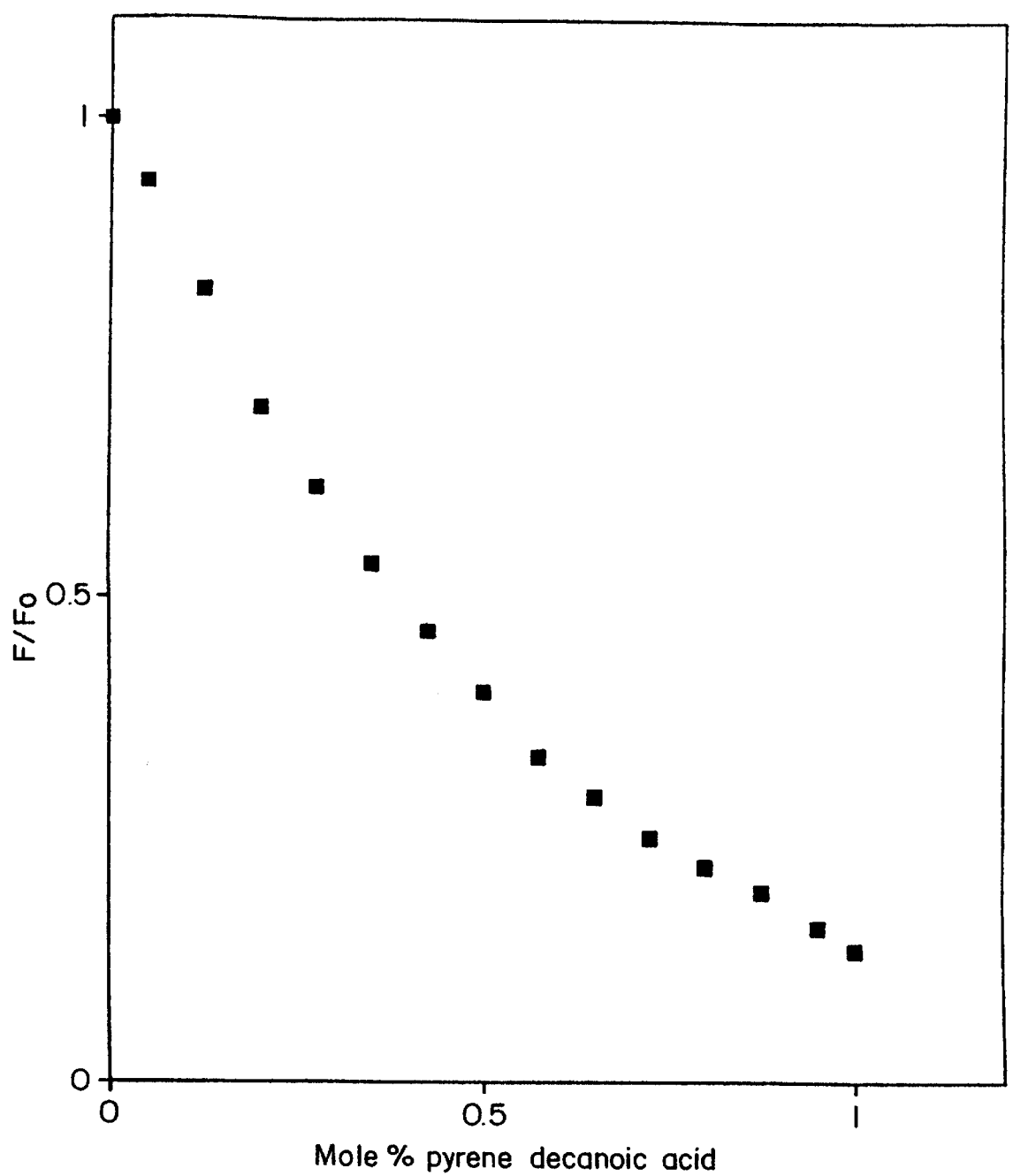
FIG. 4 depicts quenching of rhG-CSF tryptophan fluorescence upon addition of pyrene decanoic acid. The emission wavelength was 327 nm. The DOPG:rhG-CSF ratio was 100:1 (molar).

FIG. 4 shows the quenching profile for rhG-CSF in the presence of DOPG (100:1 lipid:protein ratio) as a function of added pyrene decanoic acid. The quenching occurs at very low pyrene decanoic acid concentrations (<1 mole %), so the effect of the fluorescent probe on the membrane structure and behavior is minimal. Since pyrene decanoic acid can be expected to rapidly partition into lipid bilayers, the present data indicate that rhG-CSF is embedded in DOPG membranes deep enough to allow efficient energy transfer from tryptophan to the pyrene acceptor. Energy transfer was confirmed by examining the excitation spectra of pyrene decanoic acid-labeled DOPG vesicles in the presence and absence of rhG-CSF.

The analysis above shows that rhG-CSF can closely interact with an unsaturated phospholipid like DOPG. In the presence of DOPG vesicles, a rhG-CSF tryptophan is protected from a water soluble fluorescence quencher but is susceptible to quenching via energy transfer to a hydrophobic fluorescent probe. Taken together, the data show that rhG-CSF can insert into membranes composed of DOPG. Membrane insertion is detectable once a 10:1 ratio (lipid:G-CSF) is reached, and this number may represent the number of lipids which surround the inserted portion of the protein.

EXAMPLE 2

In this example, the ability of rhG-CSF to interact with other phospholipids was determined using comparisons of $F/F_0$ intensity and emission maximums as described above. In each instance, the mole ratio of lipid:rhG-CSF was 100:1.

Figure 5:
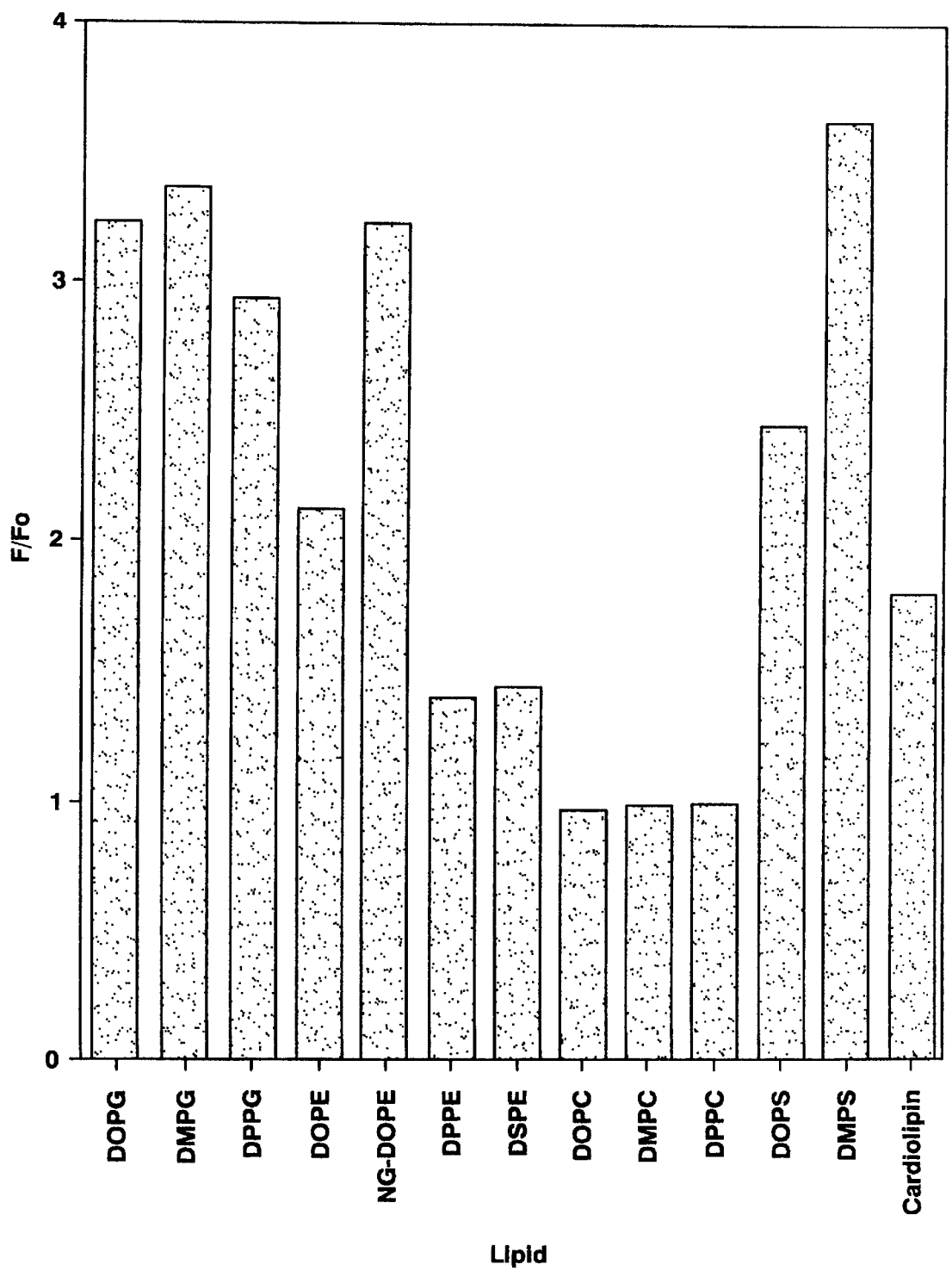
FIG. 5 is a graph showing a comparison of F intensity changes for rhG-CSF in the absence and presence of various lipids. In each case, the lipid:protein ratio was 100:1 (molar).
Figure 6:
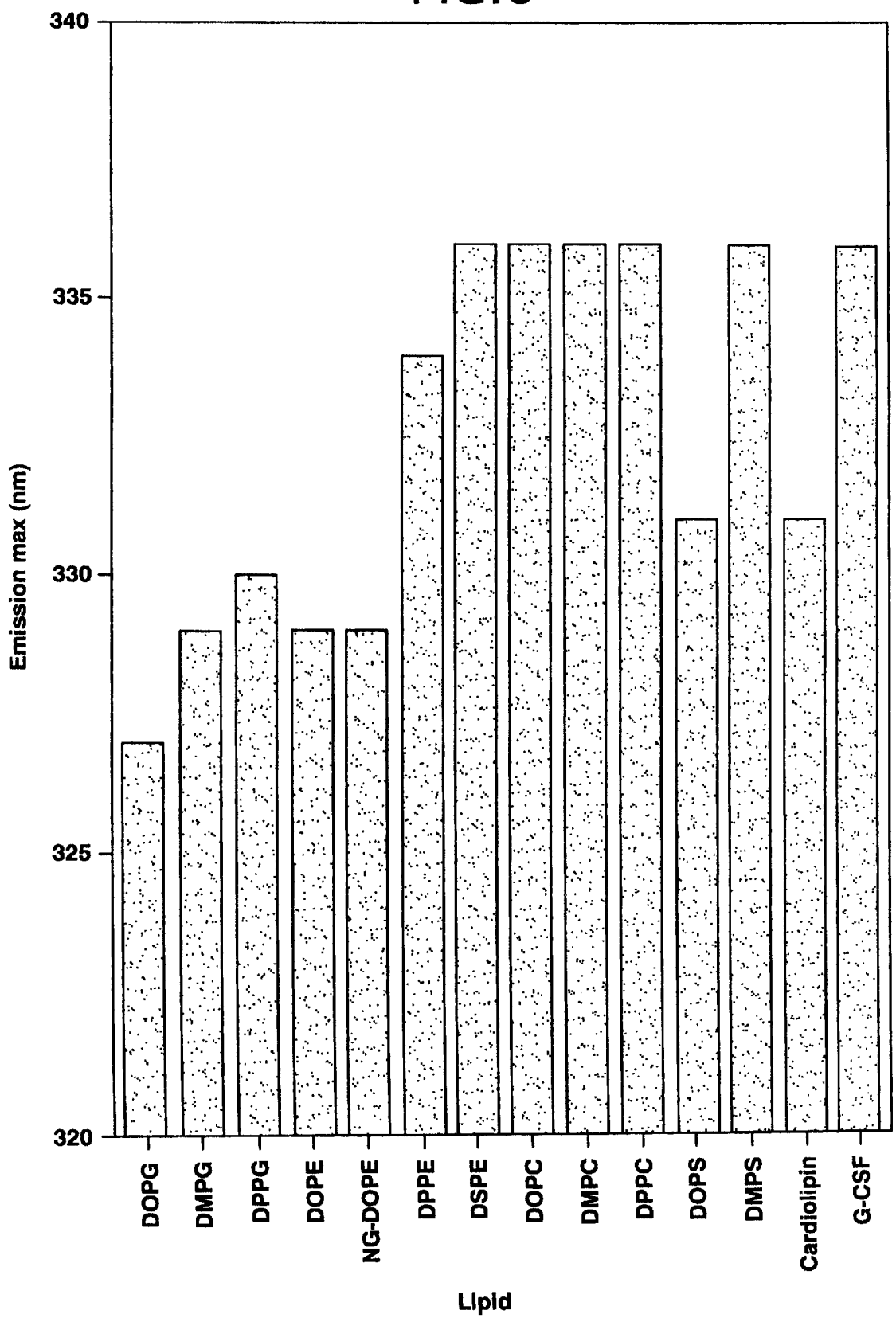
FIG. 6 is a graph showing a comparison of shifts in emission maximums for rhG-CSF in the absence and presence of various lipids. In each case, the lipid:protein ratio was 100:1 (molar).

FIG. 5 shows the $F/F_0$ data for rhG-CSF in the absence and presence of various lipids. FIG. 6 shows the emission maximum data for the same compositions. The data in FIG. 5 and FIG. 6 demonstrates that, in addition to DOPG, rhG-CSF can insert into DMPG, DPPG, and less efficiently, into the phosphatidylethanolamines (PE's) and the phosphatidylserines (PS's). In addition, NG-DOPE (DOPE sample where the PE headgroup was made more negative) was found to provide for improved insertion of the rhG-CSF than DOPE.

Figure 7:
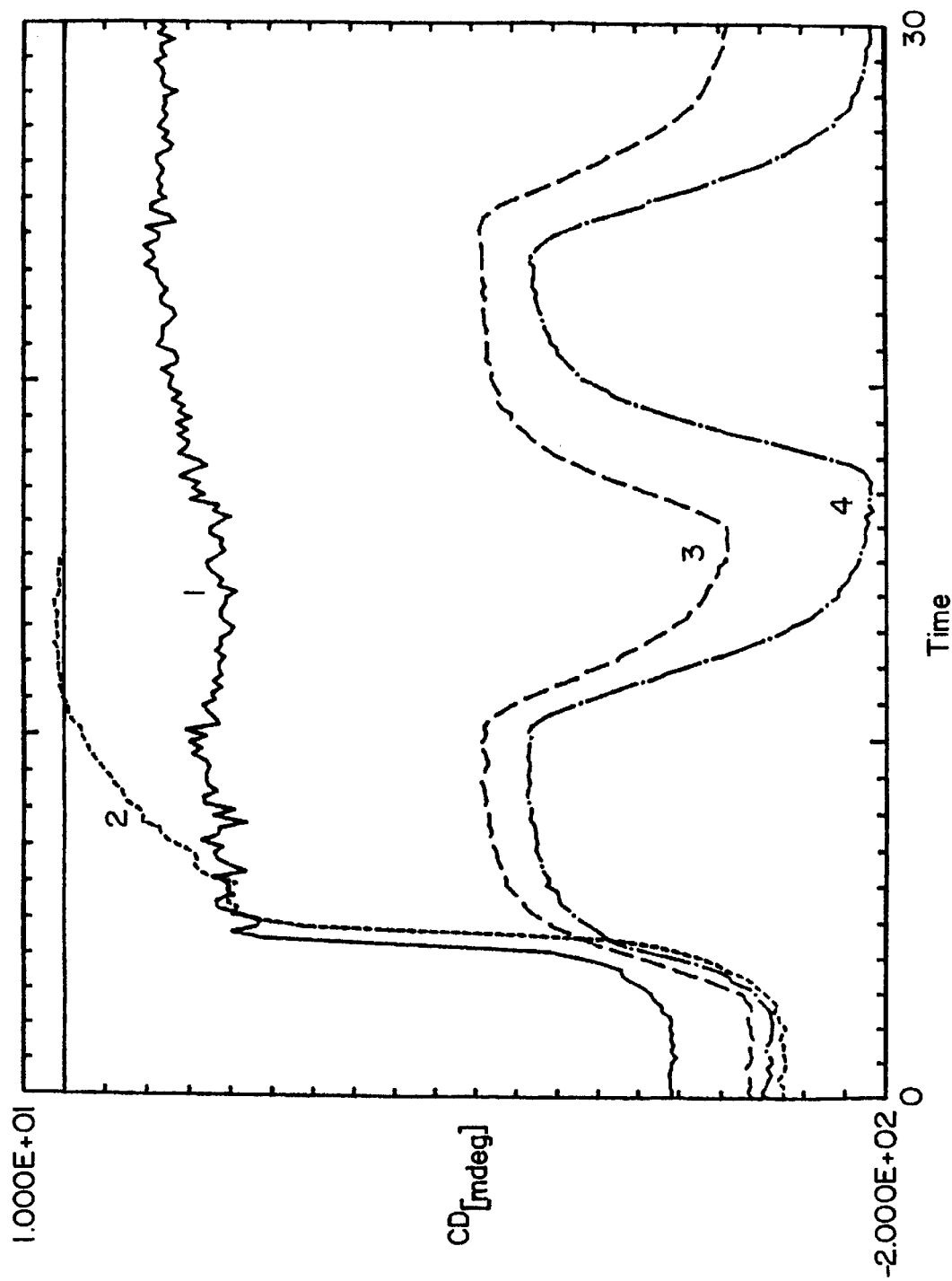
FIG. 7 shows the effect of DMPC (curve 2), DMPG (curve 3), and DMPA (curve 4) on the CD of rhG-CSF (curve 1). In each case, the lipid:protein ratio was 50:1 (molar) in water, pH 6.0.
Figure 8:
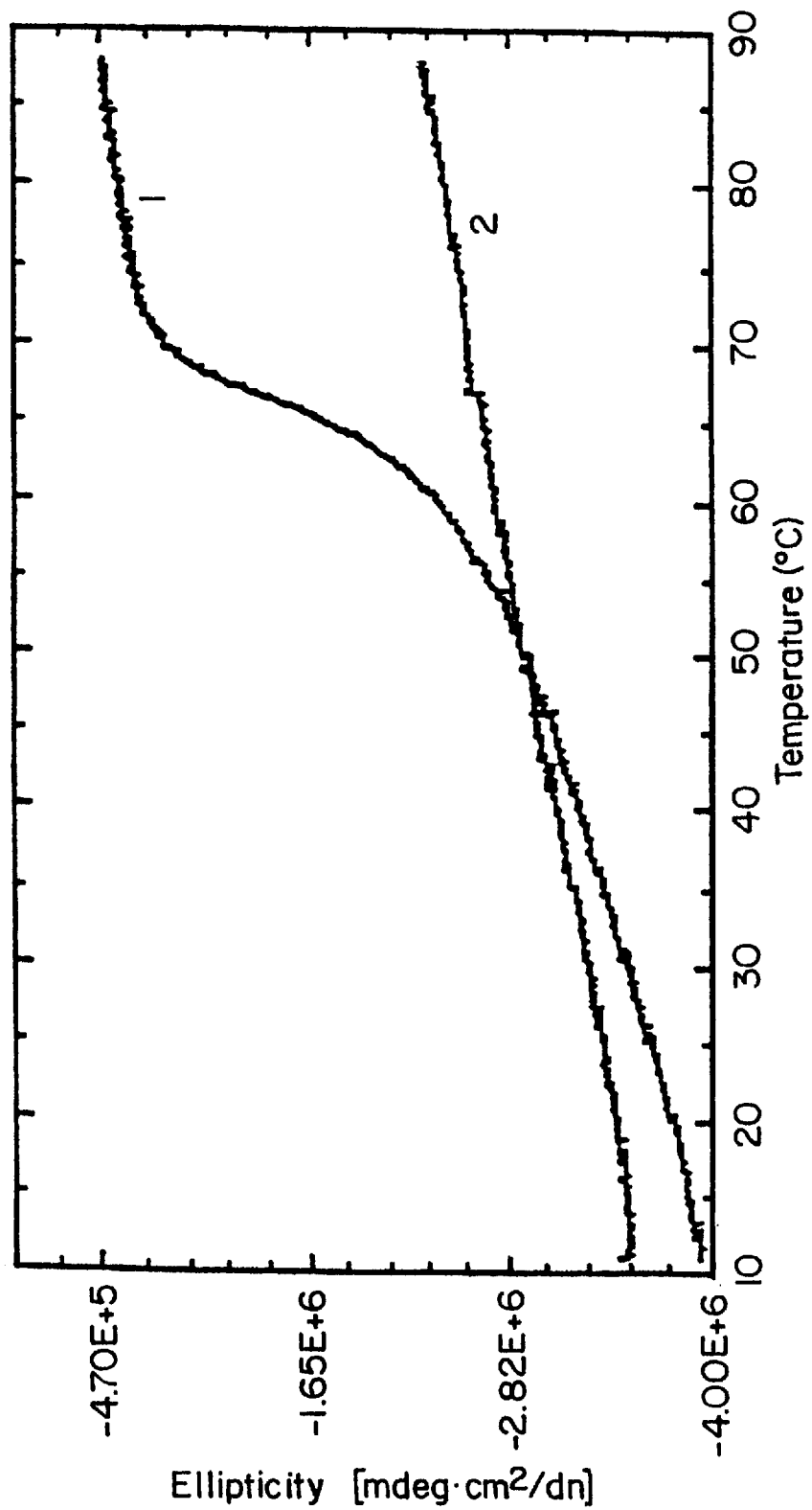
FIG. 8 shows the effect of increasing temperature on the CD of rhG-CSF (curve 1) or DOPG:rhG-CSF (140:1 molar) (curve 2). The rhG-CSF concentration was 80 μg/ml in water, pH 6.0. The temperature was scanned from 10°–90° C. at a rate of 100° C./hour.
Figure 9:
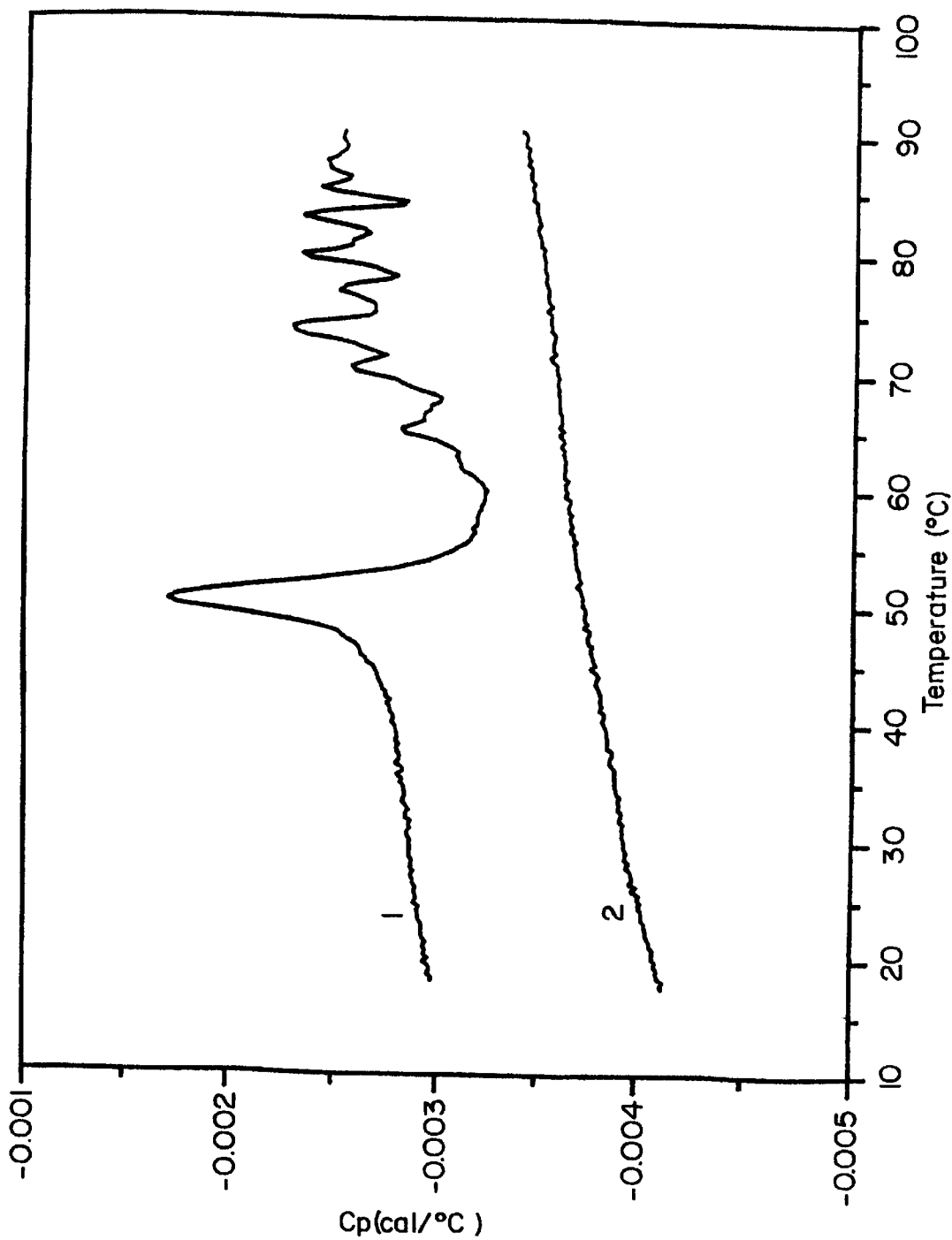
FIG. 9 shows differential scanning calorimetry thermograms for rhG-CSF (curve 1) and DOPG:rhG-CSF (45:1 molar) (curve 2). The concentration of rhG-CSF in the samples was 1 mg/ml (pH 7.0 in water). The scan rate was 90° C./hour.

DOPC, DMPC and DPPC are neutral lipids and these vesicles had little if no effect on either the emission maximum or the fluorescence intensity of rhG-CSF, indicating that no interaction took place with these phospholipids (see FIGS. 5 and 6, and FIG. 7, curve 2).

The data above demonstrate that a protein capable of transitioning into the molten globular state can insert in various lipid vesicles. However, this rhG-CSF:lipid interaction only occurs when a negatively charged lipid vesicle is used. Among the negatively charged lipid vesicles, those vesicles with the greater negative charge seem to provide for a stronger rhG-CSF:lipid interactions.

EXAMPLE 3

In this example, the effect of the DOPG:rhG-CSF interaction as it relates to protein stability was determined. Circular dichroism measurements were made on a Jasco J-720 instrument equipped with a Peltier-type thermostatted cell holder and a magnetic stirrer. Circular dichroism at 222 nm was measured using a final rhG-CSF concentration of 80 $\mu$g/ml, pH 6.0. Differential scanning calorimetry measurements were made using a Microcal MC-2 calorimeter. Samples of rhG-CSF (1 mg/ml, in water) or DOPG:rhG-CSF (45:1 mole/mole, in water) were scanned at a rate of 90° C./hour. Data were stored and analyzed using the Microcal software.

Temperature-induced changes in the alpha helicity of G-CSF can be followed by measuring circular dichroism (222 nm) as a function of increasing temperatures. The thermally-induced unfolding of rhG-CSF at pH 6.0 is shown in FIG. 8. The curve indicates that a fairly sharp transition occurs at ~60°–70° C. which leads to loss of alpha helicity. After this transition the rhG-CSF irreversibly precipitates from solution. The temperature range of the unfolding is similar to the melting temperature of rhG-CSF at pH 7.0 as determined by differential scanning calorimetry as shown in FIG. 9.

By contrast, DOPG:rhG-CSF samples show a gradual loss of alpha helicity with increasing temperature and, unlike rhG-CSF alone, the temperature-induced unfolding of DOPG:rhG-CSF does not appear to be cooperative (see FIG. 8). This conclusion is also demonstrated by the lack of a melting transition as shown by differential scanning calorimetry (FIG. 9). Remarkably, DOPG:rhG-CSF samples can recover alpha helicity after heating to 95° C. and can be repeatedly cycled between 95° C. and 10° C. with full recovery of helicity upon cooling (see FIG. 10). rhG-CSF alone under these conditions is irreversibly unfolded and precipitates from solution.

The effects of DMPG and DPPG on G-CSF circular dichroism was also examined. A 150:1 lipid:rhG-CSF ratio was used and, as was the case with DOPG, DMPG and DPPG also stabilize the secondary structure of rhG-CSF (FIGS. 11–13).

These data demonstrate that the interaction of rhG-CSF with DOPG, DMPG and DPPG enhances the stability of the protein under conditions where rhG-CSF alone is unstable. The interaction directly stabilizes the secondary and tertiary structure of rhG-CSF.

EXAMPLE 4

In this example, the effect of the rhG-CSF:DOPG interaction as it relates to the biological activity of rhG-CSF was determined. The in vitro activity of rhG-CSF was assayed utilizing the G-CSF dependent uptake of [$^3$H]-thymidine by murine bone marrow cells as described in Zsebo et al., *Immunobiology* 172: 175–184 (1986). All activity assays were performed in triplicate. In vivo activity was determined by subcutaneous injection of hamsters (rhG-CSF dose of 100 µg/kg) and measurements of white blood cell (WBC) count.

1. In vitro activity

A. The specific activity of rhG-CSF in the absence and presence of DOPG was determined. Heat treated rhG-CSF and DOPG:rhG-CSF samples were also tested. The results are summarized in TABLE 1.

TABLE 1

| Sample | Specific activity (U/mg/protein) |
|---|---|
| rhG-CSF | 0.66 ± 0.09 |
| rhG-CSF (heated)[a] | Not Detectable |
| DOPG:rhG-CSF[b] | 0.61 ± 0.11 |
| DOPG:rhG-CSF[b] (heated)[a] | 0.52 ± 0.08 |

[a]Sample was incubated for 10 minutes at 85° C. in a water bath prior to performing the assay.
[b]DOPG:rhG-CSF ratio of 50:1 (mole/mole).

As shown in TABLE 1, insertion into DOPG bilayers does not adversely affect the biological activity of rhG-CSF. After heating to 85° C. for 10 minutes, rhG-CSF has undetectable activity and the protein precipitates. After similar treatment, DOPG:rhG-CSF retains ~85% of the activity of unheated rhG-CSF and fully recovers secondary structure upon cooling.

Figure 14:
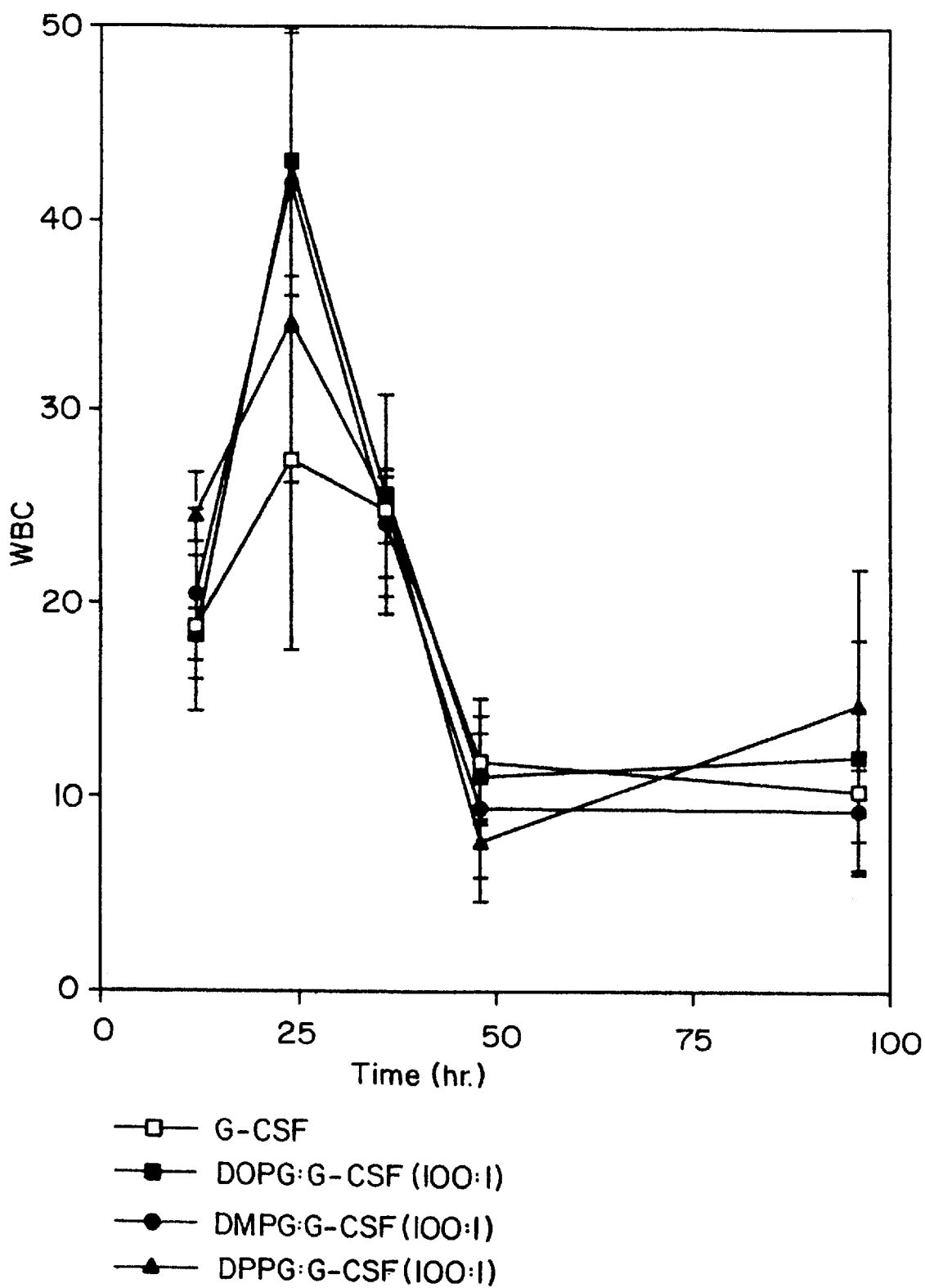
FIG. 14 shows the effects of various lipids on the in vivo activity of rhG-CSF. Activity (WBC count) was measured after subcutaneous injection of hamsters. The rhG-CSF dose was 100 μg/kg with a 100:1 lipid:protein ratio.

B. The ability of various lipids to stabilize rhG-CSF during freeze drying was also studied. Samples of rhG-CSF in combination with various lipids were freeze dried and assayed (as described above) for activity. DOPG, DMPG, and DPPG when mixed with rhG-CSF allow ~100% retention of rhG-CSF bioactivity after freeze drying (FIG. 14). rhG-CSF alone did not survive the freeze-drying process.

2. In vivo activity

Figure 15:
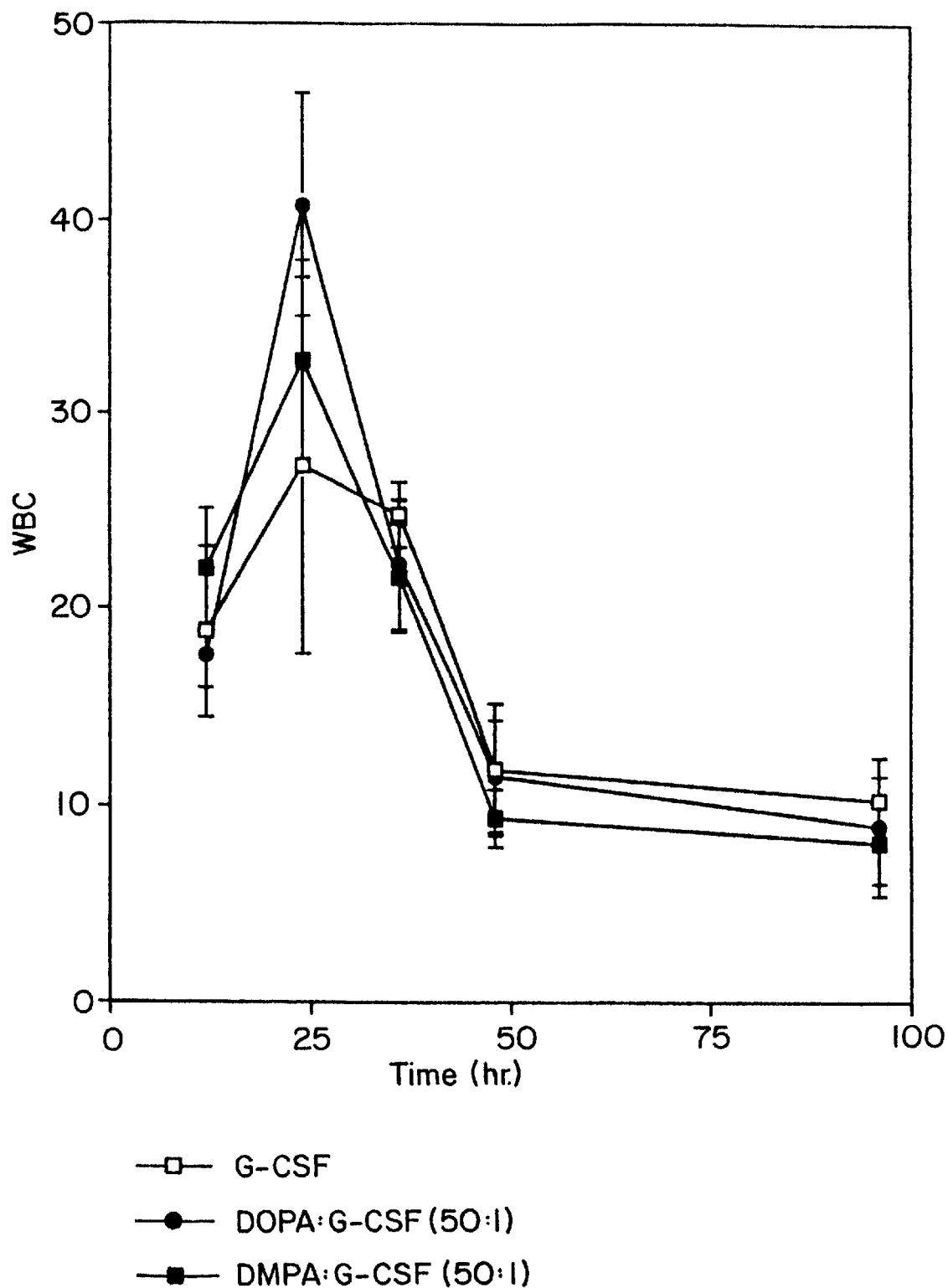
FIG. 15 shows the effects of various lipids on the in vivo activity of rhG-CSF. Activity (WBC count) was measured after subcutaneous injection of hamsters. The rhG-CSF dose was 100 μg/kg with a 50:1 lipid:protein ratio.
Figure 16:
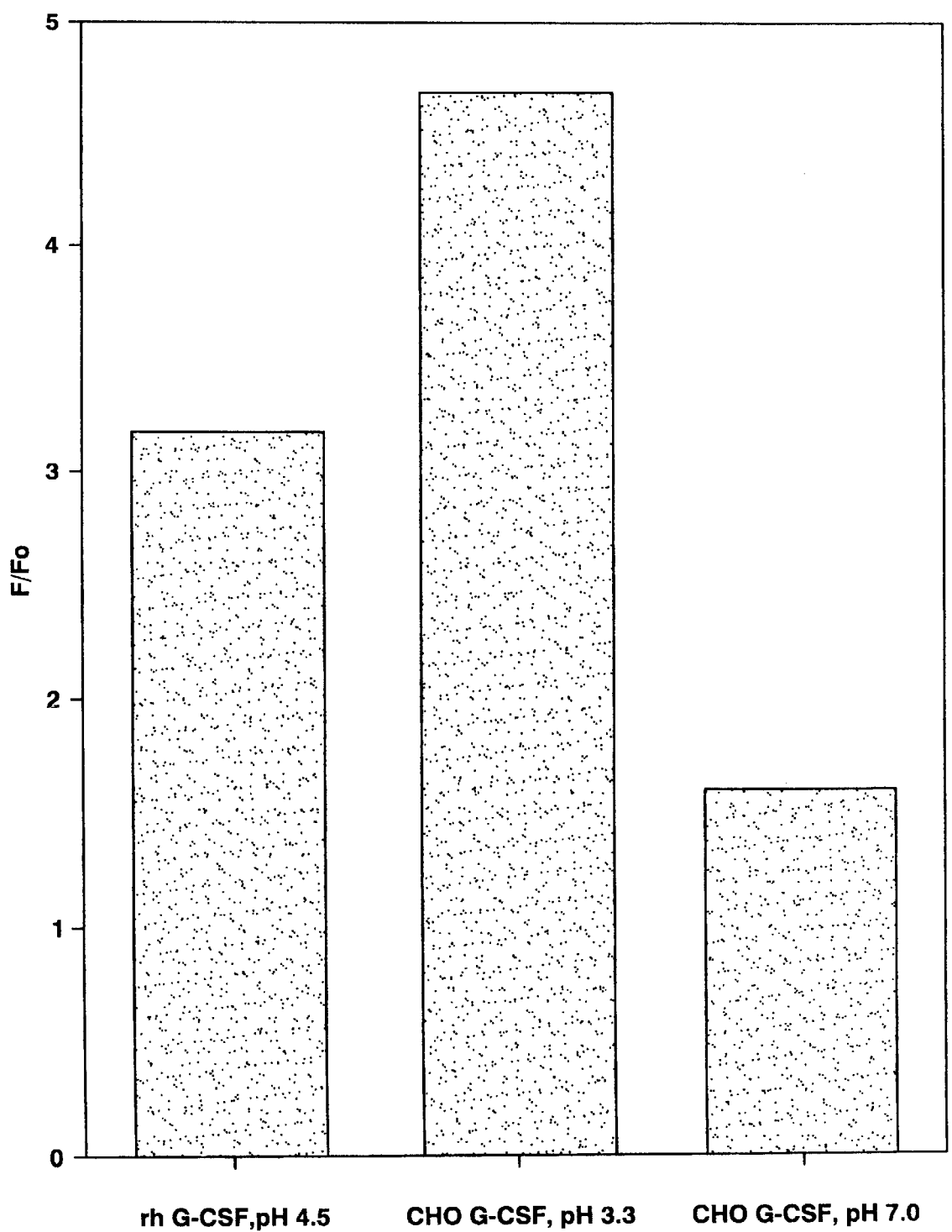
FIG. 16 is a graph showing a comparison of F intensity changes for CHO-G-CSF in the absence and presence of DOPG at varying pH's. In each case, the lipid:protein ratio was 100:1 (molar).

The activity (WBC count) of rhG-CSF in the absence and presence of lipid was determined. Activity was measured after subcutaneous injection (rhG-CSF dose of 100 µg/kg) on day 0. Five different lipid:rhG-CSF complexes were assayed and in each instance the lipid:rhG-CSF complex retained in vivo activity (FIGS. 15 and 16).

The studies above demonstrate that insertion into negatively charged lipid bilayers does not adversely affect the biological activity of rhG-CSF. Additionally, it appears that the protective effect of the lipid protects rhG-CSF during the freeze-drying process.

EXAMPLE 5

In this example, chemically modified G-CSF (pegylated G-CSF (PEG-G-CSF)) and G-CSF obtained as a product of eucaryotic host cell expression (CHO-G-CSF) were tested for their ability to interact with negatively charged lipid vesicles. For the CHO-G-CSF, the determinations were made using comparisons of $F/F_0$ intensity and emission maximums (as described in Example 1 above). In each instance, the mole ratio of lipid:protein was 100:1. For the PEG-G-CSF, the determination was based upon circular dichroism analysis.

Figure 17:
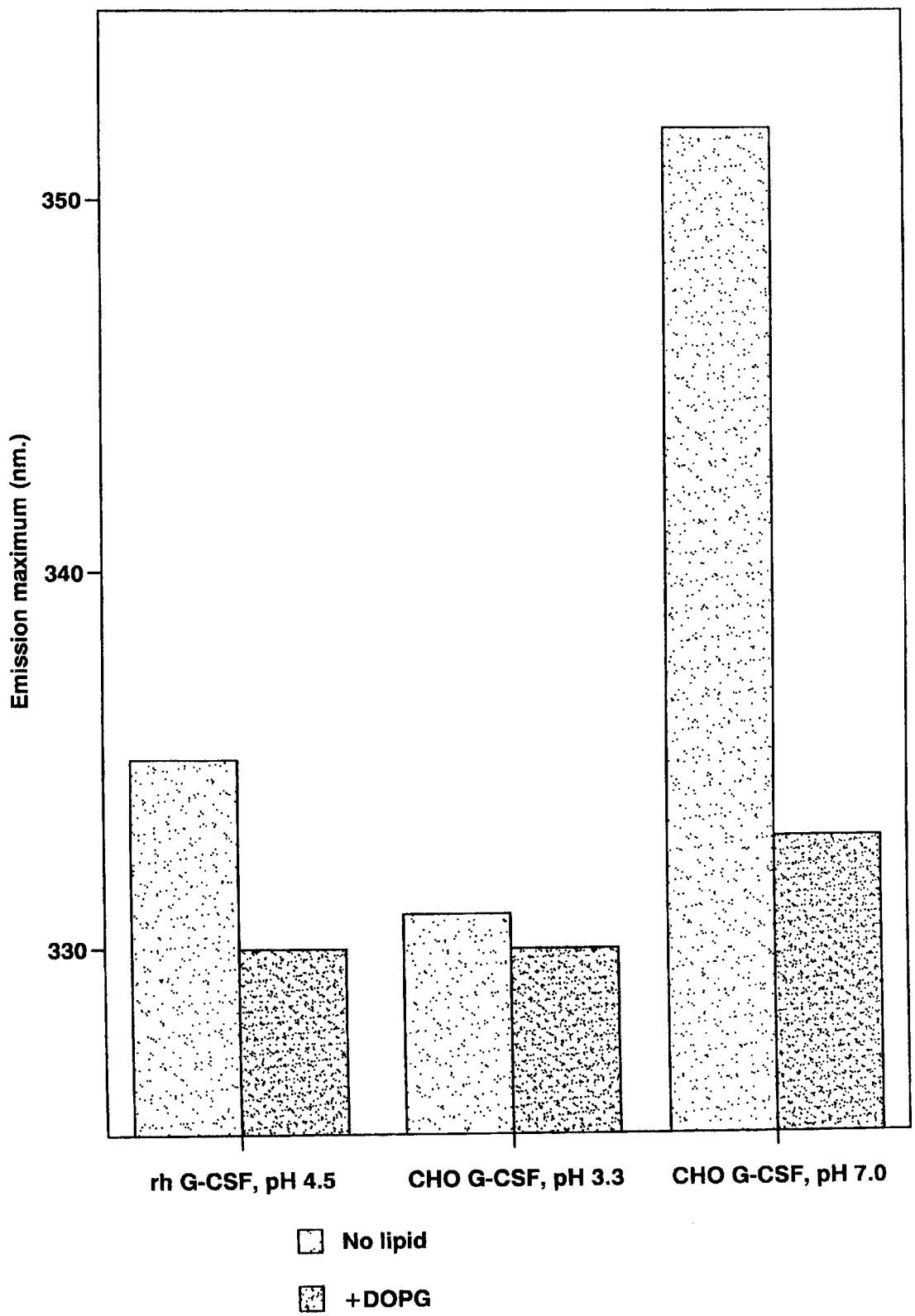
FIG. 17 is a graph showing a comparison of shifts in emission maximums for CHO-G-CSF in the absence and presence of DOPG at varying pH's. In each case, the lipid:protein ratio was 100:1 (molar).
Figure 18:
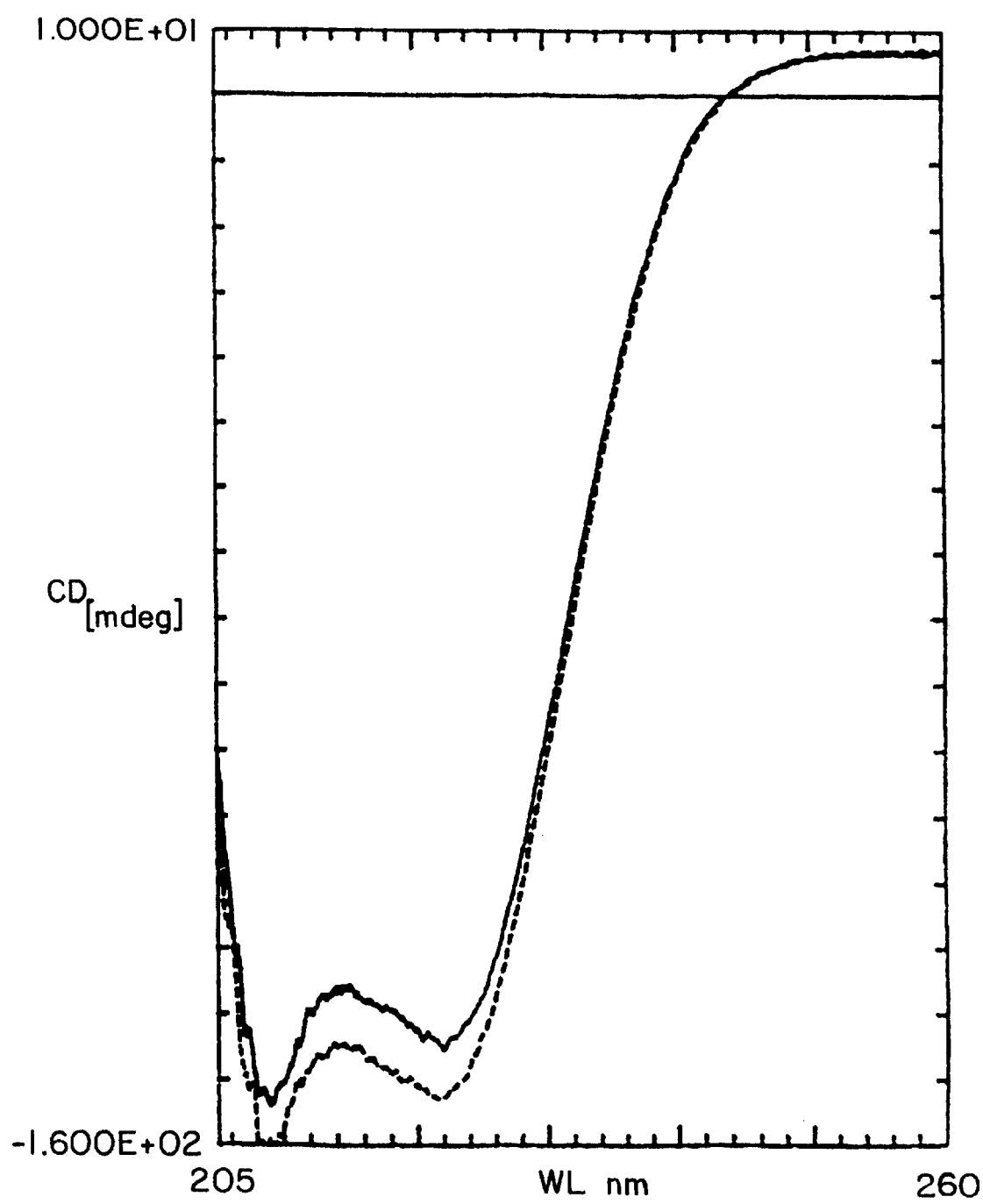
FIG. 18 shows the effect of temperature cycling on the CD of PEG-G-CSF (——) and DMPG:PEG-G-CSF (17:1 molar) (----). The samples were heated to 90° C. and cooled to 10° C.

The CHO-G-CSF used was produced using recombinant DNA technology in which Chinese Hamster Ovary (CHO) cells were transfected with a DNA sequence encoding human G-CSF as described in U.S. Pat. No. 4,810,643 to Souza. The CHO-G-CSF was prepared as a 0.6 mg/ml solution in PBS, pH 7.0. CHO-G-CSF was shown to interact with DOPG in a manner similar to rhG-CSF, with each sample showing increased fluorescence intensity in the presence of DOPG, as well as a blue shift in emission maximum in the presence of DOPG (FIGS. 17 and 18). Therefore, the DOPG interaction is not due to some peculiarity of the recombinant form of G-CSF.

Figure 19B:
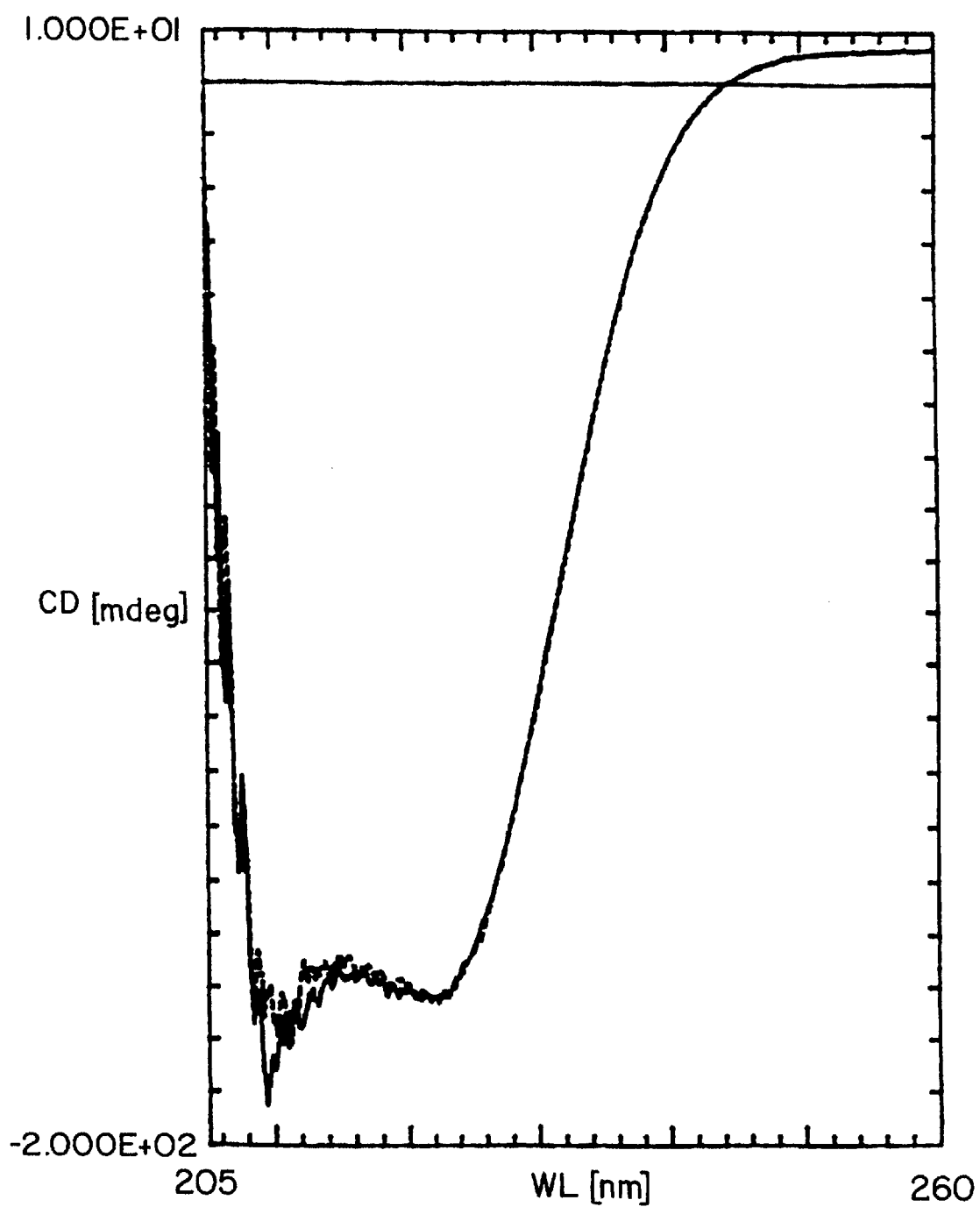

PEG-G-CSF used in these experiments was tri-tetra pegylated *E. coli* derived G-CSF (using PEG 6000). DMPG:PEG-G-CSF (17:1 mole/mole) samples were prepared using procedures described above. The DMPG:PEG-G-CSF samples were found to fully recover secondary structure after heating (FIG. 19). Despite the presence of the PEG molecules, the derivatized protein was able interact with the lipid in the same way as the native protein.

The data above show that the stabilizing effects associated with G-CSF interaction with a negatively charged lipid vesicle is not unique only to rhG-CSF obtained as a product of procaryotic host cell expression. A chemically modified protein capable of transitioning to a MGS and contacted with a liposome vesicle, here PEG-G-CSF:DMPG, also exhibited stabilizing effects.

EXAMPLE 6

Figure 20B:
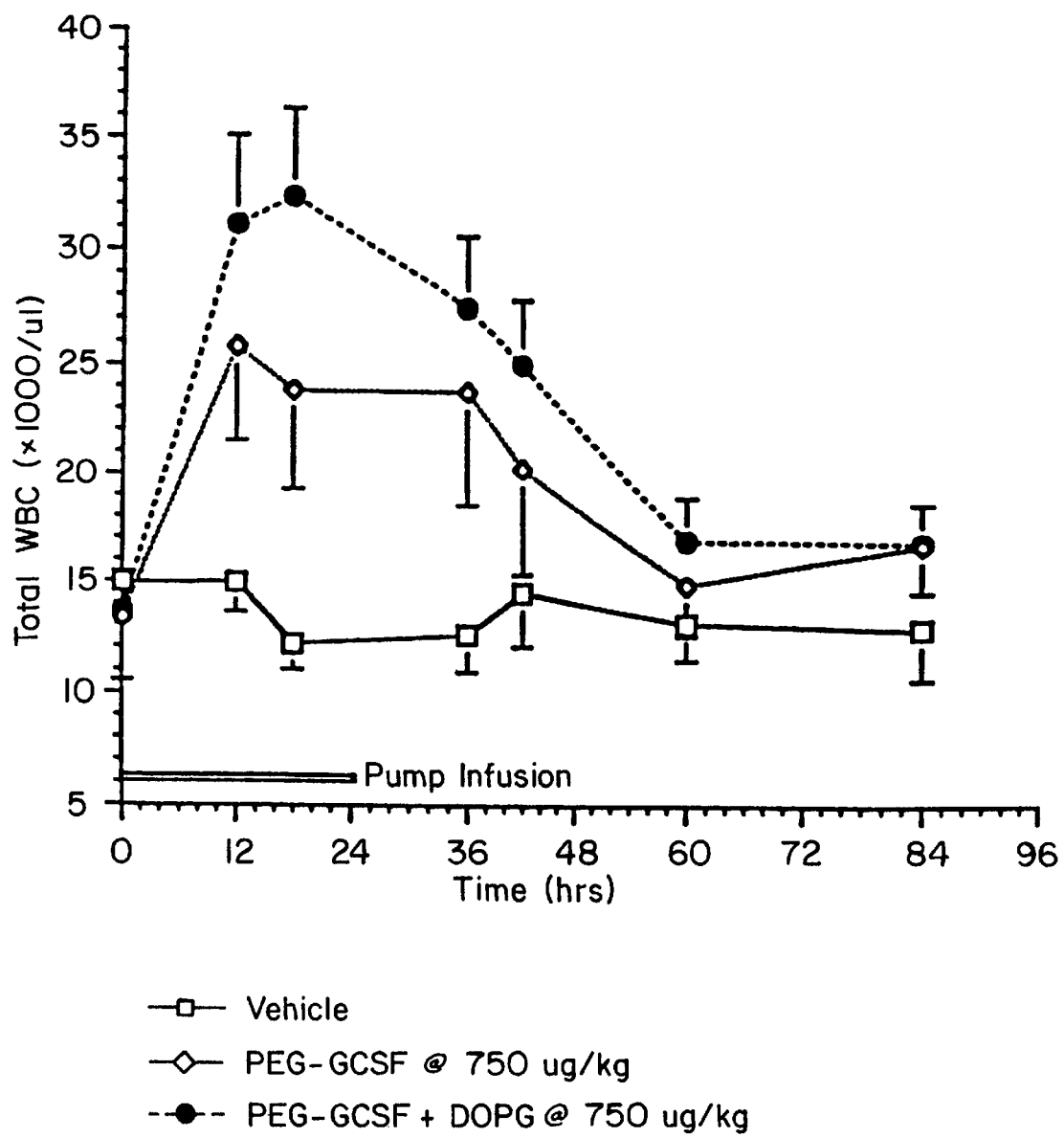

In this example, the effects of DMPG and DPPG on GM-CSF was studied. The GM-CSF was recombinant human GM-CSF as described in U.S. Pat. No. 5,047,504 to Boone, and prepared as a 1 mg/ml solution in phosphate buffered saline (PBS), pH 7.0. A lipid:GM-CSF ratio of 17:1 was used and thermal stability was measured using circular dichroism analysis as described above. DMPG and DPPG can lead to better thermal stability of GM-CSF, i.e., recovery of secondary structure after heating (FIGS. 20*a* & 20*b*).

These data provide another example of a protein, capable of transitioning into the molten globular state, interacting with a negatively charged lipid vesicle to provide better thermal stability to the protein.

EXAMPLE 7

In this example, a DOPG:PEG-G-CSF complex was used to evaluate the possibility of increasing the therapeutic response to G-CSF after enteral administration. For this experiment, the DOPG was prepared as described in EXAMPLE 1 and the PEG-G-CSF was prepared as described in EXAMPLE 5. 100 µmole of lipid (797 µl) were dried under vacuum and then 1 ml of milli Q water was added to make a 100 mM solution of the lipid. This solution was sonicated for 5 minutes in a sonicating water bath (Model G 112SP1T from Lab. Supply Inc., Hicksville, N.Y.) or until the lipid solution was clear. 9 µmole of the DOPG solution (90 µl) was added to 90 nmol of native rhG-CSF or PEG-G-CSF in 1 mM HCl. The solution was vortexed and brought to a final volume of 2 ml with 1 mM HCl. For intraduodenal administration into rats, the material was placed in an osmotic pump which was implanted into the animal. The release of the material occurs over 24 hours.

The results of the total WBC analysis for the animals receiving both rhG-CSF and PEG-G-CSF with and without lipid are shown in FIGS. 21A–21B. FIG. 21a shows that infusion of native G-CSF fails to stimulate a WBC response as compared to vehicle control. The addition has little impact on the therapeutic response of the animals to rhG-CSF.

The response of the rats to the pegylated G-CSF is shown in FIG. 21b. One can see that the PEG-G-CSF alone has stimulated a WBC response. The elevation of WBC is sustained out to 48 hours before returning to baseline. The PEG-G-CSF formulated with DOPG also stimulates a WBC response, and this response is nearly 2-fold greater than for PEG-G-CSF alone. These results are confirmed by the measured serum levels of PEG-G-CSF after the infusion (FIG. 22).

These data demonstrate that including an anionic lipid such as DOPG in an oral formulation of PEG-G-CSF appears to increase the therapeutic response elicited by the derivatized protein. The mechanism involved is not currently understood.

EXAMPLE 8

In this example, the effects of DMPG on MGDF was studied. The MGDF was recombinant human *E. coli* derived MGDF 1-163 prepared as a 1.0 mg/ml solution in 10 mM sodium acetate, 5% sorbitol, at pH 5.0. The DMPG:MGDF complexes were prepared as described in EXAMPLE 1.

Analysis of the DMPG:MGDF Complexes
1. Tryptophan emission spectra.

There is one tryptophan residue in MGDF (position 51) that was used the monitor the interaction of MGDF with DMPG vesicles. Tryptophan fluorescence of the DMPG-:MGDF complexes was assayed as described in EXAMPLE 1, using an MGDF concentration of 0.1 mg/ml. The fluorescence spectra of MGDF in the presence and absence of small unilamellar vesicles composed of DMPG is shown in FIG. 22. MGDF has an emission maximum at 336 nm in the absence of DMPG vesicles. In the presence of DMPG at a 100:1 lipid:protein ratio, MGDF tryptophan fluorescence exhibits a blue shift in fluorescence emission maximum to 328 nm. The low wavelength of the fluorescence emission in the presence of DMPG suggests that the tryptophans are in an environment more hydrophobic than the native protein. And, as demonstrated in FIG. 23, the fluorescence shifts depend on the mole ratio of DMPG:MGDF, with membrane insertion detectable once a 8–30:1 ratio of DMPG:MGDF is reached. The fluorescent change is maximal at $\geq$100:1 mole ratios and the MGDF exhibits an apparently higher affinity for DMPG vesicles as the pH is lowered from pH 7.0 to pH 5.0. This suggests that titration of certain amino acids (e.g., histidine) may be used to enhance or attenuate the interaction.

2. Iodide quenching experiments.

Figure 24:
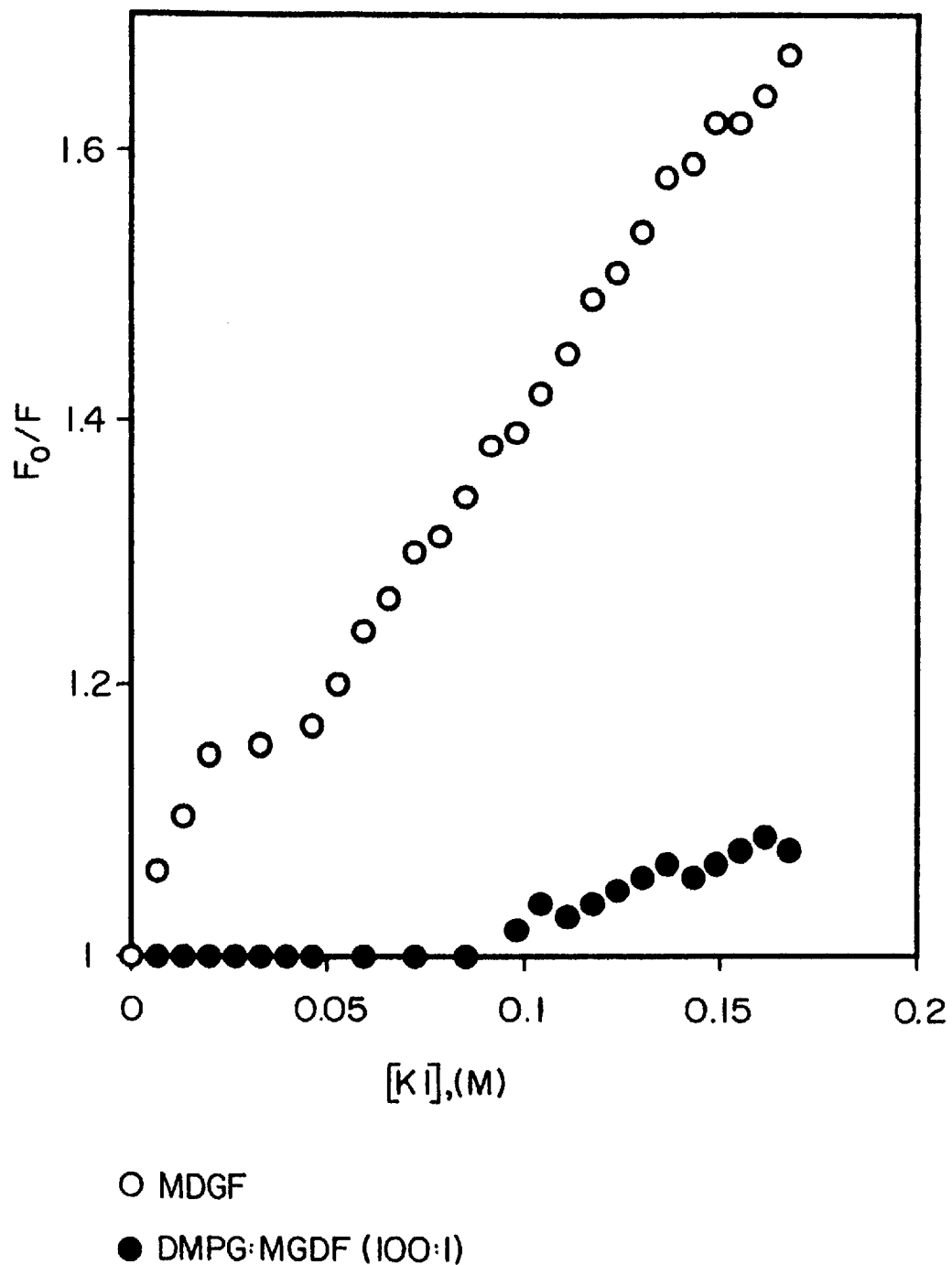
FIG. 24 shows Stern-Volmer plots of the quenching of MGDF fluorescence by KI in the absence (○) and presence (●) of DMPG vesicles. The MGDF was E. coli derived MGDF 1-163. Quenching experiments were performed by adding aliquots of KI to MDGF (0.1 mg/ml) and DMPG-:MGDF (100:1 molar).

In these experiments, MGDF and a DMPG:MGDF composition (100:1 DMPG:MGDF) was used for iodide quenching experiments as described in EXAMPLE 1. The Stern-Volmer plots of the data are shown in FIG. 24. In the absence of DMPG vesicles, MGDF fluorescence is efficiently quenched by KI. By contrast, in the presence of DMPG the tryptophan is inaccessible to iodide, indicating that the portion of MGDF containing this tryptophan must be embedded in the DMPG bilayer.

The analysis above shows that as was the case with G-CSF and GM-CSF, MGDF can closely interact with an unsaturated phospholipid like DMPG. In the presence of DMPG vesicles, a MGDF tryptophan is protected from a water soluble fluorescence quencher. Taken together, the data show that MGDF can insert into membranes composed of DMPG. Membrane insertion is detectable once a 8:1 ratio (DMPG:MGDF) is reached, and this number may represent the number of lipids which surround the inserted portion of the protein.

EXAMPLE 9

In this example, the effect of the DMPG:MGDF interaction as it relates to protein stability was determined. Thermal stability, stability in the presence of urea, and shelf-life stability of MGDF ($\pm$DMPG) were are evaluated. In each of the studies, a 100:1 mole ratio of DMPG:MGDF was used.

1. Thermal Stability.

Figure 10:
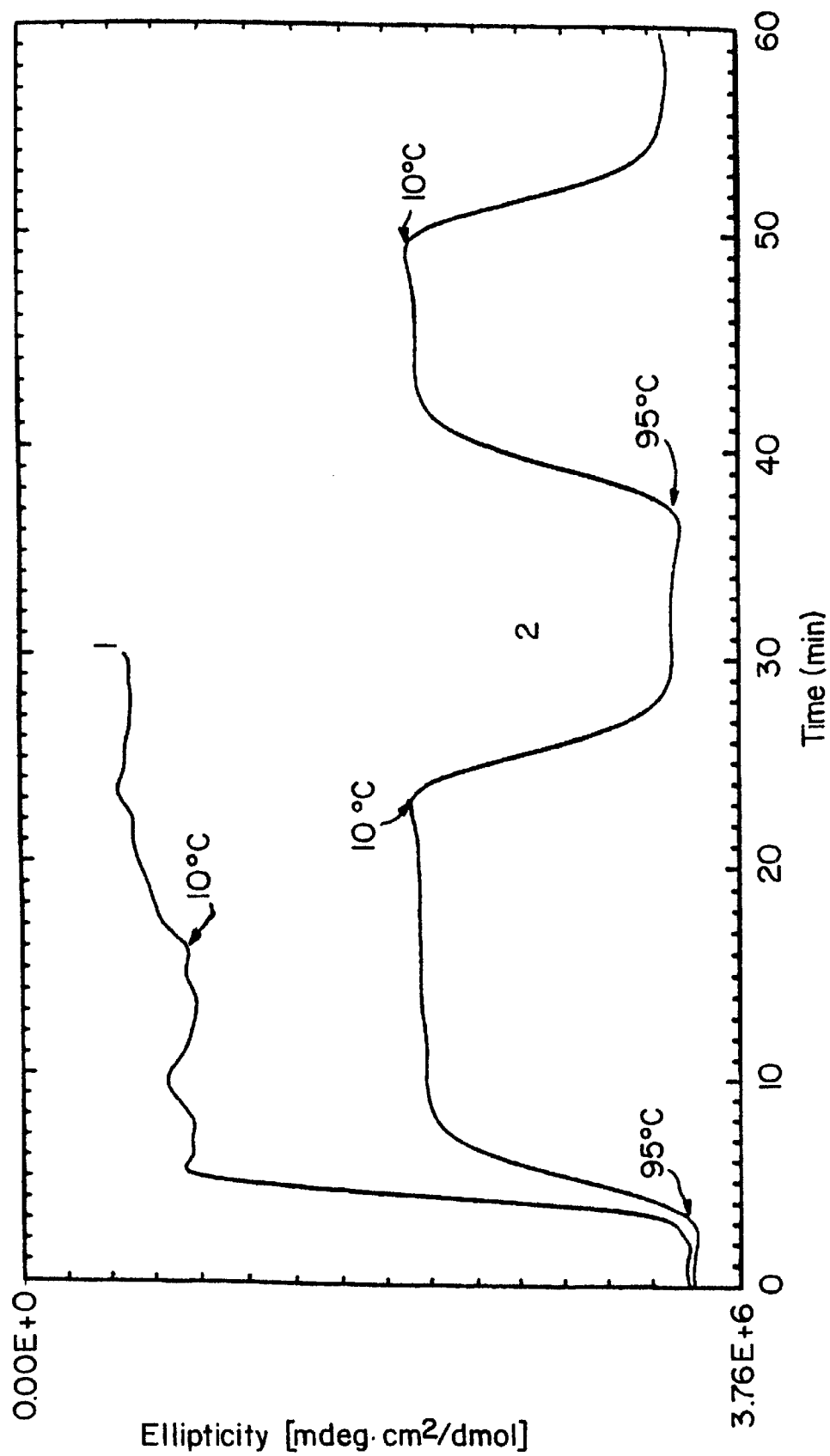
FIG. 10 shows the effect of temperature cycling on the CD of rhG-CSF (curve 1) and DOPG:rhG-CSF (140:1 molar) (curve 2). The samples were rapidly heated to 95° C. and cooled to 10° C. as indicated by the arrows. The rhG-CSF concentration in the samples was 80 μg/ml, pH 6.0.
Figure 11:
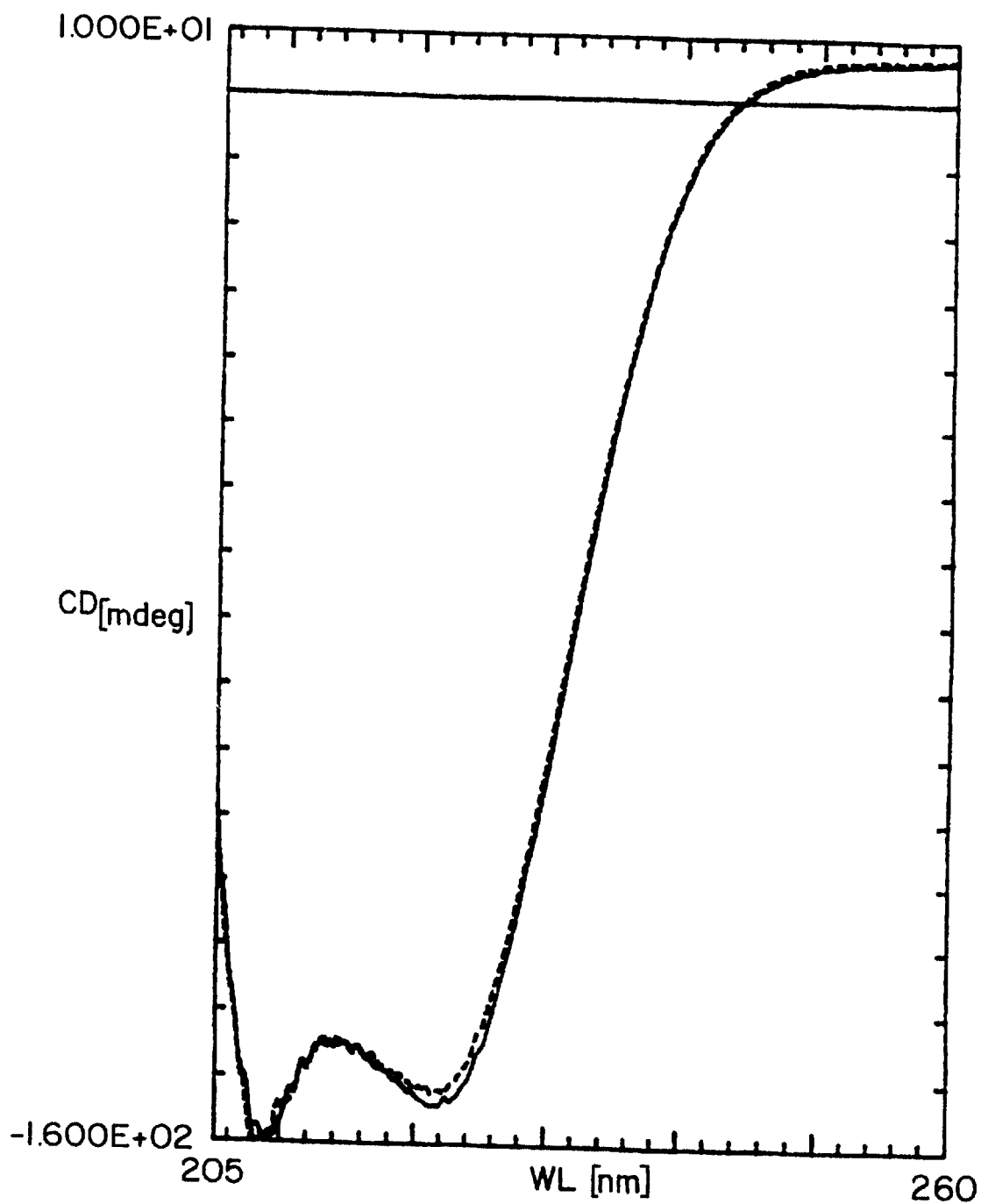
FIG. 11 shows the effect of temperature cycling on the CD of rhG-CSF (curve 1) and DMPG:rhG-CSF (150:1 molar) (curve 2). The samples were heated to 95° C. and cooled to 10° C. The rhG-CSF concentration in the samples was 80 μg/ml, pH 6.0.
Figure 12:
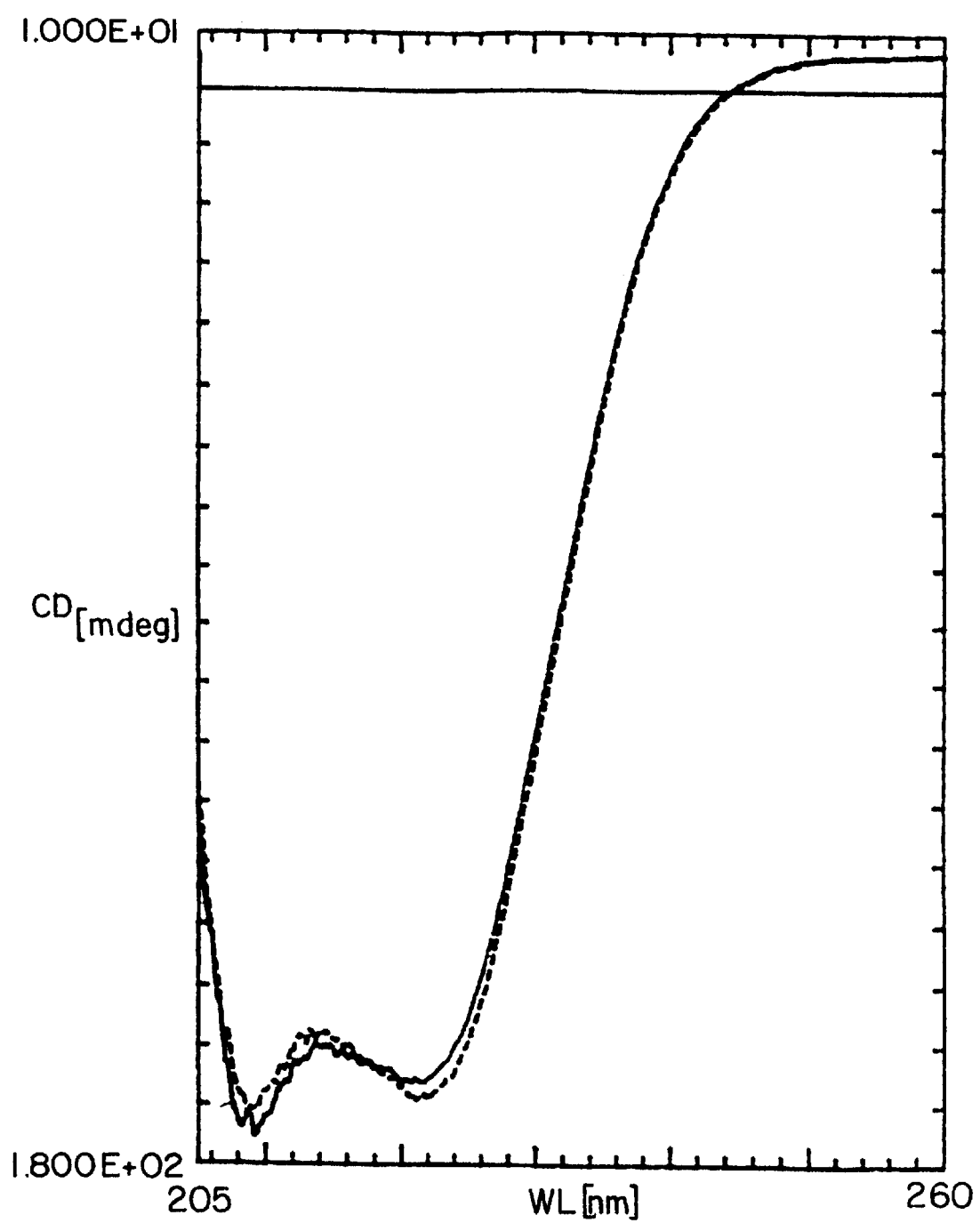
FIG. 12 shows the effect of temperature cycling on the CD of rhG-CSF (curve 1) and DPPG:rhG-CSF (150:1 molar) (curve 2). The samples were heated to 95° C. and cooled to 10° C. The rhG-CSF concentration in the samples was 80 μg/ml, pH 6.0.
Figure 13:
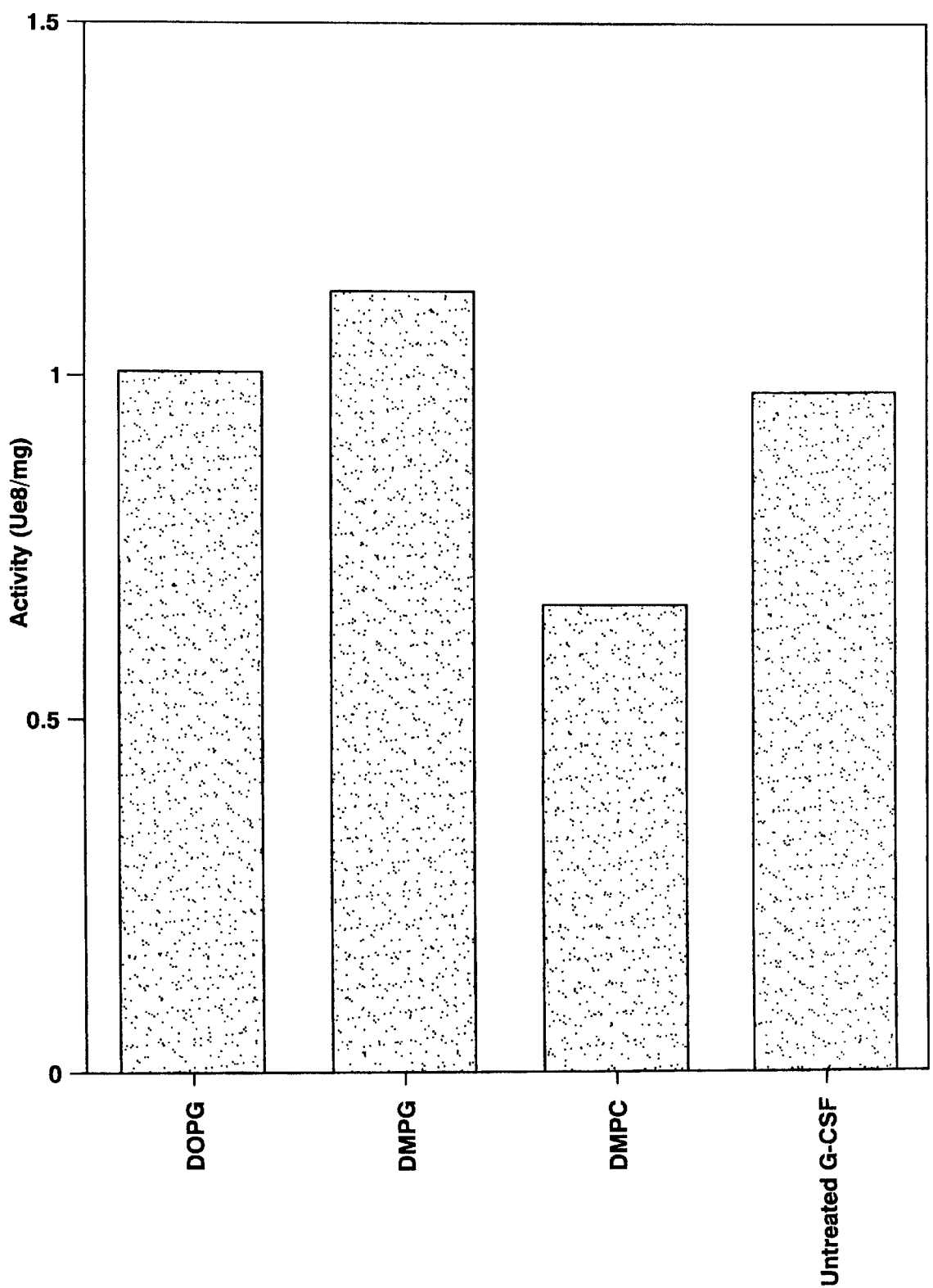
FIG. 13 is a graph showing the ability of various lipids to stabilize rhG-CSF during freeze-drying. The lipid:protein ratio was 100:1 in each case. Stability was based upon retention of in vitro activity in the bone marrow assay. rhG-CSF alone does not survive the freeze-drying process so the control used is untreated rhG-CSF in the absence of lipid.
Figure 25:
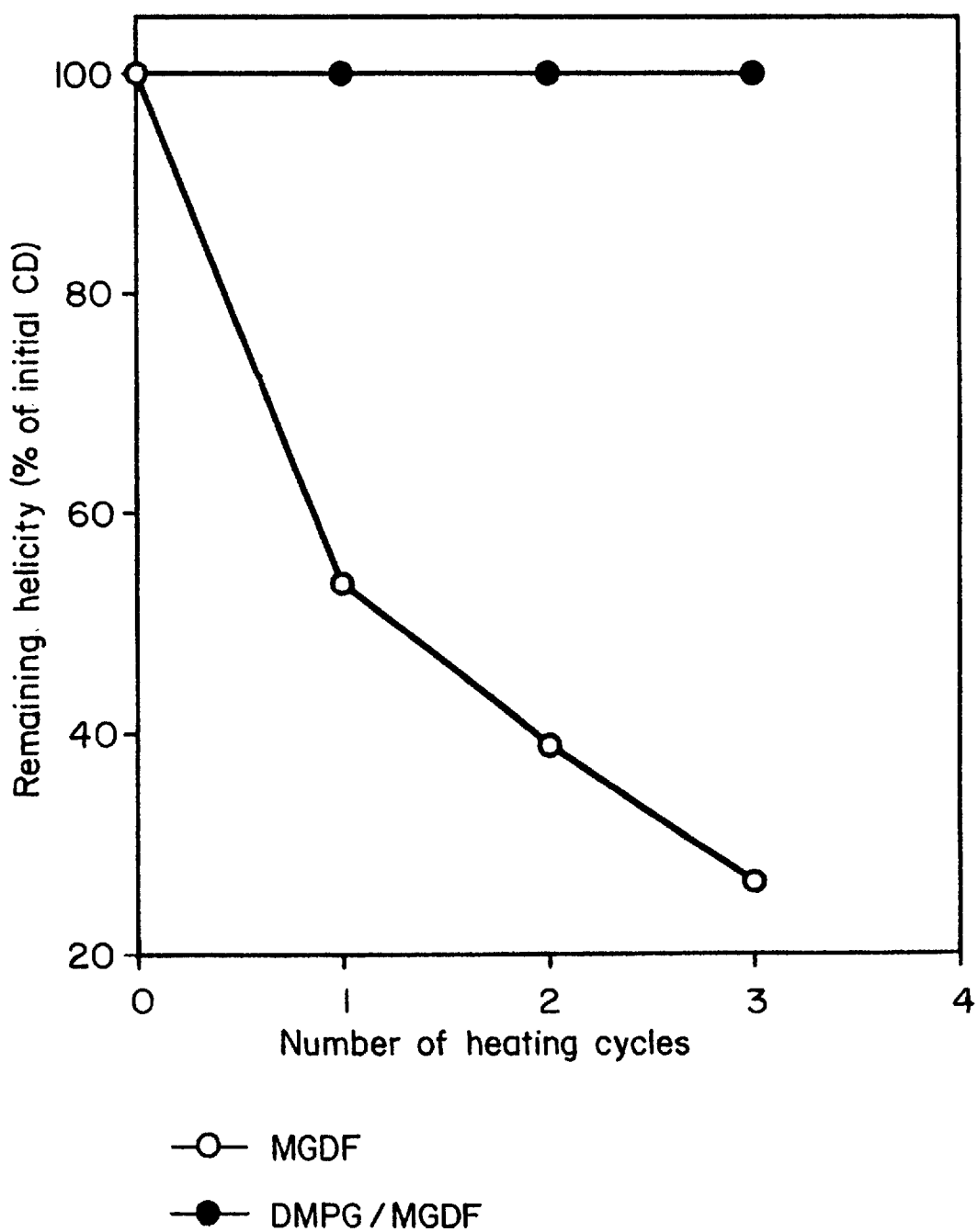
FIG. 25 shows the effect of temperature cycling on the CD of MGDF (○) and DMPG:MGDF (100:1 molar) (●). The MGDF was E. coli derived MGDF 1-163. The % remaining helicity refers to the amount of CD detected at 10° C. after each cycle (one cycle=samples were rapidly heated to 95° C. and cooled to 10° C.).

The circular dichroism (CD at 222 nm) of MGDF alone or inserted into DMPG vesicles was monitored as a function of thermal cycling between 95° C. and 10° C. as described in EXAMPLE 3, FIG. 10. The % remaining CD refers to the amount of CD detected (at 10° C.) after each cycle (one cycle is 10° C.$\rightarrow$95° C.$\rightarrow$10° C.) as compared to the CD of an unheated sample of the indicated composition. While MGDF loses more than 70% of its helicity after 3 cycles of heating, DMPG:MGDF fully retains its original alpha helicity under the same conditions (see FIG. 25).

2. Stability in Presence of Urea

Figure 26:
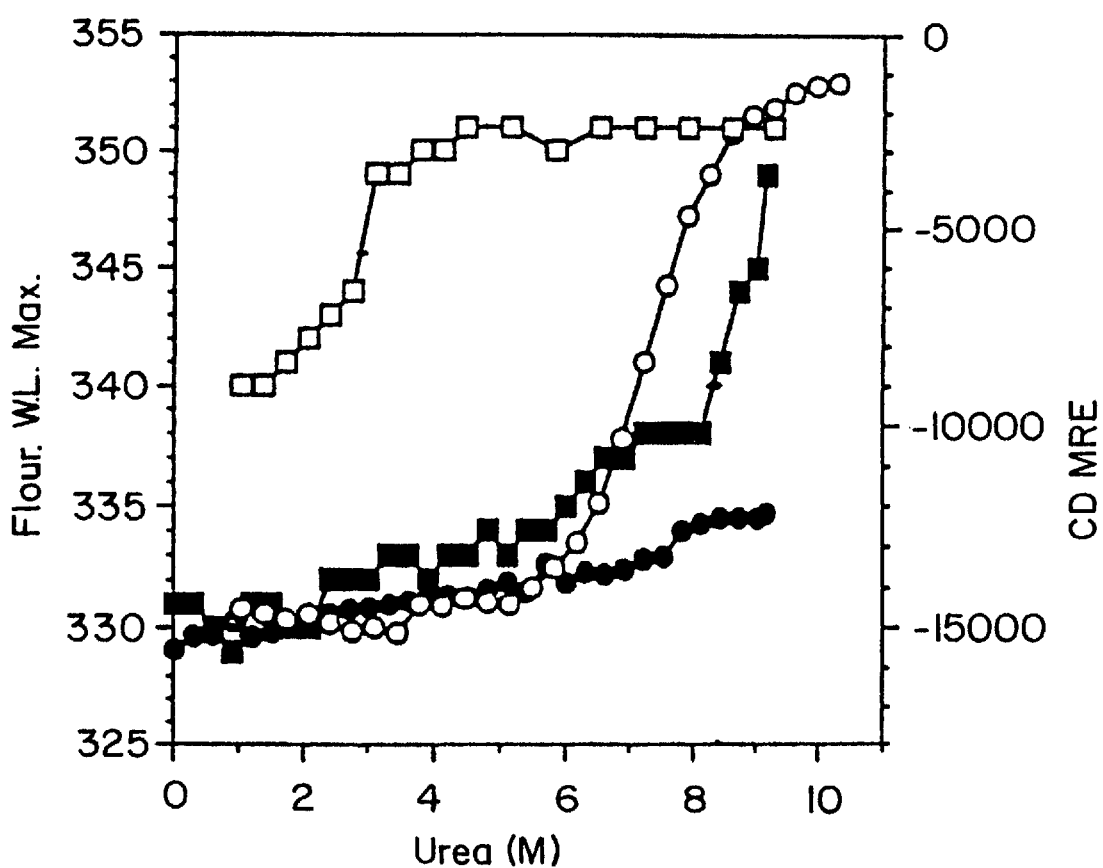
FIG. 26 shows the extent of MGDF (±DMPG) denaturation in the presence of various concentrations of urea. Circular Dichroism MRE for MGDF (-○-) and DMPG-:MGDF (-●-) is depicted as well as MGDF (-□-) and DMPG:MGDF(-■-) flourescence emission maximum. The MGDF was E. coli derived MGDF 1-163. The DMPG-:MGDF ratio was 100:1 (mole:mole).

Urea is a chaotropic reagent which can unfold and denature proteins. The equilibrium denaturation of MGDF ($\pm$DMPG) was monitored by flourescence, i.e., measure of tertiary structure, and by circular dichroism, i.e., a measure of secondary structure. As depicted in FIG. 26, as the protein tertiary structure is lost, the tryptophan residues are more exposed to the water phase and the emission wavelength of MGDF is shifted to longer wavelengths; and, as secondary structure is lost, the mean residue elipicity (MRE) becomes less negative as alpha helicity is lost. In the absence of DMPG, 50% loss of tertiary structure occurs at around 3M urea, whereas 8M urea is required to achieve 50% loss of structure in the presence of DMPG. Similarly, a 50% loss of MGDF MRE requires 7M urea in the absence of DMPG, compared to 9M urea in the presence of DMPG.

3. Shelf-life Stability *E. coli* MGDF 1-163 ($\pm$DMPG) was stored under the conditions indicated in TABLE 2 below and then examined by size exclusion chromatography (SEC) using a Toso-Haas G3000SWXL column with a mobile phase of 100 mM phosphate buffer, 10% ethanol, 0.2% Tween-20, pH 6.9. Samples were diluted with ethanol and Tween-20 to the same concentration as used in the mobile phase and 10–20 $\mu$g sample were injected per run. The column temperature was maintained at 40° C. Any aggregated MGDF which forms elutes earlier than the non-aggregated protein and is quantitated by measuring the area under the curve of the aggregate peak and the monomer peak. Data refer to the % of total MGDF in the aggregate peak.

TABLE 2

|  |  | % aggregation as measured by SEC | |
| --- | --- | --- | --- |
| Sample | Temperature | 5 weeks | 11 weeks |
| MGDF | −80° C. | 0 | 0.2 |
|  | 4° C. | 0.4 | 0.6 |
|  | 37° C. | 18 | 39.2 |
| DMPG:MGDF | −80° C. | 0 | 0.14 |
|  | 4° C. | 0 | 0 |

TABLE 2-continued

| | % aggregation as measured by SEC | | |
|---|---|---|---|
| Sample | Temperature | 5 weeks | 11 weeks |
| | 37° C. | 1.9 | 2.5 |

As shown in TABLE 2, DMPG dramatically reduces the formation of aggregates upon storage. DMPG can thus be used to enhance the shelf-life of MGDF.

These data demonstrate that the interaction of MGDF with DMPG vesicles enhances the stability of the protein under conditions where MGDF alone is unstable. The interaction directly stabilizes the secondary and tertiary structure of MGDF in the presence of denaturants like urea, and significantly improves the shelf-life of MGDF at various temperatures.

EXAMPLE 10

In this example, chemically modified MGDF 1-163 (mono-pegylated (20 kDa) MGDF 1-163 (PEG-MGDF)) was tested for its ability to interact with negatively charged lipid vesicles. For the PEG-MGDF, the determinations were made using comparisons of $F/F_0$ intensity and emission maximums (as described in EXAMPLES 1 and 8 above). In each instance, the mole ratio of lipid:protein was 100:1.

PEG-MGDF used in these experiments mono-pegylated (20 kDa) E. coli derived MGDF 1-163 using monomethoxy-polyethylene glycol aldehyde (MePEG) (average molecular weight 20 kDa) via reductive alkylation. The homogeneity of the PEG-MGDF conjugates was determined by Sodium Dodecyl Sulfate Polyacrylamide Gel Electrophoresis using 4–20% precast gradient gels (NOVEX). One major band corresponding to the position of a 46.9 kDa protein was revealed.

Figure 27:
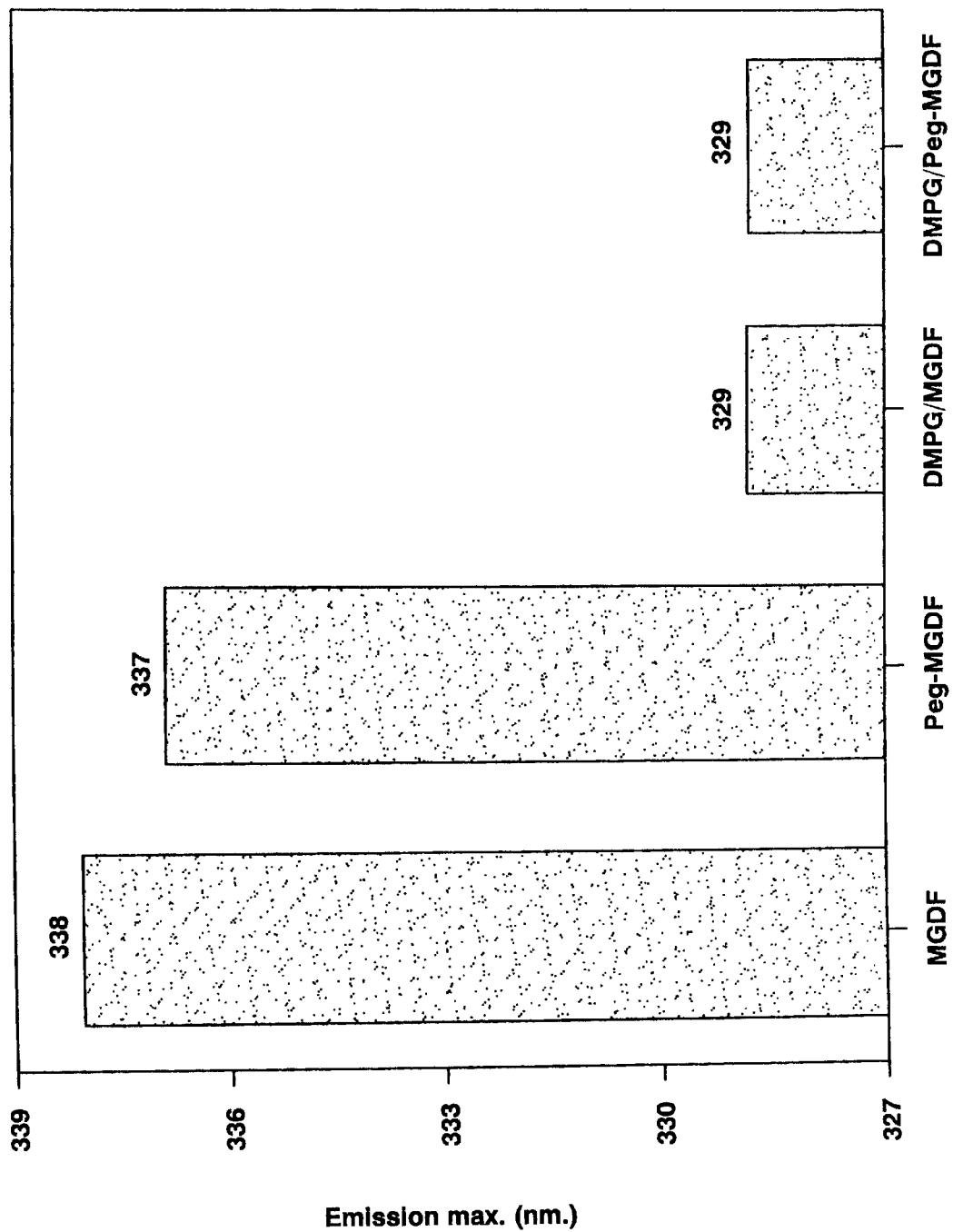
FIG. 27 is a graphical representation of the fluorescence emission maxima for MGDF (±DMPG) and PEG-MGDF (±DMPG). The MGDF was E. coli derived MGDF 1-163, and the PEG-MGDF was mono-pegylated E. coli derived MGDF 1-163. The DMPG:MGDF and DMPG:PEG-MGDF ratio was 100:1 (mole:mole).

DMPG:PEG-MGDF (100:1 mole/mole) samples were then prepared using procedures described above. The DMPG:PEG-MGDF samples were found to fully recover secondary structure after heating (FIG. 27). Despite the presence of the PEG molecules, the derivatized protein was able interact with the lipid in the same way as the native protein.

This data shows that the emission maxima shifts associated with MGDF interaction with a negatively charged lipid vesicle is not unique only to MGDF obtained as a product of procaryotic host cell expression. As was demonstrated with chemically modified rhG-CSF, DMPG:PEG-MGDF also exhibited emission shifts and the data show that chemically modified MGDF can insert into membranes composed of DMPG.

EXAMPLE 11

Figure 28:
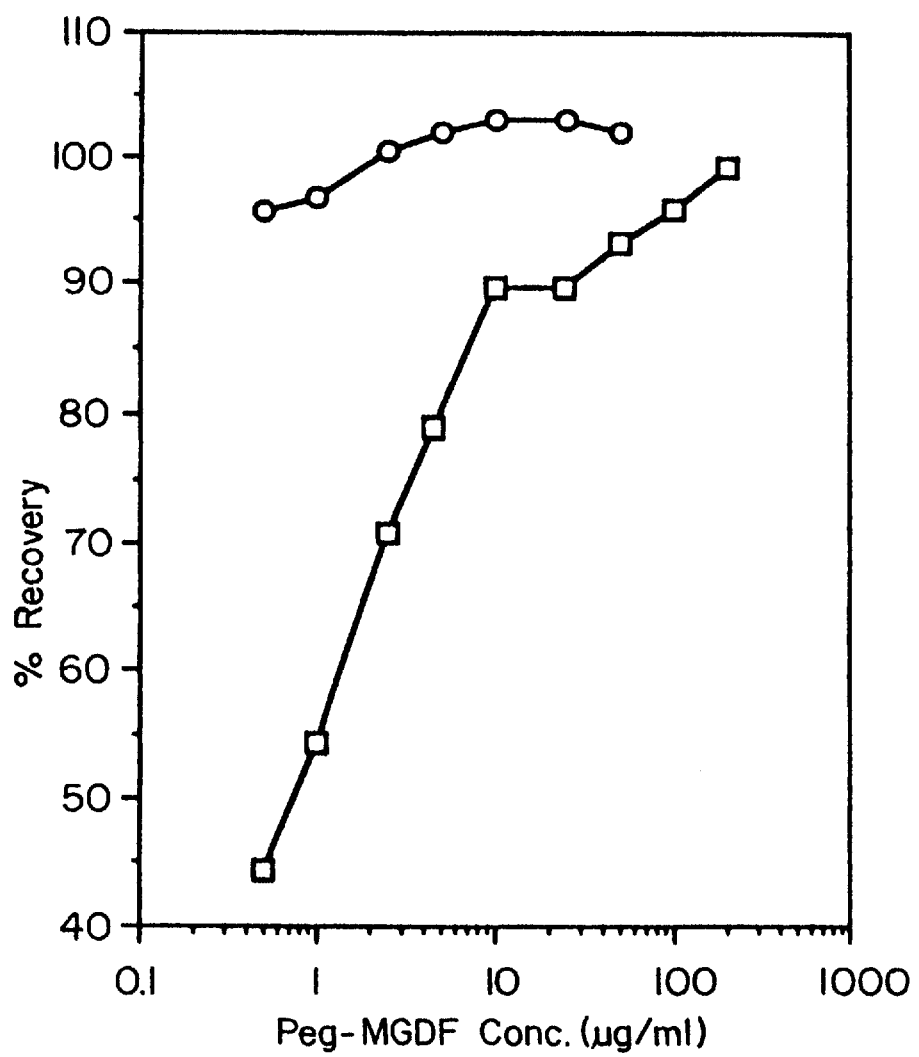
FIG. 28 shows the extent of PEG-MGDF (±DMPG) adsorption to glass vials at various PEG-MGDF concentrations. The MGDF was E. coli derived MGDF 1-163, and the PEG-MGDF was mono-pegylated E. coli derived MGDF 1-163. The % recovery of PEG-MGDF (-□-) and DMPG:PEG-MGDF (-o-) was assayed by counting the amount of radiolabeled MGDF recoverable from the glass vials after an 18 hour incubation at room temperature.

In this example, the effect of the DMPG:PEG-MGDF interaction as it relates to the problem of MGDF adsorption to glass vials was evaluated. Around 11 pg/ml of [$^{125}$I]-PEG-MGDF was combined with various concentrations of unlabeled PEG-MGDF to achieve the indicated final PEG-MGDF concentrations (see FIG. 28). Where indicated, DMPG was included in the dilution (see also FIG. 27). 1 mL of the preparations was placed in 3 cc glass vials (Kimble). The % recovery of PEG-MGDF was assayed by counting the amount of radiolabeled MGDF recoverable from the glass vials after an 18 hour incubation at room temperature. As shown in FIG. 28, PEG-MGDF adsorbs readily to the glass containers as the concentration of the protein is lowered, and the adsorption is especially high in the range of 0.1–50 µg/ml. By contrast, DMPG:PEG-MGDF samples show almost no adsorption to glass in the range of 0.1–50 µg/ml PEG-MGDF.

EXAMPLE 12

Figure 31:
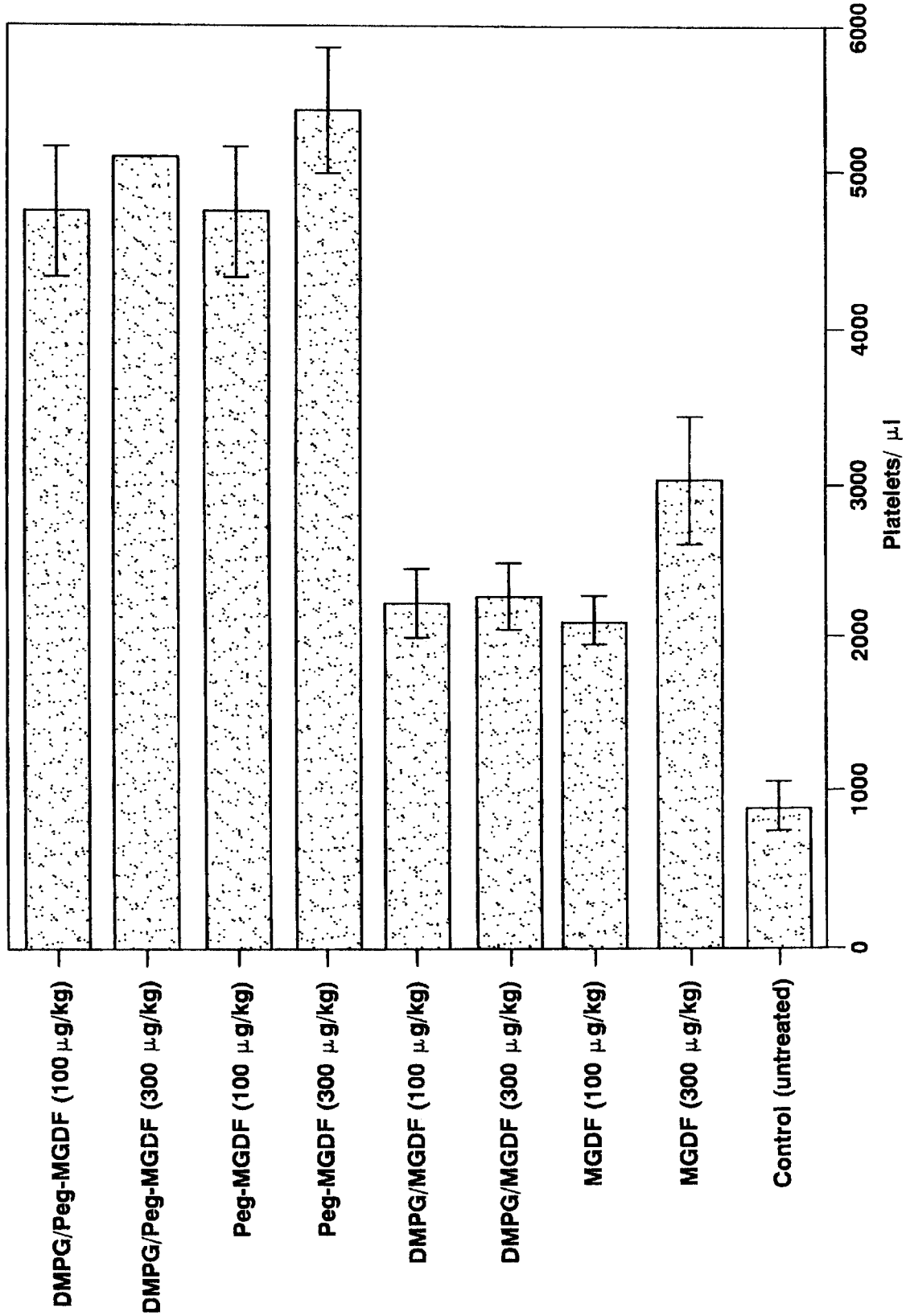
FIG. 31 shows in vivo activity of DMPG:MGDF and DMPG:PEG-MGDF in normal mice, in terms of platelet counts. The MGDF was E. coli derived MGDF 1-163, and the PEG-MGDF was mono-pegylated E. coli derived MGDF 1-163. The DMPG:MGDF and DMPG:PEG-MGDF dose was 100 μg/kg and 300 μg/kg and the lipid:protein ratio was 100:1

In this example, the effect of the DMPG:MGDF 1-163 and DMPG:PEG-MGDF 1-163 interaction as it relates to the biological activity of MGDF 1-163 and PEG-MGDF 1-163 was determined. The MGDF 1-163 was E. coli derived, and the lipid:protein ratio was 100:1. Platelet counts from mice treated with 100 µg/kg and 300 µg/kg MGDF, PEG-MGDF, DMPG:MGDF or DMPG:PEG-MGDF were measured and the results are presented in FIG. 31. The indicated concentration of each form was administered subcutaneously into normal, female Balb/c mice once daily for 8 days. Test bleeds from a small lateral cut in a tail vein were collected 24 hours after the last injection. Blood cell analyses were performed with a Sysmex electronic blood cell analyzer (Baxter Diagnostics, Inc. Irvine, Calif.). Data are represented as the mean of determinations of 4 animals, +/- standard error of the mean. Other blood cell parameters such as total white blood cell counts or red blood cell counts were not affected by these treatments (data not shown). The results indicate that pegylation of E. coli MGDF 1-163 increased the in vivo activity of the molecule. More importantly, the studies above demonstrate that insertion into negatively charged lipid bilayers does not adversely affect the biological activity of the various MGDF forms.

What is claimed is:

1. A composition comprising a cytokine mixed with a pre-formed intact phospholipid liposome vesicle, said liposome vesicle composed of negatively charged phospholipids, wherein said composition has at least a 25:1 (mole:mole) ratio of liposome:cytokine, to form a liposome-cytokine complex wherein only a portion of the cytokine is inserted into the lipid portion of the liposome vesicle, wherein said liposome-cytokine complex is directly stabilized against unfolding of the secondary structure of said cytokine, and wherein said composition has improved shelf life.

2. The composition of claim 1 wherein said composition has a pH of 3.0–7.5.

3. The composition of claim 1 wherein said liposome vesicle is selected from the group consisting of dioleoylphosphatidylglycerol (DOPG), dimyristoylphosphatidylglycerol (DMPG), dipalmitoylphosphatidylglycerol (DPPG), eggphosphatidylglycerol, dioleoylphosphatidylethanolamine (DOPE), eggphosphatidylethanolamine, dioleoylphosphatidic acid (DOPA), dimyristoylphosphatidic acid (DMPA), dipalmitoylphosphatidic acid (DPPA), dioleoylphosphatidylserine (DOPS), dimyristoylphosphatidylserine (DMPS), dipalmitoylphosphatidylserine (DPPS), eggphosphatidylserine, lysophosphatidylglycerol, lysophosphatidylethanolamine, and lysophosphatidylserine.

4. The composition of claim 1 wherein said cytokine is a hematopoietic factor.

5. The composition of claim 4 wherein said hematopoietic factor is selected from the group consisting of G-CSF, GM-CSF and MGDF.

6. The composition of claim 5 wherein said hematopoietic factor is G-CSF.

7. The composition of claim 6 wherein the G-CSF is natural human G-CSF or is obtained as a product of procaryotic or eukaryotic host cell expression.

8. The composition of claim 6 wherein the G-CSF is chemically modified G-CSF.

9. The composition of claim 8 wherein the chemically modified G-CSF is pegylated G-CSF.

10. The composition of claim 5 wherein said hematopoietic factor is MGDF.

11. The composition of claim 10 wherein the MGDF is natural human MGDF or is obtained as a product of procaryotic or eukaryotic host cell expression.

12. The composition of claim 11 wherein the MGDF has an amino acid sequence comprising amino acids 1–163 of FIG. 29 (SEQ ID Nos:1 and 2).

13. The composition of claim 11 wherein the MGDF has an amino acid sequence comprising amino acids 1–332 of FIG. 29 (SEQ ID Nos:1 and 2).

14. The composition of claim 10 wherein the MGDF is chemically modified MGDF.

15. The composition of claim 14 wherein the chemically modified MGDF is pegylated MGDF (PEG-MGDF).

16. The composition of claim 15 wherein the PEG-MGDF is pegylated with polyethylene glycol.

17. The composition of claim 16 wherein the PEG-MGDF is mono-pegylated MGDF (mPEG-MGDF).

18. The composition of claim 17 wherein the PEG group is attached to the N-terminus thereof.

19. The composition of claim 1 wherein said composition contains a pharmaceutically acceptable carrier.

20. The composition of claim 1 wherein said protein is *E. coli* derived rhG-CSF, wherein said liposome vesicle is DOPG, and wherein said composition has a 50:1 ratio of DOPG:rhG-CSF, has a pH of 4.5 and contains 10 mM sodium acetate.

21. The composition of claim 1 wherein said protein is *E. coli* derived MGDF comprising amino acids 1–163 of FIG. 29 (SEQ ID Nos:1 and 2), wherein said liposome vesicle is DMPG, and wherein said composition has a 100:1 ratio of DMPG:MGDF, has a pH of 5.0 and contains 10 mM sodium acetate, 5% sorbitol.

22. The composition of claim 1 wherein said protein is mono-pegylated *E. coli* derived MGDF (mPEG-MGDF), wherein said liposome vesicle is DMPG, and wherein said composition has a 100:1 ratio of DMPG:mPEG-MGDF, has a pH of 5.0 and contains 10 mm sodium acetate, 5% sorbitol.

23. The composition of claim 1 wherein said protein is CHO derived MGDF comprising amino acids 1–332 of FIG. 29 (SEQ ID Nos:1 and 2), wherein said liposome vesicle is DMPG, and wherein said composition has a 100:1 ratio of DMPG:MGDF, has a pH of 5.0 and contains 10 mM sodium acetate, 5% sorbitol.

24. A method of preparing a liposome-cytokine composition comprising mixing a cytokine with a pre-formed intact phospholipid liposome vesicle, wherein said liposome vesicle is negatively charged, wherein said composition has at least a 25:1 (mole:mole) ratio of liposome:cytokine, wherein only a portion of said cytokine is inserted into the lipid portion of said liposome vesicle, wherein said liposome-cytokine complex is directly stabilized against unfolding of the secondary structure of said cytokine, wherein said composition has improved shelf life, and obtaining said liposome-cytokine composition.

25. A method according to claim 24 wherein said composition has a pH of 3.0–7.5.

26. A method according to claim 24 wherein said liposome vesicle is prepared from a lipid selected from the group consisting of dioleoylphosphatidylglycerol (DOPG), dimyristoylphosphatidylglycerol (DMPG), dipalmitoylphosphatidylglycerol (DPPG), eggphosphatidylglycerol, dioleoylphosphatidylethanolamine (DOPE), eggphosphatidylethanolamine, dioleoylphosphatidic acid (DOPA), dimyristoylphosphatidic acid (DMPA), dipalmitoylphosphatidic acid (DPPA), dioleoylphosphatidylserine (DOPS), dimyristoylphosphatidylserine (DMPS), dipalmitoylphosphatidylserine (DPPS), eggphosphatidylserine, lysophosphatidylglycerol, lysophosphatidylethanolamine, and lysophosphatidylserine.

27. A method according to claim 24 wherein said cytokine is a hematopoietic factor.

28. A method according to claim 27 wherein said hematopoietic factor is selected from the group consisting of G-CSF, GM-CSF and MGDF.

29. A method according to claim 28 wherein said hematopoietic factor is G-CSF.

30. A method according to claim 29 wherein the G-CSF is natural human G-CSF or is obtained as a product of procaryotic or eukaryotic host cell expression.

31. A method according to claim 29 wherein the G-CSF is chemically modified G-CSF.

32. A method according to claim 31 wherein the chemically modified G-CSF is pegylated G-CSF.

33. A method according to claim 28 wherein said hematopoietic factor is MGDF.

34. A method according to claim 33 wherein the MGDF is natural human MGDF or is obtained as a product of procaryotic or eukaryotic host cell expression.

35. A method according to claim 34 wherein the MGDF has an amino acid sequence comprising amino acids 1–163 of FIG. 29 (SEQ ID Nos:1 and 2).

36. A method according to claim 34 wherein the MGDF has an amino acid sequence comprising amino acids 1–332 of FIG. 29 (SEQ ID Nos:1 and 2).

37. A method according to claim 35 wherein the MGDF is chemically modified MGDF.

38. A method according to claim 37 wherein the chemically modified MGDF is pegylated MGDF (PEG-MGDF).

39. A method according to claim 38 wherein the PEG-MGDF is pegylated with polyethylene glycol.

40. A method according to claim 39 wherein the PEG-MGDF is mono-pegylated MGDF (mPEG-MGDF).

41. A method according to claim 40 wherein the PEG group is attached to the N-terminus thereof.

42. A method according to claim 24 wherein said composition contains a pharmaceutically acceptable carrier.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1342 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
    ( A ) NAME/KEY: CDS
    ( B ) LOCATION: 36..1094

( i x ) FEATURE:
    ( A ) NAME/KEY: mat_peptide
    ( B ) LOCATION: 99..1094

( i x ) FEATURE:
    ( A ) NAME/KEY: sig_peptide
    ( B ) LOCATION: 36..98

( x i ) SEQUENCE DESCRIPTION: SEQ ID NO:1:

```
CAGGGAGCCA CGCCAGCCAA GACACCCCGG CCAGA ATG GAG CTG ACT GAA TTG         53
                                        Met Glu Leu Thr Glu Leu
                                        -21             -20

CTC CTC GTG GTC ATG CTT CTC CTA ACT GCA AGG CTA ACG CTG TCC AGC       101
Leu Leu Val Val Met Leu Leu Leu Thr Ala Arg Leu Thr Leu Ser Ser
-15                 -10                 -5                    1

CCG GCT CCT CCT GCT TGT GAC CTC CGA GTC CTC AGT AAA CTG CTT CGT       149
Pro Ala Pro Pro Ala Cys Asp Leu Arg Val Leu Ser Lys Leu Leu Arg
                5                   10                  15

GAC TCC CAT GTC CTT CAC AGC AGA CTG AGC CAG TGC CCA GAG GTT CAC       197
Asp Ser His Val Leu His Ser Arg Leu Ser Gln Cys Pro Glu Val His
            20                  25                  30

CCT TTG CCT ACA CCT GTC CTG CTG CCT GCT GTG GAC TTT AGC TTG GGA       245
Pro Leu Pro Thr Pro Val Leu Leu Pro Ala Val Asp Phe Ser Leu Gly
        35                  40                  45

GAA TGG AAA ACC CAG ATG GAG GAG ACC AAG GCA CAG GAC ATT CTG GGA       293
Glu Trp Lys Thr Gln Met Glu Glu Thr Lys Ala Gln Asp Ile Leu Gly
50                  55                  60                  65

GCA GTG ACC CTT CTG CTG GAG GGA GTG ATG GCA GCA CGG GGA CAA CTG       341
Ala Val Thr Leu Leu Leu Glu Gly Val Met Ala Ala Arg Gly Gln Leu
                70                  75                  80

GGA CCC ACT TGC CTC TCA TCC CTC CTG GGG CAG CTT TCT GGA CAG GTC       389
Gly Pro Thr Cys Leu Ser Ser Leu Leu Gly Gln Leu Ser Gly Gln Val
            85                  90                  95

CGT CTC CTC CTT GGG GCC CTG CAG AGC CTC CTT GGA ACC CAG CTT CCT       437
Arg Leu Leu Leu Gly Ala Leu Gln Ser Leu Leu Gly Thr Gln Leu Pro
        100                 105                 110

CCA CAG GGC AGG ACC ACA GCT CAC AAG GAT CCC AAT GCC ATC TTC CTG       485
Pro Gln Gly Arg Thr Thr Ala His Lys Asp Pro Asn Ala Ile Phe Leu
115                 120                 125

AGC TTC CAA CAC CTG CTC CGA GGA AAG GTG CGT TTC CTG ATG CTT GTA       533
Ser Phe Gln His Leu Leu Arg Gly Lys Val Arg Phe Leu Met Leu Val
130                 135                 140                 145

GGA GGG TCC ACC CTC TGC GTC AGG CGG GCC CCA CCC ACC ACA GCT GTC       581
Gly Gly Ser Thr Leu Cys Val Arg Arg Ala Pro Pro Thr Thr Ala Val
                150                 155                 160

CCC AGC AGA ACC TCT CTA GTC CTC ACA CTG AAC GAG CTC CCA AAC AGG       629
Pro Ser Arg Thr Ser Leu Val Leu Thr Leu Asn Glu Leu Pro Asn Arg
            165                 170                 175

ACT TCT GGA TTG TTG GAG ACA AAC TTC ACT GCC TCA GCC AGA ACT ACT       677
Thr Ser Gly Leu Leu Glu Thr Asn Phe Thr Ala Ser Ala Arg Thr Thr
        180                 185                 190

GGC TCT GGG CTT CTG AAG TGG CAG CAG GGA TTC AGA GCC AAG ATT CCT       725
Gly Ser Gly Leu Leu Lys Trp Gln Gln Gly Phe Arg Ala Lys Ile Pro
195                 200                 205

GGT CTG CTG AAC CAA ACC TCC AGG TCC CTG GAC CAA ATC CCC GGA TAC       773
Gly Leu Leu Asn Gln Thr Ser Arg Ser Leu Asp Gln Ile Pro Gly Tyr
210                 215                 220                 225

CTG AAC AGG ATA CAC GAA CTC TTG AAT GGA ACT CGT GGA CTC TTT CCT       821
Leu Asn Arg Ile His Glu Leu Leu Asn Gly Thr Arg Gly Leu Phe Pro
```

|     |     |     |     |     | 230 |     |     |     | 235 |     |     |     | 240 |     |      |
|-----|-----|-----|-----|-----|-----|-----|-----|-----|-----|-----|-----|-----|-----|-----|------|
| GGA | CCC | TCA | CGC | AGG | ACC | CTA | GGA | GCC | CCG | GAC | ATT | TCC | TCA | GGA | ACA  | 869
| Gly | Pro | Ser | Arg | Arg | Thr | Leu | Gly | Ala | Pro | Asp | Ile | Ser | Ser | Gly | Thr  |
|     |     |     | 245 |     |     |     |     | 250 |     |     |     |     | 255 |     |      |
| TCA | GAC | ACA | GGC | TCC | CTG | CCA | CCC | AAC | CTC | CAG | CCT | GGA | TAT | TCT | CCT  | 917
| Ser | Asp | Thr | Gly | Ser | Leu | Pro | Pro | Asn | Leu | Gln | Pro | Gly | Tyr | Ser | Pro  |
|     |     | 260 |     |     |     |     | 265 |     |     |     |     | 270 |     |     |      |
| TCC | CCA | ACC | CAT | CCT | CCT | ACT | GGA | CAG | TAT | ACG | CTC | TTC | CCT | CTT | CCA  | 965
| Ser | Pro | Thr | His | Pro | Pro | Thr | Gly | Gln | Tyr | Thr | Leu | Phe | Pro | Leu | Pro  |
|     | 275 |     |     |     |     | 280 |     |     |     |     | 285 |     |     |     |      |
| CCC | ACC | TTG | CCC | ACC | CCT | GTG | GTC | CAG | CTC | CAC | CCC | TG  | CTT | CCT | GAC  | 1013
| Pro | Thr | Leu | Pro | Thr | Pro | Val | Val | Gln | Leu | His | Pro | Leu | Leu | Pro | Asp  |
| 290 |     |     |     |     | 295 |     |     |     |     | 300 |     |     |     |     | 305  |
| CCT | TCT | GCT | CCA | ACG | CCC | ACC | CCT | ACC | AGC | CCT | CTT | CTA | AAC | ACA | TCC  | 1061
| Pro | Ser | Ala | Pro | Thr | Pro | Thr | Pro | Thr | Ser | Pro | Leu | Leu | Asn | Thr | Ser  |
|     |     |     | 310 |     |     |     |     | 315 |     |     |     |     | 320 |     |      |
| TAC | ACC | CAC | TCC | CAG | AAT | CTG | TCT | CAG | GAA | GGG | TAAGGTTCTC | AGACACTGCC |     |     | 1114
| Tyr | Thr | His | Ser | Gln | Asn | Leu | Ser | Gln | Glu | Gly |     |     |     |     |      |
|     |     |     | 325 |     |     |     |     | 330 |     |     |     |     |     |     |      |

GACATCAGCA  TTGTCTCGTG  TACAGCTCCC  TTCCCTGCAG  GGCGCCCCTG  GGAGACAACT      1174

GGACAAGATT  TCCTACTTTC  TCCTGAAACC  CAAAGCCCTG  GTAAAAGGGA  TACACAGGAC      1234

TGAAAAGGGA  ATCATTTTTC  ACTGTACATT  ATAAACCTTC  AGAAGCTATT  TTTTAAGCT       1294

ATCAGCAATA  CTCATCAGAG  CAGCTAGCTC  TTTGGTCTAT  TTTCTGCA                    1342

( 2 ) INFORMATION FOR SEQ ID NO:2:

( i ) SEQUENCE CHARACTERISTICS:
        ( A ) LENGTH: 353 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Glu | Leu | Thr | Glu | Leu | Leu | Leu | Val | Val | Met | Leu | Leu | Leu | Thr | Ala |
|-----|-----|-----|-----|-----|-----|-----|-----|-----|-----|-----|-----|-----|-----|-----|-----|
| -21 | -20 |     |     |     |     | -15 |     |     |     | -10 |     |     |     |     |     |

| Arg | Leu | Thr | Leu | Ser | Ser | Pro | Ala | Pro | Ala | Cys | Asp | Leu | Arg | Val |
|-----|-----|-----|-----|-----|-----|-----|-----|-----|-----|-----|-----|-----|-----|-----|
| -5  |     |     |     |     | 1   |     |     | 5   |     |     |     |     | 10  |     |

| Leu | Ser | Lys | Leu | Leu | Arg | Asp | Ser | His | Val | Leu | His | Ser | Arg | Leu | Ser |
|-----|-----|-----|-----|-----|-----|-----|-----|-----|-----|-----|-----|-----|-----|-----|-----|
|     |     |     | 15  |     |     |     |     | 20  |     |     |     |     | 25  |     |     |

| Gln | Cys | Pro | Glu | Val | His | Pro | Leu | Pro | Thr | Pro | Val | Leu | Leu | Pro | Ala |
|-----|-----|-----|-----|-----|-----|-----|-----|-----|-----|-----|-----|-----|-----|-----|-----|
|     |     |     | 30  |     |     |     |     | 35  |     |     |     |     | 40  |     |     |

| Val | Asp | Phe | Ser | Leu | Gly | Glu | Trp | Lys | Thr | Gln | Met | Glu | Glu | Thr | Lys |
|-----|-----|-----|-----|-----|-----|-----|-----|-----|-----|-----|-----|-----|-----|-----|-----|
|     |     | 45  |     |     |     |     | 50  |     |     |     |     | 55  |     |     |     |

| Ala | Gln | Asp | Ile | Leu | Gly | Ala | Val | Thr | Leu | Leu | Leu | Glu | Gly | Val | Met |
|-----|-----|-----|-----|-----|-----|-----|-----|-----|-----|-----|-----|-----|-----|-----|-----|
| 60  |     |     |     |     |     | 65  |     |     |     |     | 70  |     |     |     | 75  |

| Ala | Ala | Arg | Gly | Gln | Leu | Gly | Pro | Thr | Cys | Leu | Ser | Ser | Leu | Leu | Gly |
|-----|-----|-----|-----|-----|-----|-----|-----|-----|-----|-----|-----|-----|-----|-----|-----|
|     |     |     |     | 80  |     |     |     |     | 85  |     |     |     |     | 90  |     |

| Gln | Leu | Ser | Gly | Gln | Val | Arg | Leu | Leu | Leu | Gly | Ala | Leu | Gln | Ser | Leu |
|-----|-----|-----|-----|-----|-----|-----|-----|-----|-----|-----|-----|-----|-----|-----|-----|
|     |     |     |     | 95  |     |     |     |     | 100 |     |     |     |     | 105 |     |

| Leu | Gly | Thr | Gln | Leu | Pro | Pro | Gln | Gly | Arg | Thr | Thr | Ala | His | Lys | Asp |
|-----|-----|-----|-----|-----|-----|-----|-----|-----|-----|-----|-----|-----|-----|-----|-----|
|     |     |     | 110 |     |     |     |     | 115 |     |     |     |     | 120 |     |     |

| Pro | Asn | Ala | Ile | Phe | Leu | Ser | Phe | Gln | His | Leu | Leu | Arg | Gly | Lys | Val |
|-----|-----|-----|-----|-----|-----|-----|-----|-----|-----|-----|-----|-----|-----|-----|-----|
|     |     |     | 125 |     |     |     |     | 130 |     |     |     |     | 135 |     |     |

| Arg | Phe | Leu | Met | Leu | Val | Gly | Gly | Ser | Thr | Leu | Cys | Val | Arg | Arg | Ala |
|-----|-----|-----|-----|-----|-----|-----|-----|-----|-----|-----|-----|-----|-----|-----|-----|
| 140 |     |     |     |     | 145 |     |     |     |     | 150 |     |     |     |     | 155 |

| Pro | Pro | Thr | Thr | Ala | Val | Pro | Ser | Arg | Thr | Ser | Leu | Val | Leu | Thr | Leu |
|-----|-----|-----|-----|-----|-----|-----|-----|-----|-----|-----|-----|-----|-----|-----|-----|

|   |   |   |   |   |   |   |   |   |   |   |   |   |   |   |
|---|---|---|---|---|---|---|---|---|---|---|---|---|---|---|
|   |   |   | 160 |   |   |   |   | 165 |   |   |   |   | 170 |   |
| Asn | Glu | Leu | Pro<br>175 | Asn | Arg | Thr | Ser | Gly<br>180 | Leu | Leu | Glu | Thr | Asn<br>185 | Phe | Thr |
| Ala | Ser | Ala<br>190 | Arg | Thr | Thr | Gly | Ser<br>195 | Gly | Leu | Leu | Lys | Trp<br>200 | Gln | Gln | Gly |
| Phe | Arg<br>205 | Ala | Lys | Ile | Pro | Gly<br>210 | Leu | Leu | Asn | Gln | Thr<br>215 | Ser | Arg | Ser | Leu |
| Asp<br>220 | Gln | Ile | Pro | Gly | Tyr<br>225 | Leu | Asn | Arg | Ile | His<br>230 | Glu | Leu | Leu | Asn | Gly<br>235 |
| Thr | Arg | Gly | Leu | Phe<br>240 | Pro | Gly | Pro | Ser | Arg<br>245 | Arg | Thr | Leu | Gly | Ala<br>250 | Pro |
| Asp | Ile | Ser | Ser<br>255 | Gly | Thr | Ser | Asp | Thr<br>260 | Gly | Ser | Leu | Pro | Pro<br>265 | Asn | Leu |
| Gln | Pro | Gly<br>270 | Tyr | Ser | Pro | Ser | Pro<br>275 | Thr | His | Pro | Pro | Thr<br>280 | Gly | Gln | Tyr |
| Thr | Leu<br>285 | Phe | Pro | Leu | Pro | Pro<br>290 | Thr | Leu | Pro | Thr | Pro<br>295 | Val | Val | Gln | Leu |
| His<br>300 | Pro | Leu | Leu | Pro | Asp<br>305 | Pro | Ser | Ala | Pro | Thr<br>310 | Pro | Thr | Pro | Thr<br>315 | Ser |
| Pro | Leu | Leu | Asn | Thr<br>320 | Ser | Tyr | Thr | His | Ser<br>325 | Gln | Asn | Leu | Ser | Gln<br>330 | Glu |
| Gly |   |   |   |   |   |   |   |   |   |   |   |   |   |   |   |